US012665051B2

(12) United States Patent
Casey et al.

(10) Patent No.: US 12,665,051 B2
(45) Date of Patent: Jun. 23, 2026

(54) DETECTION OF MICROSATELLITE INSTABILITY

(71) Applicant: ROCHE SEQUENCING SOLUTIONS, INC, Pleasanton, CA (US)

(72) Inventors: Fergal Casey, Pleasanton, CA (US); Daniel M. Klass, Livermore, CA (US); Alexander Lovejoy, Newark, CA (US); Seyed Hamid Mirebrahim, Dublin, CA (US); Amrita Pati, San Ramon, CA (US); Hao Wang, Dublin, CA (US)

(73) Assignee: ROCHE SEQUENCING SOLUTIONS, INC, Pleasanton, CA (US)

( * ) Notice: Subject to any disclaimer, the term of this patent is extended or adjusted under 35 U.S.C. 154(b) by 846 days.

(21) Appl. No.: 17/255,389

(22) PCT Filed: Jun. 28, 2019

(86) PCT No.: PCT/EP2019/067371
§ 371 (c)(1),
(2) Date: Dec. 22, 2020

(87) PCT Pub. No.: WO2020/002621
PCT Pub. Date: Jan. 2, 2020

(65) Prior Publication Data
US 2021/0375391 A1 Dec. 2, 2021

Related U.S. Application Data

(60) Provisional application No. 62/692,510, filed on Jun. 29, 2018.

(51) Int. Cl.
*G16B 20/20* (2019.01)
*C12Q 1/6869* (2018.01)

(52) U.S. Cl.
CPC ........... *G16B 20/20* (2019.02); *C12Q 1/6869* (2013.01)

(58) Field of Classification Search
CPC .............................. G16B 20/20; C12Q 1/6869
See application file for complete search history.

(56) References Cited

U.S. PATENT DOCUMENTS 5,856,097 A 1/1999 Pinkel et al.
2020/0115708 A1* 4/2020 Shao .................... C12Q 1/6874

FOREIGN PATENT DOCUMENTS

| CN | 2006122288 A2 | 11/2006 |
| CN | 107513565 A | 12/2017 |
| EP | 2218794 A1 | 8/2010 |
| WO | 2017050934 A1 | 3/2017 |
| WO | 2018037231 A1 | 3/2018 |
| WO | 2018137678 A2 | 8/2018 |
| WO | 2019024598 A1 | 2/2019 |

OTHER PUBLICATIONS

Senan, Siju, Kizhakayil Dhanya, Bhaskaran Sasikumar, and Thotten Elampilay Sheeja. "Methods for development of microsatellite markers: an overview." Microsatellite Markers: Not Sci Biol, 2014, 6(1):1-13. (Year: 2014).*
Ellen Heitzer, Peter Ulz, Jochen B Geigl, Circulating Tumor DNA as a Liquid Biopsy for Cancer, Clinical Chemistry, vol. 61, Issue 1, Jan. 1, 2015, pp. 112-123, https://doi.org/10.1373/clinchem.2014.222679 (Year: 2015).*
Volik, Stanislav, Miguel Alcaide, Ryan D. Morin, and Colin Collins. "Cell-free DNA (cfDNA): clinical significance and utility in cancer shaped by emerging technologies." Molecular Cancer Research 14, No. 10 (2016): 898-908. (Year: 2016).*
Drugs approved for prostate cancer. National Cancer Institute. (2018). https://web.archive.org/web/20180423020510/https://www.cancer.gov/about-cancer/treatment/drugs/prostate (Year: 2018).*
Drugs approved for prostate cancer. National Cancer Institute. (2025).https://www.cancer.gov/about-cancer/treatment/drugs/prostate (Year: 2025).*
Drugs Approved for Endometrial Cancer. National Cancer Institute. (2018). https://web.archive.org/web/20180423021140/https://www.cancer.gov/about-cancer/treatment/drugs/endometrial (Year: 2018).*
Drugs Approved for Endometrial Cancer. National Cancer Institute. (2025). https://www.cancer.gov/about-cancer/treatment/drugs/endometrial (Year: 2025).*
Drugs Approved for Colon and Rectal Cancer. National Cancer Institute. (2018). https://web.archive.org/web/20180423015254/https://www.cancer.gov/about-cancer/treatment/drugs/colorectal (Year: 2018).*
Drugs Approved for Colon and Rectal Cancer. National Cancer Institute. (2025). https://www.cancer.gov/about-cancer/treatment/drugs/colorectal (Year: 2025).*
Baudrin L.G. et al., Molecular and Computational Methods for the Detection of Microsatellite Instability in Cancer, Frontiers in Oncology, (2018),-, vol. 8 Issue 621 11 pages.

(Continued)

Primary Examiner — Karlheinz R. Skowronek
Assistant Examiner — Nidhi Dharithreesan
(74) Attorney, Agent, or Firm — Charney IP Law LLC; Thomas M. Finetti

(57) ABSTRACT

Methods and systems for detecting MSI are provided. Also provided are methods for enriching human genomic DNA for microsatellite loci. Additionally, an oligonucleotide array for detecting MSI is provided. In some embodiments, the method for detecting MSI comprises detecting sequencing reads from a sample for a plurality of microsatellite loci; determining a metric for repeat length distribution (RLD) for each microsatellite locus; comparing the metric to a threshold value for the microsatellite locus; quantifying the number of microsatellite loci having an RLD metric exceeding the threshold value; and comparing the number of microsatellite loci having an RLD metric exceeding the threshold value to a microsatellite instability (MSI) proportion threshold.

18 Claims, 11 Drawing Sheets

(56)         References Cited

OTHER PUBLICATIONS

International Search Report and Written Opinion for PCT/EP2019/
67371, Issued Jun. 29, 2020. 18 pages.
Kautto E.A. et al., Performance evaluation for rapid detection of
pan-cancer microsatellite instability with MANTIS, Oncotarget,
(2016), pp. 7452-7463, vol. 8 Issue 5.
Murphy K.M. et al., Comparison of the Microsatellite Instability
Analysis System and the Bethesda Panel for the Determination of
Microsatellite Instability in Colorectal Cancers, Journal of Molecu-
lar Diagnostics, (2006), pp. 305-311, vol. 8 Issue.
Salipante, S.J. et al., Microsatellite Instability Detection by Next
Generation Sequencing, Clinical Chemistry, (2014), pp. 1192-1199,
vol. 60 Issue 9.
Zhu L. et al., A Novel and Reliable Method to Detect Microsatellite
Instability in Colorectal Cancer by Next-Generation Sequencing,
Journal of Molecular Diagnostics, (2018), pp. 225-231, vol. 20 Issue
2.

* cited by examiner

MSS cell line: CCL-228
(controls in bold)

MSS cell line: CCL-253
(controls in bold, note doublets)

FIG. 8

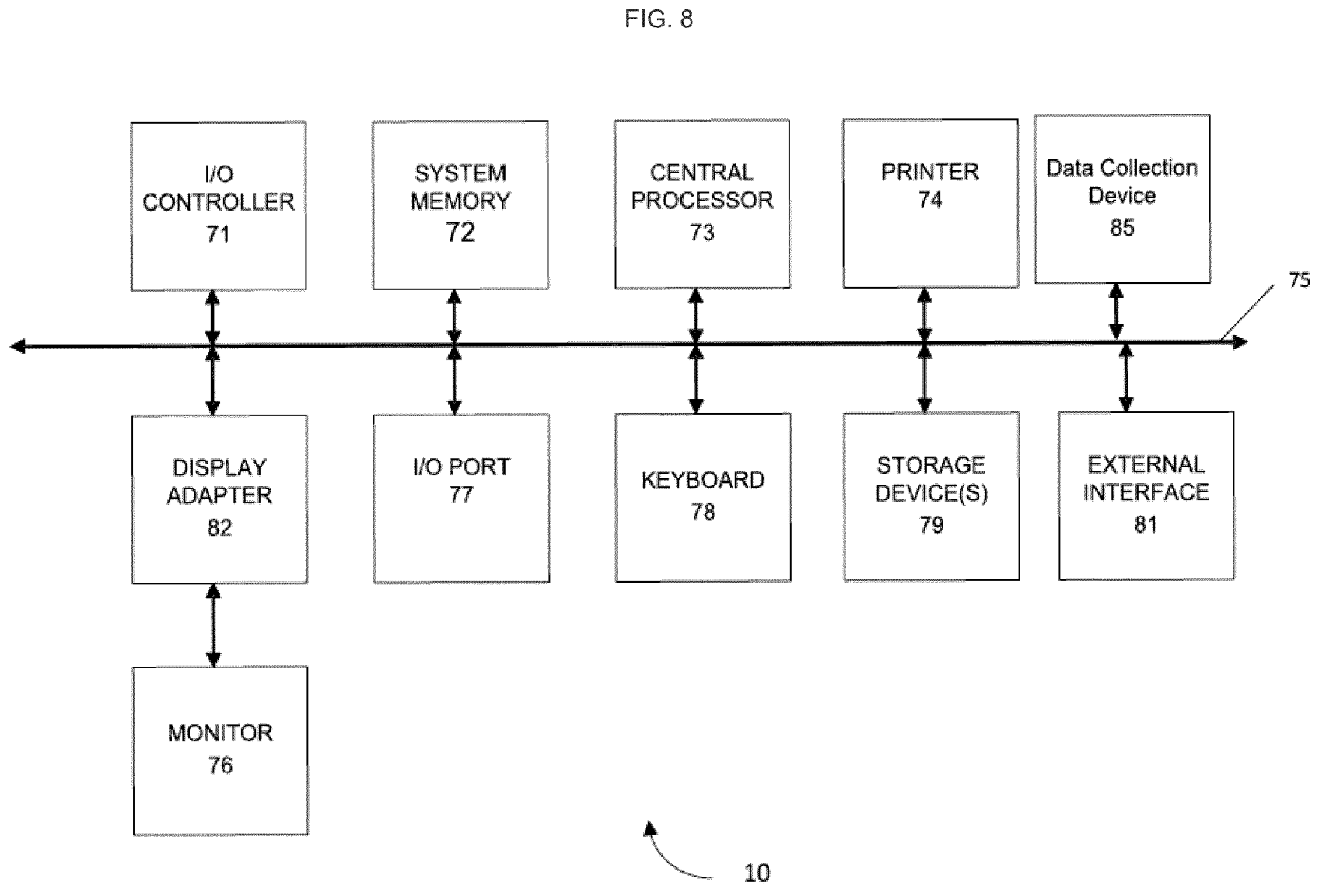

Data Collection Device 85

EXTERNAL INTERFACE 81

PRINTER 74

STORAGE DEVICE(S) 79

CENTRAL PROCESSOR 73

KEYBOARD 78

SYSTEM MEMORY 72

I/O PORT 77

I/O CONTROLLER 71

DISPLAY ADAPTER 82

MONITOR 76

75

10

DETECTION OF MICROSATELLITE INSTABILITY

BACKGROUND OF THE INVENTION

A microsatellite locus is a region of genomic DNA with short tandem repeats (STRs) that are repetitive units of one to six base pairs in length. Hundreds of thousands of microsatellite loci are dispersed throughout the human genome. Microsatellite loci are classified based on the length of the smallest repetitive unit. For example, microsatellite loci with repetitive units of 1 to 6 base pairs in length are termed "mononucleotide", "dinucleotide", "trinucleotide", "tetranucleotide", "pentanucleotide", and "hexanucleotide" repeat loci, respectively. Generally, a microsatellite loci consists of a single repeat type (e.g., $(GT)_n$), which can be repeated up to 100 times, although microsatellites having more than a single repeat type are known as compound microsatellite (e.g., $(GT)_n$ $(CT)_m$). Microsatellite loci may include base substitutions (imperfect microsatellite, e.g., $(GT)_nA(GT)_m$) or insertions (interpreted microsatellite, e.g., $(GT)_nCCC(GT)_m$).

Each microsatellite locus of normal genomic DNA for most diploid species, such as genomic DNA from mammalian species, consists of two alleles at each locus. The two alleles can be the same or different from one another in length and can vary from one individual to the next. Microsatellite alleles are normally maintained at constant length in a given individual and its descendants; but, instability in the length of microsatellites has been observed in some tumor types (Aaltonen et al., 1993, *Science* 260:812-815; Thibodeau et al., 1993 *Science* 260:816-819; Peltomaki et al., 1993 *Cancer Research* 53:5853-5855; Ionov et al., 1993 *Nature* 363:558-561).

This type of genomic instability in tumors, termed "microsatellite instability" (MSI) is a molecular hallmark of the inherited cancer syndrome, Hereditary Nonopolyposis Colorectal Cancer (HNPCC or Lynch Syndrome). The cause of MSI is thought to include a dysfunctional DNA mismatch repair (MMR) system that fails to reverse errors occurring during DNA replication for example, through polymerase slippage (Fishel et al., 1993 *Cell* 75:1027-38; Leach et al., 1993 *Cell* 75:215-25; Bronner et al., 1994 Nature 368:258-61; Nicolaides et al., 1994 *Nature* 371:75-80; Miyaki et al., 1997 *Nat Genetics* 17:271-2). Insertion or deletion of one or more of the repetitive units in a microsatellite locus (e.g., by defective MMR) can be detected for example, by comparing allele sizes found in microsatellite locus amplified from normal and tumor DNA samples (Thibodeau et al, 1993, supra).

MSI has been found in over 90% of HNPCC and in 10-20% of sporadic colorectal tumors (Liu et al., 1996 *Nature Med* 2:169-174; Thibodeau et al., 1993, supra; Ionov et al., 1993 *Nature* 363:558-561; Aaltonen et al., 1993 *Science* 260: 812-816; Lothe et al., 1993 *Cancer Res.* 53: 5849-5852; and Boland and Goel, 2010 *Gastroenterology* 138:2073-2087. However, MSI is not limited to colorectal tumors. MSI has been detected in pancreatic cancer (Han et al., 1993 *Cancer Res* 53:5087-5089), gastric cancer (Peltomaki et al., 1993 *Cancer Res* 53:5853-5855; Mironov et al., 1994 *Cancer Res* 54:41-44), prostate cancer (Gao et al., 1994 *Oncogene* 9:2999-3003), endometrial cancer (Risinger et al., 1993 *Cancer Res* 53:5100-5103), and breast cancer (Patel et al., 1994 *Oncogene* 9:3695-3700).

Colorectal tumors with MSI-High (MSI-H) status have a distinctive molecular pathogenesis and resulting tumor features, including unusual phenotypic characteristics and hyper-mutation in the tumor genome. A sample is typically classified as MSI-H if MSI is detected for greater than 40% of tiled MS loci. Several clinical studies have shown that MSI-High (MSI-H) colorectal cancer (CRC) patients respond distinctively towards certain treatments including both chemotherapy and immunotherapy and have different prognosis than CRC patients without MSI (e.g., Microsatellite stable (MSS) patients) (see, e.g., Popat et al., *J Clin Oncol.* 2005; 23:609-618; Kim et al. *J Clin Oneal.* 2007; 25:767-772; Elsaleh et al. *Lancet.* 2000; 355:1745-1750; Storojeva et al. *Oneal Rep.* 2005; 14:241-249; Jover et al. *Gut.* 2006; 55:848-855; Des Guetz et al. *Eur J Cancer.* 2009; 45:1890-1896; Bertagnolli et al. *J Clin Oncol.* 2009; 27:1814-1821; Ribic et al. *N Engl J Med.* 2003; 349:247-257; and Benatti et al. *Clin Cancer Res.* 2005; 11:8332-8340). In 2017, the FDA approved Pembrolizumab for patients with unresectable or metastatic MSI-H or mismatch repair deficient (dMMR) solid tumors that have progressed on prior treatment. This is believed to be the first time a cancer drug has been approved based on tumor genetics rather than tissue type or tumor site. Thus, detection of the molecular alterations underlying MSI-H characteristics has implications for development of novel diagnostic and therapeutic approaches in CRC and other tumor indications.

Existing standards for the determination of MSI-H status are the Bethesda panel (Berg et al., *J Mol Diagn.* 2000; 2:20-28), which interrogates five (5) microsatellite loci recommended by the 1997 National Cancer Institute-sponsored MSI workshop (three dinucleotide and two mononucleotide repeats) and the Promega MSI Analysis System (Bacher et al. *Dis. Markers* 2004. 20(4-5):237-50), which includes 7 microsatellite loci (five mononucleotide and two pentanucleotide repeat sequences). Within these standards, instability at two or more of the MS loci determines MSI-H status. These existing standards have limitations with regards to being polymerase chain reaction (PCR) based and require manual analysis of electropherogram outputs to determine MSI or MSS status. Moreover, the standards are targeted toward tissue samples as opposed to cell-free DNA (cfDNA) samples, where the variant allele fraction for MSI loci is significantly higher in tissue samples than what is observed in cfDNA samples.

Additionally, the state of the art relies on small sets of well-known MSI loci and either the presence of a matched normal sample or manual visual analysis of electropherogram outputs to determine whether a sample is MSI. Furthermore, the state of the art is not able to identify MSI status for circulating tumor DNA (ctDNA) samples due to the lower amount of variant allele present in cfDNA samples.

BRIEF SUMMARY OF THE INVENTION

In one aspect, the disclosure generally relates to a method for detecting microsatellite instability (MSI). In some embodiments, the method for detecting MSI comprises detecting sequencing reads from a sample of human genomic DNA for a plurality of microsatellite loci; determining a metric for repeat length distribution (RLD) for each microsatellite locus; comparing the metric to a threshold value for the microsatellite locus, wherein each microsatellite has an independent threshold value; quantifying the number of microsatellite loci having an RLD metric exceeding the threshold value; and comparing the number of microsatellite loci having an RLD metric exceeding the threshold value to a microsatellite instability (MSI) proportion threshold, wherein if the number of microsatellite loci exceeds the MSI proportion threshold, the human genomic DNA from the sample has MSI. In some embodiments, the plurality of microsatellite loci are at least 10, 20, 30, 40, 50, 60, 70, 80, 90, 100, 110, 120, 130, 140, 150, 160, or more microsatellite loci selected from the group consisting of microsatellite loci: 1-170. In another embodiment, the plurality of microsatellite loci are about 5 to about 160, about 10 to about 150, about 20 to about 100, about 25 to about 80, or about 30 to about 50 microsatellite loci selected from the group consisting of microsatellite loci: 1-170 (Table 1). In yet another embodiment, the plurality of microsatellite loci correspond to loci: 1-170 (Table 1). In yet another embodiment, the plurality of microsatellite loci correspond to the loci of Table 2. In one embodiment, the plurality of microsatellite loci are at least 10, 20, 30, 40, 50, or more microsatellite loci selected from the group consisting of microsatellite loci of Table 2. In one embodiment, the plurality of microsatellite loci are about 10 to about 50, more preferably from about 20 to about 50, and most preferably between about 20 and about 40 microsatellite loci selected from the group consisting of microsatellite loci corresponding to the loci of Table 2. In some embodiments, the plurality of microsatellite loci correspond to the microsatellite loci of Table 2.

In some embodiments, the metric for repeat length distribution (RLD) is a t-statistic. In some embodiments, the metric for RLD can include a t-statistic based on mean read length of repeat units and variance of the RLD at a microsatellite locus of interest. In some embodiments, the t-statistic is determined based on the RLD of a test sample and a control RLD.

In some embodiments, the detecting sequencing reads comprises generating nucleotide sequencing reads from the human genomic DNA and identifying sequencing reads comprising a microsatellite locus by alignment of the sequencing reads to a set of microsatellite loci DNA sequences. In some embodiments, the detecting further comprises counting the number of repeat lengths for each sequencing read determined to comprise a microsatellite locus, thereby generating an RLD for each microsatellite locus.

In some embodiments, prior to generating nucleotide sequencing reads, the human genomic DNA is enriched for microsatellite loci by hybridizing the human genomic DNA to oligonucleotide probes that hybridize to microsatellite locus-containing DNA. In some embodiments, the oligonucleotides probes are in solution and the oligonucleotide probes hybridize to the microsatellite locus-containing DNA to form a hybridization complex in solution. In another embodiment, the oligonucleotides probes are bound to or attached to a solid support and the oligonucleotide probes hybridize to the microsatellite locus-containing DNA to from a hybridization complex on the solid support. In some embodiments, one or more of the oligonucleotides probes is labeled with a heterologous agent. In another embodiment, the oligonucleotide probe comprises one or more modified nucleotides. In one embodiment, the heterologous agent is a biotin or streptavidin moiety. In another embodiment, the heterologous agent is a fluorescent or chemiluminescent moiety. In some embodiments, the heterologous agent comprises at least one labeling moiety and/or at least one quencher moiety.

In some embodiments, the method comprises providing a sample having human genomic DNA. In some embodiments, the sample comprises human genomic DNA fragments. In one embodiment, fragments of human genomic DNA are prepared by mechanical, chemical or enzymatic means. In some embodiments, the human genomic DNA fragments comprise microsatellite loci. In some embodiments, the human genomic DNA fragments are contacted with a pool of oligonucleotide probes. In some embodiments, a portion of the human genomic DNA fragments contacted with the pool of oligonucleotides probes hybridize to the oligonucleotide probes to form hybridization complexes, thereby generating captured DNA. In some embodiments, the capture DNA is isolated from other cellular, polypeptide or polynucleotide components.

In some embodiments, the method further comprises providing a sample comprising the genomic DNA fragments; contacting a pool of oligonucleotide probes to the sample; capturing DNA fragments comprising microsatellite loci in hybridization complexes with the pool oligonucleotide probes, thereby generating captured DNA; separating the hybridization complexes from unbound bound nucleic acids; eluting the captured DNA from the hybridization complexes; sequencing the captured DNA eluted from the hybridization complexes; identifying sequencing reads comprising a microsatellite locus by alignment of the sequencing reads to a set of microsatellite loci DNA sequences; and counting the number of repeat lengths for each sequencing read determined to comprise a microsatellite locus, thereby generating an RLD for each microsatellite locus. In some embodiments, the genomic DNA fragments are linked to an adaptor oligonucleotide prior to contacting with the pool of oligonucleotide probes. In some embodiments, the adaptor oligonucleotide comprises one or more barcodes, universal primer binding sites, or comprise one or more barcodes and universal primer binding sites. In some embodiments, prior to sequencing, the captured DNA can be amplified with universal primers that hybridize to the universal priming binding sites.

In some embodiments, the sequencing comprises nanopore-based sequencing. In another embodiment, the sequencing comprises ion-based sequencing. In yet another embodiment, the sequencing comprises semi-conductor based sequencing.

In one embodiment, the method comprises providing a sample comprising the human genomic DNA fragments; amplifying DNA fragments comprising microsatellite loci with oligonucleotide primers specific for a microsatellite locus to produce amplicons; sequencing the amplicons; identifying sequencing reads comprising a microsatellite locus by alignment of the sequencing reads to a set of microsatellite loci DNA sequences; and counting the number of repeat lengths for each sequencing read determined to comprise a microsatellite locus, thereby generating an RLD for each microsatellite locus.

In some embodiments, the sample is a tissue sample or blood sample. In some embodiments, the sample is a blood sample such as plasma, serum and/or mononuclear peripheral cells. In some embodiments, the sample is cell-free DNA (cfDNA). In another embodiment, the sample is circulating tumor DNA (ctDNA). In one embodiment, the tissue sample is a tumor sample. In another embodiment, the sample is obtained from a human having or suspected of having a cancer. In some embodiments, the tumor sample is from a human having colorectal cancer. In some embodiments, the human has or is suspected of having HNPCC.

In some embodiments, the method further comprises treating the human with an antibody, small molecule or other compound, if the human has MSI. In some embodiments, the antibody is Pembrolizumab.

In another aspect, the disclosure generally relates to an array of oligonucleotides linked to a solid support or a heterologous agent. In some embodiments, the array comprises a set of oligonucleotides complementary over a contiguous sequence of at least 12 (or 14, 16, 18, 20) nucleotides to a microsatellite locus selected from the group consisting of microsatellites loci corresponding to loci: 1-170, wherein the set of oligonucleotides comprises at least 10, 20, 30, 40, or 50 oligonucleotides each being complementary to a different microsatellite locus corresponding to loci: 1-170. In some embodiments, each oligonucleotide in the array is linked to a separate heterologous agent. In one embodiment, the heterologous agent is biotin. In some embodiments, the set of oligonucleotides in the array are linked to the same solid support. In yet another embodiment, each oligonucleotide in the array is linked to a separate solid support.

In another aspect, the disclosure generally relates to a method of enriching for microsatellite loci in a human genomic DNA sample. In some embodiments, the method comprises hybridizing the human genomic DNA to an array of oligonucleotides linked to a solid support or heterologous agent, wherein the array comprises a set of oligonucleotides complementary over a contiguous sequence of at least 12 (or 14, 16, 18, 20) nucleotides to a microsatellite locus selected from the group consisting of microsatellites loci: 1-170, and wherein the set of oligonucleotides comprises at least 10, 20, 30, 40, or 50 oligonucleotides each being complementary to a different microsatellite locus corresponding to microsatellite loci: 1-170. In some embodiments, the method further comprises removing unhybridized genomic DNA, eluting the hybridized human genomic DNA from the array of oligonucleotides, thereby enriching for microsatellite loci.

In another aspect, the disclosure generally relates to a method for detecting MSI comprising a processor and a non-transitory computer readable medium coupled to the processor; wherein the non-transitory computer readable medium comprises code executable by the processor for performing a method to detect MSI. In some embodiments, the method comprises a processor; and a non-transitory computer readable medium coupled to the processor, the non-transitory computer readable medium comprising code executable by the processor for performing a method comprising receiving sequencing reads from human genomic DNA for a plurality of microsatellite loci; determining a repeat length distribution (RLD) for each microsatellite locus; generating a metric for the RLD for each microsatellite locus; comparing the metric for each microsatellite locus to a threshold value for the microsatellite locus, wherein each microsatellite locus has an independent threshold value; quantifying the number of detected microsatellite loci having an RLD metric exceeding the threshold value; and comparing (i) the number of microsatellite loci that have an RLD metric exceeding the threshold value to (ii) a locus set proportion threshold, wherein if the number exceeds the locus set proportion threshold, the human has microsatellite instability. In some embodiments, the method further comprises instructions for identifying sequencing reads comprising a microsatellite locus by alignment of the sequencing reads to a set of microsatellite loci DNA sequences; and instructions for counting the number of repeat lengths for each sequencing read determined to comprise a microsatellite locus, thereby generating an RLD for each microsatellite locus. In some embodiments, the metric for the RLD is a t-statistic. In some embodiments, the metric for RLD can include a t-statistic based on mean read length of repeat units and variance of the RLD at a microsatellite locus of interest. In some embodiments, the t-statistic is determined based on the RLD of a test sample and a control RLD. In some embodiments, the method further comprises at least one device configured to assay a plurality of MSI loci in a patient's sample to determine RLD for the plurality of MSI loci.

In some embodiments, the computer readable medium comprises a database comprising a listing of available therapeutic agents depending on MSI status; instructions to input the number of microsatellite loci that have an RLD metric exceeding the threshold value and to compare the number of microsatellite loci that have an RLD metric exceeding the threshold value with the locus set proportion threshold; a computer-readable program code comprising instructions to generate a report that comprises a listing of therapeutic agents for which the comparison to the locus set proportion threshold indicate a likely benefit of the at least one therapeutic agent in the database.

BRIEF DESCRIPTION OF THE DRAWINGS

FIG. 1 provides exemplary electropherogram results using the Promega MSI Analysis System with a MSI or MSS cell line.

FIG. 5A shows RLD for a single MS locus in a test sample and a normal sample that have consistent RLDs; FIG. 5B shows an MS locus having RLDs from a test sample that differ substantially to RLDs obtained from a background sample; FIG. 5C shows a MS locus having RLD variability across a normal sample.

FIG. 8 shows an exemplary system according to one embodiment of the disclosure.

DETAILED DESCRIPTION OF THE INVENTION

I. Introduction

Figure 1A:
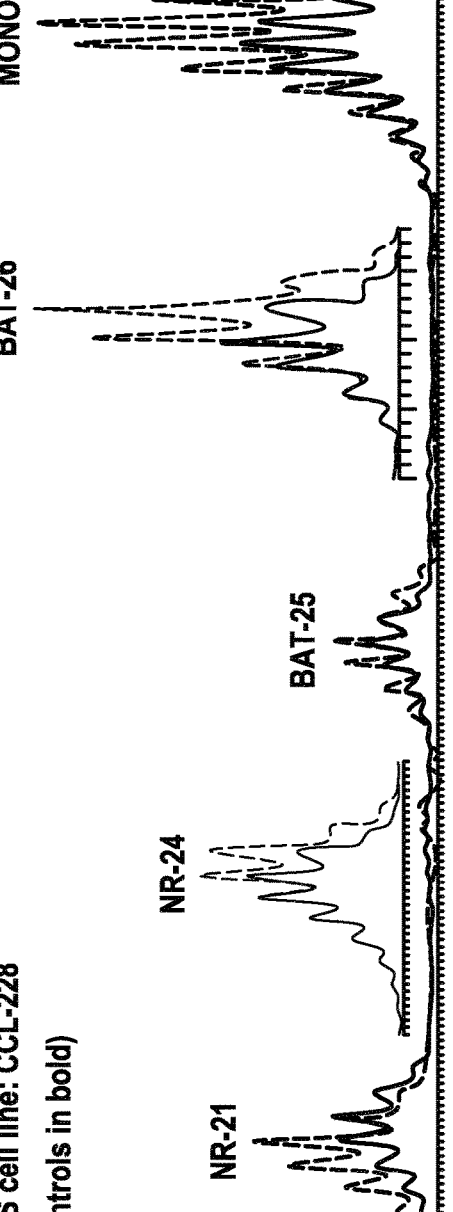
FIG. 1A shows distribution of five different MS loci (NR-21, NR-24, BAT-25, BAT-26 and MONO-27) using a MSS cell line (CCL-228). The distribution of MS loci between the test sample (MSS) and control sample, coincide.

The disclosure provides methods and systems for detecting microsatellite instability in a sample. Samples are optionally contacted with one or more oligonucleotide probes that are complementary over a contiguous sequence of (e.g., at least 12 nucleotides) to a microsatellite loci selected from microsatellite loci:1-170. Optionally, the sample contacted with the oligonucleotide capture probes is enriched for microsatellite loci by hybridizing the sample to the one or more oligonucleotide probes; removing unbound and/or unhybridized sample; and eluting the hybridizing sample from the oligonucleotide capture probes; thereby providing enriched genomic DNA having microsatellite loci.

The disclosure provides methods for detecting MSI in genomic DNA comprising detecting sequencing reads from genomic DNA having a plurality of microsatellite loci; determining a metric for repeat length distribution for each microsatellite locus, wherein each microsatellite locus has an independent threshold value; quantifying the number of microsatellite loci having an RLD metric above the threshold value; and comparing the number of microsatellite loci in excess of the threshold value to a MSI proportion threshold, wherein if the number of microsatellite loci exceeds the MSI proportion threshold, the sample is classified as MSI.

The methods and systems described herein allow for improved detection of microsatellite loci in a sample. The methods and systems described herein allow for improved sensitivity and specificity of detecting MSI in a tissue sample or plasma sample.

II. Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

The singular forms "a," "an," and "the" include plural referents unless the context clearly dictates otherwise. Thus, for example, reference to "a compound" includes a plurality of compounds.

The term "comprising" is intended to mean that the compounds, compositions and methods include the recited elements, but not excluding others. "Consisting essentially of" when used to define compounds, compositions and methods, shall mean excluding other elements that would materially affect the basic and novel characteristics of the claimed invention. "Consisting of" shall mean excluding any element, step, or ingredient not specified in the claim. Embodiments defined by each of these terms are within the scope of this disclosure.

As used herein, "Genomic DNA" or "gDNA" refers to the totality of DNA in or from a cell. Most organisms contain identical copies of genomic DNA in each cell. Fragments of gDNA are released from cells under normal cellular conditions, for example cell-free DNA, discussed herein, or can be released from tumor cells, see circulating tumor DNA, discussed herein. Additionally, gDNA can be extracted from cells, tissues, blood, plants, bacteria, etc., using commercially available kits (see, Genomic DNA Extraction Kits sold by Roche Sequencing Solutions, Pleasanton, CA, (Avenio ctDNA Analysis Kits) and Thermo Fisher Scientific (PureLink™ Genomic DNA purification Kit and Pure-Link™ Genomic DNA Mini Kit). Genomic DNA can be isolated from whole intact cells, liquid biopsies, tissues and the like.

As used herein, "cell-free DNA" or "cfDNA" refers to a fragment of genomic DNA derived from a cell that circulates in the bloodstream of a subject, which is not located within the cell. Normally, cells undergo apoptosis, necrosis and other events that result in release of genomic DNA fragments into the bloodstream. cfDNA has been utilized for various medical purposes including detection of trisomy 21 and other genetic fetal abnormalities in maternal blood and detection of donor-derived cfDNA (dd-cfDNA) to evaluate organ transplant rejection (Bloom et al., *JASN*, (2017) 28:2221-2232).

As used herein, "circulating tumor DNA" or "ctDNA" refers to a tumor-derived DNA fragment circulating in the bloodstream of a subject, which is not located within a circulating tumor cell. Circulating tumor cells generally occur when a primary tumor sheds cells that enter the bloodstream or lymphatic system. These circulating tumor cells can release fragments of their genomic DNA into the bloodstream as the tumor cell undergoes cell death, apoptosis or other events. Studies have shown that tumor DNA is released into the blood, and is present in particularly high concentrations in plasma and serum in a number of different types of cancer (Stroun et al., 1989 *Oncology* 46:318-322). Additionally, tumor DNA released into the blood has been detected by analysis of microsatellite DNA (Hibi et al., 1998 *Cancer Research* 58:1405-1407; Chen et al., 1999 *Clinical Cancer Research* 5:2297-2303; Kopreski et al., 1999 *Clinical Cancer Research* 5:1961-1965; Fujiwara et al., 1999 *Cancer Research* 59:1567-1571). Detection of microsatellite instability in tumor DNA from plasma and serum originating from head and neck squamous cell cancers (Nawroz et al., 1996 Nature Med 2:1035-1037) and small cell lung cancers (Chen et al., 1996 Nature Med 2:1033-1035) has been shown.

As used herein, a "sample" refers to a tissue or fluid obtained from a human or non-human mammalian subject. In some embodiments, a sample comprises blood, blood fractions or blood products (e.g., serum, plasma, platelets, red blood cells, peripheral blood mononuclear cells and the like); sputum or saliva; stool, urine, other biological fluids (e.g., lymph, saliva, prostatic fluid, gastric fluid, intestinal fluid, renal fluid, lung fluid, cerebrospinal fluid, and the like), tissue (e.g., kidney, lung, liver, heart, brain, nervous tissue, thyroid, eye, skeletal muscle, cartilage, or bone tissue), or cultured cells (e.g., primary cultures, explants, transformed cells, or stem cells). Such samples also include sections of tissues such as biopsy and autopsy samples, and frozen sections taken for example, for histological purposes. A sample can also include a liquid biopsy sample. A sample is typically obtained from a "subject," i.e., a eukaryotic organism, most preferably a mammal such as a primate, e.g., chimpanzee or human; cow; dog; cat; horse; sheep; goat; a rodent, e.g., guinea pig, rat, or mouse; rabbit; or a bird; reptile; or fish.

As used here, "microsatellite instability" or "(MSI)" refers to a form of genetic instability in which alleles of genomic DNA obtained from a sample (e.g., tissues, cells, or bodily fluids) change in nucleotide length at a microsatellite locus. For example, MSI can be observed upon amplification of two different samples of genomic DNA from a single subject (i.e., matched samples) such as DNA from a healthy tissue and tumor tissue, wherein the healthy (matched normal) sample produces amplified alleles of one or two different lengths and the tumor sample produces amplified alleles wherein at least one of the alleles is of a different length from the amplified alleles of the healthy sample at the same locus. Generally, MSI presents as an insertion or deletion of at least one repeat unit at a microsatellite locus.

As used herein, "microsatellite locus/loci" refers to a region of genomic DNA that contains short, repetitive sequence elements of one (1) to six (6) nucleotides in length. Each repetitive sequence is repeated one or more times within a microsatellite locus and is referred to as a "repeat unit". Microsatellite loci preferably include at least four repeat units, more preferably seven repeat units, more preferably at least ten repeat units, and most preferably at least twenty repeat units. The term "loci" is given its ordinary meaning in the art, which refers to a plurality of locus. "Locus" as used herein, refers to a unique chromosomal location defining the position of an individual gene or DNA sequence. As used herein, a "microsatellite marker" refers to a fragment of genomic DNA which includes a microsatellite locus, and optionally includes a left and right nucleic acid sequence flanking the microsatellite locus.

As used herein, an "allele" refers to one of several alternative forms of a gene or DNA sequence at a specific chromosomal location (locus). At each autosomal locus, an individual possesses two alleles, one inherited from the paternal subject and one from the maternal subject.

As used herein "amplify" and "amplifying" and derivatives thereof, refer to a process whereby multiple copies are made of a nucleic acid locus, target nucleic acid sequence, or DNA fragment. Amplification can be accomplished using essentially any nucleic acid amplification technique, including but not limited to the polymerase chain reaction (PCR) (Saiki et al. (1985) *Science* 230:1350-1354), reverse-transcription PCR (RT-PCR) (Joyce (2002) *Methods Mol Biol.* 193:83-92 and Emrich et al. (2002) *Methods Mol Biol.* 191:99-108), ligase chain reaction (LCR) (Lee (1996) *Biologicals* 24(3):197-9), polymerase ligase chain reaction (Barany et al. (1991) *PCR Methods Appl.* 1(1):5-16), Gap-LCR (Abravaya et al. (1995) *Nucleic Acids Res.* 23(4):675-82), strand displacement amplification (SDA) (Walker (1993) *PCR Methods Appl.* 3(1):1-6), linked linear amplification (LLA) (Killeen et al. (2003) *Clin Chem.* 49(7): 1050-7), rolling circle amplification (RCA) (Nilsson et al. (2002) *Nucleic Acids Res.* 30(14):e66), transcription-mediated amplification (TMA) (Emery et al. (2000) *J Clin Microbiol* 38:2688-2695), nucleic-acid-sequence-based amplification (NASBA) (Mani et al. (1999) *J Acquir Immune Defic Syndr* 22:208-209 and Berndt et al. (2000) *J Virol Methods* 89:177-181), transcription based amplification (Kwoh, D. Y., and Kwoh, T. J., *American Biotechnology Laboratory*, October, 1990) self-sustaining sequence replication (3SR) (Mueller et al. (1997) *Histochem Cell Biol* 108:431-7) and digital PCR (Dressman et al. (2003) *PNAS* 15:8817-22). PCR is a technique in which cycles of denaturation, annealing with primer, and extension with an enzyme, typically a polymerase, are used to amplify the number of copies of a target DNA or nucleic acid sequence by approximately $10^6$ times or more. The polymerase chain reaction process for amplifying nucleic acid is covered by U.S. Pat. Nos. 4,683,195 and 4,683,202, which are incorporated herein by reference for a description of the process. "Co-amplify", as used herein, refers to a process whereby multiple copies are made of two or more different loci in the same reaction mixture (e.g., same vessel, emulsion or container) in a single amplification reaction (e.g., a multiplex amplification).

As used herein, an "amplicon" refers to a molecule made by copying or transcribing another molecule. Exemplary processes in which amplicons can be produced include transcription, cloning, or a polymerase chain reaction ("PCR") or other nucleic acid amplification technique (e.g., strand displacement PCR amplification (SDA), duplex PCR amplification, rolling circle amplification, etc.). Typically, an amplicon is a copy of a selected nucleic acid sequence (e.g., a template DNA, target nucleic acid or genomic DNA fragment) or is complementary thereto.

As used herein, the term "hybridize" refers to binding between two or more components in solution or on a solid support to form a complex. Nucleic acids "hybridize" when they associate with one another. Nucleic acids hybridize due to a variety of well characterized physico-chemical forces, such as hydrogen bonding, solvent exclusion, base stacking and the like. Hybridization can occur between fully complementary nucleic acid strands or between partially complementary nucleic acid strands that include regions of mismatch. The degree of mismatch tolerated can generally be controlled by suitable adjustment of the hybridization conditions. Those skilled in the art of nucleic acid chemistry and molecular biology can determine duplex stability empirically by considering a number of variables including, e.g., the length and base pair concentration of the nucleic acids, ionic strength, and incidence of mismatched base pairs. An extensive guide to the hybridization of nucleic acids is found in Tijssen (1993) Laboratory Techniques in Biochemistry and Molecular Biology—Hybridization with Nucleic Acid Probes part I chapter 2, "Overview of principles of hybridization and the strategy of nucleic acid probe assays," (Elsevier, N.Y.), as well as in Ausubel (Ed.) Current Protocols in Molecular Biology, Volumes I, II, and III, (1997), which are each incorporated by reference. Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides, which are both incorporated herein by reference. In some aspects, hybridization can occur between a primer and a genomic DNA fragment or an oligonucleotide probe and a genomic DNA fragment.

As used herein, "monomorphic" refers to a locus of genomic DNA where only one allele pattern has been found to be present in the normal genomic DNA of all members of a population.

As used herein, "quasi-monomorphic" refers to a locus of genomic DNA where only one allele pattern has been found to be present in the normal genomic DNA of almost all members of a population. When a monomorphic or quasi-monomorphic locus, such as MONO-11 or MONO-27 is amplified, the size of the resulting amplified alleles can be compared to the most commonly observed allele size at that locus in the general population. In one embodiment, the methods disclosed herein can detect MSI tumors in a subject by amplifying two samples of genomic DNA from the same individual, wherein one of the samples obtained is from a normal, non-cancerous sample and the second sample is obtained from a cancerous (or suspected cancerous) sample.

As used herein, "oligonucleotides" or "probe" refers to a labeled or unlabeled oligonucleotide capable of hybridizing (e.g., an oligonucleotide of at least 12, 14, 16, 18, 20, or more nucleotides) to genomic DNA (e.g., human genomic DNA fragments) or target nucleic acids under suitable conditions. Typically, a probe is sufficiently complementary to a specific nucleic acid sequence contained within the genomic DNA to form a stable hybridization duplex with the genomic DNA under selected hybridization conditions. A hybridization assay carried out using the probe under sufficiently stringent hybridization conditions permits selective detection of a specific nucleic acid sequence, such as a mutant form or variant of the nucleic acid sequence. The term "hybridizing region" refers to a region of the probe that is exactly or substantially complementary to, and therefore hybridizes to, the genomic DNA or target nucleic acid. Although the hybridizing region can refer to the entire oligonucleotide, the probe may include additional nucleotide sequences that function, for example, as linker binding sites to provide a site for attaching the probe sequence to a solid support or the like. In certain embodiments, a probe is included in a nucleic acid molecule that comprises one or more labels (e.g., a reporter dye, a quencher moiety, etc.), such as a 5'-nuclease probe, a FRET probe, a molecular beacon, or the like, which can be utilized to detect dissociation of the probe from target nucleic acids in a sample. In some embodiments, the hybridizing region of the probe is completely complementary to the target nucleic acid. However, in general, complete complementarity is not necessary (i.e., nucleic acids can be partially complementary to one another); stable duplexes may contain limited mismatched bases or unmatched bases. Modification of the stringency conditions may be necessary to permit a stable hybridization duplex with one or more base pair mismatches or unmatched bases. Sambrook et al., Molecular Cloning: A Laboratory Manual, 3rd Ed., Cold Spring Harbor Laboratory Press, Cold Spring Harbor, N.Y. (2001), which is incorporated by reference, provides guidance for suitable modification. Stability of the duplex depends on a number of variables including length of the target nucleic acid, base composition of the target nucleic acid (e.g., GC content) and sequence of the oligonucleotide probe, temperature, and ionic conditions. One of ordinary skill in the art will recognize that, in general, the exact complement of a given oligonucleotide probe is similarly useful as a probe. One of ordinary skill in the art will also recognize that, in certain embodiments, oligonucleotide probes can also be used as primers.

As used herein, a "primer" refers to a single-stranded oligonucleotide or DNA fragment which hybridizes to a strand of target DNA (e.g., genomic DNA) in such a manner that the 3' terminus of the primer can act as a site of polymerization in the presence of a DNA polymerase enzyme. A "primer pair" refers to a pair of primers which hybridize to opposite strands of a target DNA molecule (e.g., genomic DNA fragment), which flank a nucleotide region to be amplified. Typically, a "primer binding site" refers to an area of the target DNA to which a primer or primer pair hybridizes. A "locus-specific" primer or "target-specific" primer refers to a primer that specifically hybridizes with a portion of the stated locus or its complementary strand, at least for one allele of the locus, and does not hybridize efficiently with other DNA sequences under the conditions used in the amplification method. Conversely, a "universal primer" refers to a primer that is designed to maximize random amplification of regions of the DNA present in the sample without being targeted to a target-specific or loci-specific region of the DNA. Generally, universal primers contain a random nucleic acid sequence of between about 6 and about 12 nucleotides in length, with the intent that the universal primer sequence efficiently hybridizes under the selected hybridization conditions to a plurality of locations within the genomic DNA or select nucleic acid molecules possessing the random nucleic acid sequence (e.g., an adaptor oligonucleotide).

As used herein, the terms "identical" or "percent identity" in the context of two or more nucleic acid sequences refers to two or more sequences that are the same or have a specified percentage of nucleotides that are the same (i.e., % identical), when compared and aligned for maximum correspondence, e.g., as measured using one of the sequence comparison algorithms or by visual inspection. An exemplary algorithm that is suitable sequence alignment and for determining percent sequence identity and sequence similarity is the BLAST program, which are described in Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:113-141, Altschul et al. (1997) "Gapped BLAST and PSI-BLAST: a new generation of protein database search programs" *Nucleic Acids Res.* 25:3389-3402, and Zhang et al. (1997) "Power-BLAST: A new network BLAST application for interactive or automated sequence analysis and annotation" *Genome Res.* 7:649-656, each of which is incorporated herein by reference in its entirety.

Percent identity between two nucleic acid sequences is generally calculated using standard default parameters of the various methods or computer programs. A high degree of sequence identity, as used herein, between two nucleic acid molecules is typically between about 90% identity and 100% identity, for example, about 90% identity or higher, preferably about 95% identity or higher, more preferably about 98% identity or higher. A moderate degree of sequence identity, as used herein, between two nucleic acid molecules is typically between about 80% identity to about 85% identity, for example, about 80% identity or higher, preferably about 85% identity. A low degree of sequence identity, as used herein, between two nucleic acid molecules is typically between about 50% identity and 75% identity, for example, about 50% identity, preferably about 60% identity, more preferably about 75% identity.

As used herein, "an array" refers to a plurality of oligonucleotides spotted or in-situ synthesized on a surface such as, but not limited to, glass or beads. A DNA array typically comprises a plurality of oligonucleotide probes spotted onto a surface in a random or ordered manner. The oligonucleotide probes hybridize to complementary nucleic acid sequences present in a sample under high stringency conditions. Hybridization can be detected and/or quantified by a variety of means including fluorophore or chemiluminescence.

As used herein, "heterologous agent" refers to an agent not naturally found in combination with a nucleic acid molecule. In one embodiment, the heterologous agent can be derived from a different organism (e.g., an antibody from a goat or mouse attached to a nucleic acid molecule from a human) In another embodiment, a heterologous agent can include a label, such as but not limited to, FAM or $^{32}$P. In this example, FAM or $^{32}$P are artificially linked, conjugated, bound, attached, or otherwise associated with the nucleic acid molecule. In yet another embodiment, the heterologous agent can include biotin (e.g., biotinylation of a nucleic acid). Biotin binds to streptavidin and avidin with high affinity and specificity and these interactions can be exploited to isolate biotinylated nucleic acid molecules from other components.

As used herein, "Repeat Length Distribution" or "RLD" for a locus refers to a distribution of repeat units for the sequencing reads that cover the locus (e.g., as determined based on alignment of a read or electropherograms). An RLD for a locus can be defined as a histogram (i.e., a value for each length in a range of lengths), where the value for each length corresponds to the number of sequencing reads having that particular length of repeat units. The RLD is determined by analysis of sequencing reads obtained from a sample containing the microsatellite locus. Sequence reads containing the microsatellite locus can be aligned against a reference genome (e.g., hg38 (Human Genome version 38), a sample lacking repeat units at the microsatellite locus, or a sample having a known number of repeat units at the microsatellite locus). From alignment of a sequencing read to a microsatellite locus of interest, the number of repeat units present in the sequencing read can be determined. If a single molecule technique is used (or at least a full sequence stretching across the microsatellite locus), the number of repeat units can be determined directly from a sequencing read, after it has been aligned to a particular locus. It will be appreciated that alignment of sequencing reads, amplification of genomic DNA fragments, or other manipulations/ steps can introduce one or more errors into a sequencing read, which may appear as a repeat unit or may affect alignment of a sequencing read against a reference genome. For example, the RLD for loci: 1 (see, Table 1) is typically observed in MSS (e.g., non-cancerous) cells to be from about 13 repeat units to about 22 repeat units.

As used herein, "metric" refers to a standard of measurement. In one embodiment, a metric for RLD is determined, e.g., based on a comparison to a reference RLD. The metric for an RLD can include one or more statistical analyses to appropriately represent the RLD. In some embodiments, the metric for RLD is a t-statistic such as Student's t-test or Wilcox-Rank test. Thus, an RLD can be represented by one or more statistical values, and these statistical value(s) of a sample RLD of a first locus can be compared to corresponding statistical value(s) of a reference RLD. In some embodiments, the metric is one or more summarized statistics of the RLD. Examples of such a statistic include: mean, variance, skewness, kurtosis, etc. In other embodiments, the metric is a similarity measure between the RLD of a tested sample and a control RLD. Examples include: t-statistic, chi-square statistic, Kolmogorov-Smirnov statistic, Kullback-Leibler divergence, correlation distance, cosine distance, Euclidean distance, Manhattan distance, etc. In some embodiments, the t-statistic is determined based on the RLD of a test sample and a control RLD. Generally, a metric for RLD is obtained for each microsatellite locus under evaluation. Such a distance metric can be based on differences or ratios between the raw values of the sample RLD and the reference RLD, e.g., differences between probabilities, as may be determined based on normalizing numbers of reads having given repeat lengths, where the normalization may use a total number of reads in a given measurement. Another example of normalization can be based on a total area of a histogram, e.g., determined as an electropherogram.

As used herein, a "nanopore," refers to a pore, channel, or passage formed or otherwise provided in a membrane or other barrier material that has a characteristic width or diameter of about 0.1 nm to about 1000 nm. A nanopore can be made of a naturally-occurring pore-forming protein, such as α-hemolysin from *S. aureus*, or a mutant or variant of a wild-type pore-forming protein, either non-naturally occurring (i.e., engineered) such as α-HL-C46, or naturally occurring. A membrane may be an organic membrane, such as a lipid bilayer, or a synthetic membrane made of a non-naturally occurring polymeric material. The nanopore may be disposed adjacent or in proximity to a sensor, a sensing circuit, or an electrode coupled to a sensing circuit, such as, for example, a complementary metal-oxide semiconductor (CMOS) or field effect transistor (FET) circuit. As such, nanopores can be used to sequence nucleic acid sequences of interest (see, US Patent Publication No.: 20100331194; 20140019064; 20150176071; 20160281159; and 20170016048).

As used herein, a "solid support" refers to a solid material that can be derivatized with, or otherwise attached to, a chemical moiety, such as an oligonucleotide probe or the like. Exemplary solid supports include plates, beads, microbeads, tubes, fibers, whiskers, combs, hybridization chips (including microarray substrates, such as those used in GeneChip™ probe arrays (Affymetrix, Inc., Santa Clara, Calif., USA), membranes, single crystals, ceramic layers, self-assembling monolayers, and the like.

The term "cancer" refers to a disease characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; cervical cancer, uterine cancer, renal cancer; cancer of the central nervous system; skin cancer (e.g., melanoma); lymphomas; gliomas; choriocarcinomas; head and neck cancers; osteogenic sarcomas; and blood cancers. As used herein, a "tumor" comprises one or more cancerous cells. In some embodiments, the cancer is colon or colorectal cancer.

The term "agent" refers to any molecule, either naturally occurring or synthetic, e.g., peptide, protein, oligopeptide (e.g., from about 5 to about 25 amino acids in length, e.g., about 5, 10, 15, 20, or 25 amino acids in length), small organic molecule (e.g., an organic molecule having a molecular weight of less than about 2500 daltons, e.g., less than 2000, less than 1000, or less than 500 daltons), circular peptide, peptidomimetic, antibody, polysaccharide, lipid, fatty acid, inhibitory RNA (e.g., siRNA, shRNA or sgRNA), polynucleotide, oligonucleotide, aptamer, and drug compound. Typically, the agent is intended to have a therapeutic effect on the subject to whom the agent is administered. In some cases, the agent can include an immune checkpoint inhibitor, such as Pembrolizumab.

As used herein, the terms "treatment," "treating," and "treat" refer to any indicia of success in the treatment or amelioration of an injury, disease, or condition, including any objective or subjective parameter such as abatement; remission; diminishing of symptoms or making the injury, disease, or condition more tolerable to the subject; slowing in the rate of degeneration or decline; making the final point of degeneration less debilitating; and/or improving a subject's physical or mental well-being.

The term "pharmaceutical composition" refers to a composition suitable for administration to a subject. Typically, the pharmaceutical composition comprises an agent. In general, a pharmaceutical composition is sterile, and preferably free of contaminants that are capable of eliciting an undesirable response in the subject. Pharmaceutical compositions can be designed for administration to subjects in need thereof via a number of different routes of administration, including oral, intravenous, buccal, rectal, parenteral, intraperitoneal, intradermal, intratracheal, intramuscular, subcutaneous, inhalational, and the like.

A "therapeutic amount" or "therapeutically effective amount" of an agent (e.g., an agent that treats cancer) is an amount of the agent which prevents, alleviates, abates, or reduces the severity of symptoms of cancer in a subject.

The terms "administer," "administered," or "administering" refer to methods of delivering agents to the desired site of biological action. These methods include, but are not limited to, topical delivery, parenteral delivery, intravenous delivery, intradermal delivery, intramuscular delivery, colonical delivery, rectal delivery, or intraperitoneal delivery. Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, PA.

III. Detection Methods

In one aspect, methods of detecting MSI in a sample and/or subject are provided. In some embodiments, the methods described relate to detecting MSI in a subject having or suspected of having cancer. In another aspect, methods relate to detecting a set of microsatellite loci in a sample, where the set of microsatellite loci are associated with MSI-tumors. The methods disclosed herein provide identification and/or quantification of genomic DNA fragments in a sample from a subject, e.g., by NGS, particularly when the genomic DNA fragments are present in low abundance (e.g., ctDNA). The described methods ensure accurate detection and quantitation of microsatellite loci in clinical samples (e.g., patient samples), which can be negatively impacted if the genomic DNA fragments are inaccurately normalized or quantified. Additionally, the methods provided herein can be used to increase the yield of the genomic DNA fragments having microsatellite loci through the use of oligonucleotide probes (e.g., selective enrichment) that may be optionally attached to a solid support.

Figure 2:
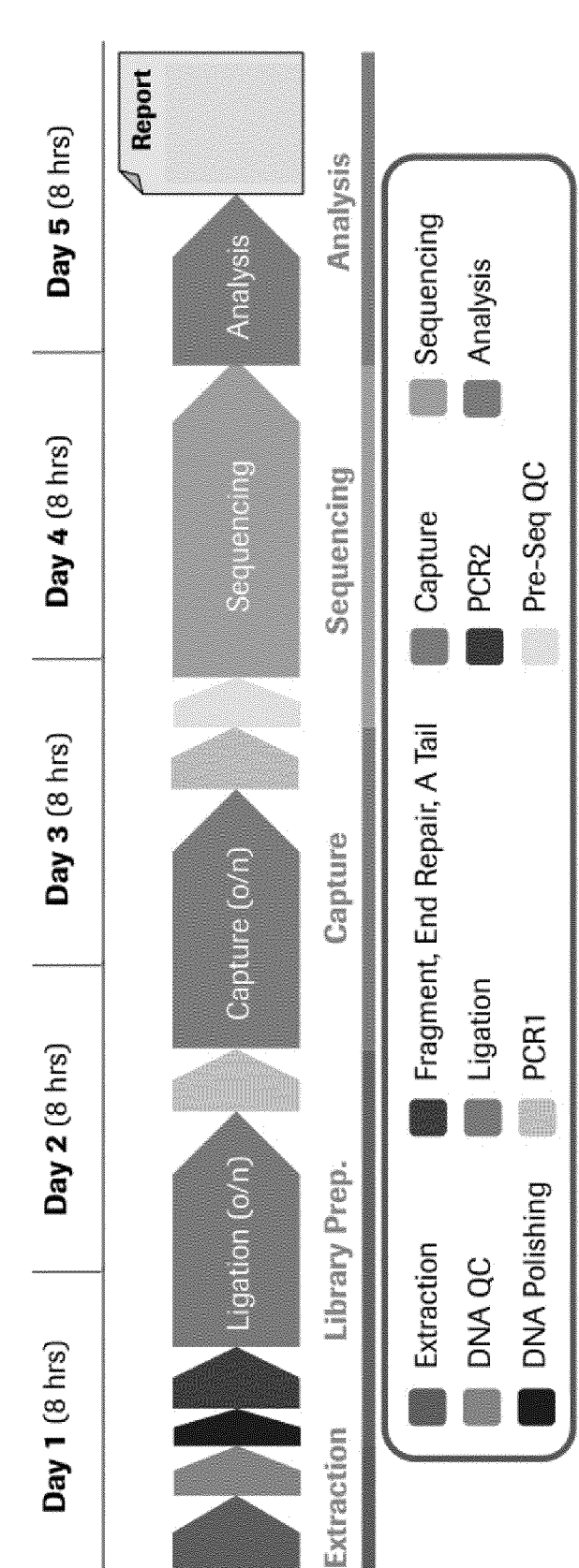
FIG. 2 provides an exemplary workflow of one embodiment of the disclosure.

As described herein, it has been found that detection of a plurality of microsatellite loci in a sample, as compared to a predetermined threshold, can be predictive of MSI in the subject from whom the sample was obtained. Generally, the methods comprise detecting sequencing reads from human genomic DNA for a plurality of microsatellite loci. An exemplary workflow for detecting MSI in a sample is set forth in FIG. 2. It will be readily apparent that some steps within the workflow of FIG. 2 may be omitted and/or repeated, for example, if the sample has been previously purified and prepared for sequencing.

In some embodiments, the samples is a blood sample, cell-free DNA, or a tissue sample. In one embodiment, the sample is a blood draw or liquid biopsy. In one embodiment, the sample is a tumor tissue sample. In some embodiments, the subject is a human and the human is suspected of having or has cancer. In one embodiment, the cancer is colorectal cancer. In some embodiments, the subject is treated with one or more therapeutic agents used to treat cancer. In one embodiment, the therapeutic agent is Pembrolizumab.

In one aspect, the disclosure generally relates to methods for detecting MSI, the method comprising (1) detecting sequencing reads from human genomic DNA for a plurality of microsatellite loci; (2) determining a metric for repeat length distribution (RLD) for each microsatellite locus; (3) comparing the metric to a threshold value for the microsatellite locus, wherein each microsatellite has an independent threshold value; (4) quantifying the number of microsatellite loci having an RLD metric exceeding the threshold value; and (5) comparing the number of microsatellite loci having an RLD metric exceeding the threshold value to a microsatellite instability (MSI) proportion threshold, wherein if the number exceeds the MSI proportion threshold, the human has microsatellite instability.

In some embodiments, the detecting comprises generating nucleotide sequencing reads from the genomic DNA and identifying sequencing reads comprising a microsatellite locus by alignment of the sequencing reads to a set of microsatellite loci DNA sequences; and counting the number of repeat lengths for each sequencing read determined to comprise a microsatellite locus, thereby generating an RLD for each microsatellite locus.

In one embodiment, prior to generating the nucleotide sequencing reads, the genomic DNA is enriched for microsatellite loci by hybridizing the genomic DNA to oligonucleotide probes that hybridize to microsatellite locus-containing DNA. In some embodiments, the enriched genomic DNA is washed to remove unbound or non-specific nucleic acids.

In one embodiment, the metric for RLD is a t-statistic. In some embodiments, the metric for RLD can include a t-statistic based on mean read length of repeat units and variance of the RLD at a microsatellite locus of interest. In some embodiments, the t-statistic is determined based on the RLD of a test sample and a control RLD.

In one embodiment, the plurality of microsatellite loci comprises a set of microsatellite loci, wherein the set of microsatellite loci is selected from the group of microsatellite loci corresponding to loci: 1-170 (see, Table 1). In some embodiments, the set of microsatellite loci is selected from at least 58 microsatellite loci corresponding to the group of microsatellite loci corresponding to microsatellite loci: 1-64. In some embodiments, the set of microsatellite loci comprises the microsatellite loci of Table 2 (i.e., loci 1-4, 6-9, 11-21, 23, 25-29, 31-48 and 50-64 of Table 1). In another embodiment, the set of microsatellite loci is selected from 10 or more microsatellite loci selected from the group of microsatellite loci corresponding to loci: 1-64. In some embodiments, the set of microsatellite loci is at least 10, 20, 30, 40, 50, 60, 70, 80, 90, 100, 110, 120, 130, 140, 150, 160, or more, microsatellite loci selected from the group of microsatellite loci corresponding to loci: 1-170. In another embodiment, the set of microsatellite loci is at least 10, 20, 30, 40, or 50 microsatellite loci selected from the group of microsatellite loci corresponding to loci: 1-64. In one embodiment, the plurality of microsatellite loci is the group of microsatellite loci corresponding to Table 2.

In some embodiments, the plurality of microsatellite loci are selected from genomic coordinates present in one or more chromosomes of the human genome. In another embodiment, the plurality of microsatellite loci are selected from one or more of the following genomic coordinates of microsatellite locus as recited in human genome 38 (hg38):

TABLE 1

| 170 Microsatellite loci | | | |
| --- | --- | --- | --- |
| locus | location | coordinate | coordinate |
| 1 | chr1 | 32936733 | 32936750 |
| 2 | chr1 | 46859627 | 46859640 |

TABLE 1-continued

170 Microsatellite loci

| locus | location | coordinate | coordinate |
|---|---|---|---|
| 3 | chr1 | 149929093 | 149929109 |
| 4 | chr1 | 235344151 | 235344170 |
| 5 | chr2 | 5699709 | 5699727 |
| 6 | chr2 | 5700420 | 5700434 |
| 7 | chr2 | 14638213 | 14638234 |
| 8 | chr2 | 39309548 | 39309575 |
| 9 | chr2 | 47414420 | 47414447 |
| 10 | chr2 | 51061373 | 51061415 |
| 11 | chr2 | 66435743 | 66435767 |
| 12 | chr2 | 95183613 | 95183636 |
| 13 | chr2 | 98998132 | 98998145 |
| 14 | chr2 | 102762122 | 102762138 |
| 15 | chr2 | 129982139 | 129982152 |
| 16 | chr2 | 173266783 | 173266800 |
| 17 | chr3 | 70959190 | 70959203 |
| 18 | chr3 | 123614028 | 123614044 |
| 19 | chr4 | 39500102 | 39500120 |
| 20 | chr4 | 54732045 | 54732070 |
| 21 | chr4 | 151662755 | 151662771 |
| 22 | chr5 | 112877981 | 112878021 |
| 23 | chr5 | 140115261 | 140115276 |
| 24 | chr5 | 181260427 | 181260439 |
| 25 | chr6 | 11714406 | 11714420 |
| 26 | chr7 | 1747883 | 1747900 |
| 27 | chr7 | 143306249 | 143306274 |
| 28 | chr8 | 33498673 | 33498689 |
| 29 | chr8 | 40154248 | 40154264 |
| 30 | chr8 | 58148166 | 58148186 |
| 31 | chr8 | 93925321 | 93925334 |
| 32 | chr9 | 84003046 | 84003063 |
| 33 | chr9 | 126837838 | 126837854 |
| 34 | chr10 | 21518540 | 21518553 |
| 35 | chr10 | 119137173 | 119137195 |
| 36 | chr11 | 5666090 | 5666107 |
| 37 | chr11 | 115176312 | 115176326 |
| 38 | chr11 | 125620870 | 125620891 |
| 39 | chr11 | 125893715 | 125893728 |
| 40 | chr12 | 84892141 | 84892158 |
| 41 | chr12 | 130399009 | 130399022 |
| 42 | chr13 | 50013518 | 50013540 |
| 43 | chr14 | 23183137 | 23183158 |
| 44 | chr14 | 64523982 | 64523995 |
| 45 | chr14 | 73492999 | 73493015 |
| 46 | chr16 | 19118464 | 19118481 |
| 47 | chr16 | 29669203 | 29669217 |
| 48 | chr16 | 58543411 | 58543424 |
| 49 | chr17 | 38995870 | 38995910 |
| 50 | chr18 | 649879 | 649894 |
| 51 | chr19 | 11808381 | 11808396 |
| 52 | chr19 | 21378606 | 21378625 |
| 53 | chr19 | 57257698 | 57257723 |
| 54 | chr19 | 57258437 | 57258450 |
| 55 | chr19 | 57262350 | 57262363 |
| 56 | chr20 | 59922426 | 59922441 |
| 57 | chr21 | 34103315 | 34103331 |
| 58 | chrX | 2904903 | 2904920 |
| 59 | chrX | 38805564 | 38805577 |
| 60 | chrX | 101413944 | 101413957 |
| 61 | chrX | 102154282 | 102154298 |
| 62 | chrX | 102658669 | 102658683 |
| 63 | chrX | 102751949 | 102751969 |
| 64 | chrX | 145825169 | 145825191 |
| 65 | chr1 | 103663067 | 103663077 |
| 66 | chr1 | 103757205 | 103757215 |
| 67 | chr1 | 116112562 | 116112575 |
| 68 | chr1 | 13782253 | 13782262 |
| 69 | chr1 | 150714123 | 150714133 |
| 70 | chr1 | 151224226 | 151224235 |
| 71 | chr1 | 159062696 | 159062706 |
| 72 | chr1 | 200624913 | 200624921 |
| 73 | chr1 | 221702319 | 221702330 |
| 74 | chr1 | 236897645 | 236897660 |
| 75 | chr1 | 28459218 | 28459228 |
| 76 | chr1 | 52784862 | 52784872 |
| 77 | chr1 | 88983825 | 88983836 |
| 78 | chr10 | 72893710 | 72893720 |

TABLE 1-continued

170 Microsatellite loci

| locus | location | coordinate | coordinate |
|---|---|---|---|
| 79 | chr11 | 105007313 | 105007323 |
| 80 | chr11 | 105008959 | 105008969 |
| 81 | chr11 | 120479927 | 120479935 |
| 82 | chr11 | 63382198 | 63382209 |
| 83 | chr11 | 65501008 | 65501020 |
| 84 | chr12 | 118150956 | 118150974 |
| 85 | chr12 | 119728455 | 119728465 |
| 86 | chr12 | 13211492 | 13211502 |
| 87 | chr12 | 31282674 | 31282685 |
| 88 | chr12 | 54011395 | 54011406 |
| 89 | chr12 | 96286155 | 96286166 |
| 90 | chr13 | 46771334 | 46771348 |
| 91 | chr13 | 49350729 | 49350739 |
| 92 | chr13 | 57725300 | 57725311 |
| 93 | chr14 | 19668967 | 19668978 |
| 94 | chr14 | 53046721 | 53046733 |
| 95 | chr15 | 30113885 | 30113899 |
| 96 | chr15 | 37099551 | 37099563 |
| 97 | chr15 | 41852769 | 41852780 |
| 98 | chr15 | 72572067 | 72572077 |
| 99 | chr16 | 14889234 | 14889243 |
| 100 | chr17 | 1423460 | 1423474 |
| 101 | chr17 | 4539344 | 4539362 |
| 102 | chr17 | 45539269 | 45539279 |
| 103 | chr17 | 46306192 | 46306202 |
| 104 | chr17 | 46523767 | 46523777 |
| 105 | chr17 | 56938993 | 56939007 |
| 106 | chr17 | 58357799 | 58357806 |
| 107 | chr18 | 23529756 | 23529766 |
| 108 | chr18 | 319944 | 319955 |
| 109 | chr18 | 33333178 | 33333188 |
| 110 | chr18 | 9954236 | 9954249 |
| 111 | chr19 | 12463926 | 12463947 |
| 112 | chr19 | 13993876 | 13993890 |
| 113 | chr19 | 44158121 | 44158134 |
| 114 | chr19 | 9251064 | 9251075 |
| 115 | chr2 | 106426090 | 106426102 |
| 116 | chr2 | 108729222 | 108729232 |
| 117 | chr2 | 118096518 | 118096531 |
| 118 | chr2 | 147926116 | 147926124 |
| 119 | chr2 | 151379531 | 151379545 |
| 120 | chr2 | 182942165 | 182942175 |
| 121 | chr2 | 196666794 | 196666805 |
| 122 | chr2 | 202300378 | 202300388 |
| 123 | chr2 | 210315041 | 210315052 |
| 124 | chr2 | 55234233 | 55234243 |
| 125 | chr2 | 63842143 | 63842158 |
| 126 | chr2 | 87757451 | 87757462 |
| 127 | chr2 | 8858645 | 8858657 |
| 128 | chr20 | 53875234 | 53875245 |
| 129 | chr20 | 60012728 | 60012738 |
| 130 | chr21 | 28966883 | 28966894 |
| 131 | chr21 | 32601784 | 32601798 |
| 132 | chr22 | 38683915 | 38683930 |
| 133 | chr3 | 101459057 | 101459067 |
| 134 | chr3 | 113658634 | 113658645 |
| 135 | chr3 | 131014202 | 131014213 |
| 136 | chr3 | 165187860 | 165187871 |
| 137 | chr3 | 170997894 | 170997904 |
| 138 | chr3 | 25719646 | 25719656 |
| 139 | chr3 | 30650379 | 30650389 |
| 140 | chr3 | 51380172 | 51380179 |
| 141 | chr5 | 159099526 | 159099541 |
| 142 | chr5 | 162067984 | 162067996 |
| 143 | chr5 | 177302735 | 177302747 |
| 144 | chr5 | 58974630 | 58974642 |
| 145 | chr5 | 68288684 | 68288696 |
| 146 | chr5 | 78450039 | 78450050 |
| 147 | chr5 | 80675095 | 80675103 |
| 148 | chr5 | 83641432 | 83641442 |
| 149 | chr5 | 88722571 | 88722584 |
| 150 | chr6 | 167040031 | 167040043 |
| 151 | chr6 | 43054238 | 43054250 |
| 152 | chr6 | 49492281 | 49492291 |
| 153 | chr6 | 55874913 | 55874927 |
| 154 | chr6 | 70861991 | 70862003 |

TABLE 1-continued

170 Microsatellite loci

| locus | location | coordinate | coordinate |
| --- | --- | --- | --- |
| 155 | chr6 | 88143811 | 88143822 |
| 156 | chr7 | 135619945 | 135619955 |
| 157 | chr7 | 30633896 | 30633911 |
| 158 | chr7 | 54752300 | 54752311 |
| 159 | chr7 | 75193019 | 75193032 |
| 160 | chr7 | 95359943 | 95359960 |
| 161 | chr8 | 23854553 | 23854565 |
| 162 | chr8 | 33499307 | 33499320 |
| 163 | chr8 | 39103749 | 39103760 |
| 164 | chr8 | 7489344 | 7489353 |
| 165 | chr8 | 7822205 | 7822214 |
| 166 | chr8 | 78717503 | 78717517 |
| 167 | chr9 | 107331689 | 107331701 |
| 168 | chr9 | 83969307 | 83969318 |
| 169 | chrX | 101883466 | 101883477 |
| 170 | chrX | 18164977 | 18164992 |

TABLE 2

58 Microsatellite loci (subset of 170 loci)

| Chr. | Coordinate | Coordinate |
| --- | --- | --- |
| chr1 | 149929093 | 149929109 |
| chr1 | 235344151 | 235344170 |
| chr1 | 32936733 | 32936750 |
| chr1 | 46859627 | 46859640 |
| chr10 | 119137173 | 119137195 |
| chr10 | 21518540 | 21518553 |
| chr11 | 115176312 | 115176326 |
| chr11 | 125620870 | 125620891 |
| chr11 | 125893715 | 125893728 |
| chr11 | 5666090 | 5666107 |
| chr12 | 130399009 | 130399022 |
| chr12 | 84892141 | 84892158 |
| chr13 | 50013518 | 50013540 |
| chr14 | 23183137 | 23183158 |
| chr14 | 64523982 | 64523995 |
| chr14 | 73492999 | 73493015 |
| chr16 | 19118464 | 19118481 |
| chr16 | 29669203 | 29669217 |
| chr16 | 58543411 | 58543424 |
| chr18 | 649879 | 649894 |
| chr19 | 11808381 | 11808396 |
| chr19 | 21378606 | 21378625 |
| chr19 | 57257698 | 57257723 |
| chr19 | 57258437 | 57258450 |
| chr19 | 57262350 | 57262363 |
| chr2 | 102762122 | 102762138 |
| chr2 | 129982139 | 129982152 |
| chr2 | 14638213 | 14638234 |
| chr2 | 173266783 | 173266800 |
| chr2 | 39309548 | 39309575 |
| chr2 | 47414420 | 47414447 |
| chr2 | 5700420 | 5700434 |
| chr2 | 66435743 | 66435767 |
| chr2 | 95183613 | 95183636 |
| chr2 | 98998132 | 98998145 |
| chr20 | 59922426 | 59922441 |
| chr21 | 34103315 | 34103331 |
| chr3 | 123614028 | 123614044 |
| chr3 | 70959190 | 70959203 |
| chr4 | 151662755 | 151662771 |
| chr4 | 39500102 | 39500120 |
| chr4 | 54732045 | 54732070 |
| chr5 | 140115261 | 140115276 |
| chr6 | 11714406 | 11714420 |
| chr7 | 143306249 | 143306274 |
| chr7 | 1747883 | 1747900 |
| chr8 | 33498673 | 33498689 |
| chr8 | 40154248 | 40154264 |
| chr8 | 93925321 | 93925334 |
| chr9 | 126837838 | 126837854 |

TABLE 2-continued

58 Microsatellite loci (subset of 170 loci)

| Chr. | Coordinate | Coordinate |
| --- | --- | --- |
| chr9 | 84003046 | 84003063 |
| chrX | 101413944 | 101413957 |
| chrX | 102154282 | 102154298 |
| chrX | 102658669 | 102658683 |
| chrX | 102751949 | 102751969 |
| chrX | 145825169 | 145825191 |
| chrX | 2904903 | 2904920 |
| chrX | 38805564 | 38805577 |

In some embodiments, the plurality of microsatellite loci comprise mono-, di- tri-, tetra-, penta- or hexa-nucleotide repeat units. In one embodiment, the plurality of microsatellite loci comprise mono-, di- and/or tri-nucleotide repeat units (e.g., $(A_{17})$, $(T_{14})$, $(AC_{21})$, $(TG_{20})$ $(TCT_6)$. In some embodiments, the repeat unit length determined from a sequencing read, where the sequencing read is a proxy for the cell, will be between about 2 and about 100 repeat units, about 5 and about 80 repeat units, about 10 and about 60 repeat units, and about 15 to about 40 repeat units.

In some embodiments, the method comprises (1) providing a sample comprising the human genomic DNA fragments; (2) contacting a pool of oligonucleotide probes to the sample; (3) capturing DNA fragments comprising microsatellite loci in hybridization complexes with the pool oligonucleotide probes, thereby generating captured DNA; (4) separating the hybridization complexes from unbound nucleic acids; (5) eluting the captured DNA from the hybridization complexes; (6) sequencing the captured DNA eluted from the hybridization complexes; (7) identifying sequencing reads comprising a microsatellite locus by alignment of the sequencing reads to a set of microsatellite loci DNA sequences; and (8) counting the number of repeat lengths for each sequencing read determined to comprise a microsatellite locus, thereby generating an RLD for each microsatellite locus.

In some embodiments, prior to contacting the pool of oligonucleotide probes with the sample, adaptor oligonucleotides are linked, attached or ligated to the human genomic fragments. In one embodiment, the adaptor oligonucleotides comprise one or more barcodes, universal primer binding sites, or comprise one or more barcodes and universal primer binding sites. In some embodiments, the adaptor oligonucleotides are linked to both the 3' and 5' end of the genomic DNA fragments to form blunt-ended double-stranded genomic DNA fragments. The adaptor oligonucleotides having a universal primer binding site can be used in a subsequent amplification step to amplify the adaptor sequences ligated to the genomic DNA fragments.

In some embodiments, prior to sequencing, the captured DNA is amplified with universal primers that hybridize to universal primer binding sites present in the adaptor oligonucleotides.

In some embodiments, the sequencing is nanopore-based sequencing.

In another embodiment, the method comprises (1) providing a sample comprising human genomic DNA fragments; (2) amplifying DNA fragments comprising microsatellite loci with oligonucleotide primers specific for a microsatellite locus contacting a pool of oligonucleotide probes to the sample to produce amplicons; (3) sequencing the amplicons; (4) identifying sequencing reads comprising a microsatellite locus by alignment of the sequencing reads to a set of microsatellite loci DNA sequences; and (5)

counting the number of repeat lengths for each sequencing read determined to comprise a microsatellite locus, thereby generating an RLD for each microsatellite locus.

DNA Extraction

Generally, any method of DNA extraction may be used to isolate genomic DNA or genomic DNA fragments for use with the invention. In a preferred embodiment, genomic DNA is extracted from tissues, cells, liquid biopsy samples, blood or plasma samples using solution-based or solid-phase based DNA extraction techniques. Genomic DNA extraction can include detergent-based cell lysis, denaturation of nucleoproteins, and optionally removal of contaminants. For example, solution based DNA extraction methods can include but are not limited to salting out methods or organic solvent/chaotrope methods; while solid-phase DNA extraction methods can include but are not limited to silica resin methods, anion exchange methods or magnetic beads (see, e.g., Chacon-Cortes and Griffiths *J. Biorepository Sci App Med.*, (2014) 2:1-9).

Typically, DNA is extracted from a sample through a process of steps or manipulations.

Generally, the sample is treated with a lysis agent to lyse intact cells present in the sample. DNA released from the lysed cells can be bound to a solid support, column or membrane where it may undergo one or more washing steps to remove non-DNA components such as contaminants and/or proteins from the sample. Finally, the bound DNA can be released from the solid support, column or membrane and stored in an appropriate buffer until ready for further processing.

In some embodiments, genomic DNA can be sheared or fragmented into smaller genomic DNA fragments for example by sonication, nebulization, enzymatic, or acoustic shearing methods.

In some embodiments, where the sample is a blood sample (e.g., peripheral or whole blood draw), the sample can undergo a red blood cell and white blood cell lysis step, followed by binding of released genomic DNA to a solid support, washing of the solid support with an appropriate wash buffer, and elution of the bound genomic DNA from the solid support into an appropriate solution.

In some embodiments, where the sample contains circulating tumor DNA (ctDNA) (e.g., plasma sample or liquid biopsy sample), the ctDNA can be purified and/or enriched to amplify low amounts of the ctDNA present in the original sample. Various commercial kits exist for isolating, purifying and/or enriching ctDNA from other cellular or sample components, including AVENIO cfDNA isolation and AVENIO ctDNA enrichment kits (Roche Sequencing Solutions, Pleasanton, CA).

Nucleic Acid Library Preparation

Once genomic DNA (e.g., cfDNA and ctDNA) is obtained, the genomic DNA is generally subjected to one or more additional processing steps to generate a library of nucleic acid molecules that are optionally enriched prior to sequencing.

A sequencing library of nucleic acid molecules can be generated from a sample using methods, compositions and systems provided herein or any suitable method known in the art. Various commercial kits exist for the preparation of samples for next-generation sequencing (e.g., AVENIO ctDNA Targeted Panel, Catalog No.: 08061068001 (Roche Sequencing Solutions, Pleasanton, CA); Ion Ampliseq Library Kit 2.0, ThermoFisher Scientific, Catalog No.: 4475345). In one embodiment, a sequencing library comprises a plurality of target nucleic acids (e.g., genomic DNA fragments) that are compatible with any of the sequencing systems disclosed herein or known in the art. In some embodiments, a sequencing library generated from a sample is prepared for use on an Illumina sequencing platform (e.g., HiSeq or MiSeq). Optionally, genomic DNA fragments prepared for use in the sequencing library may comprise one or more oligonucleotide adaptors appended to one, or both, ends of the genomic DNA fragments to aid in downstream analysis or classification. Optionally, the genomic DNA fragments of the sequencing library may contain a barcode, for example, to distinguish one set of genomic DNA fragments from a first sample from genomic DNA fragments prepared from a second sample (e.g., samples from two different sources or samples collected from a cancerous tissue and an adjacent healthy sample from the same source (i.e., matched normal sample).

Steps for preparing a sequencing library may include one or more of: obtaining (e.g., isolating or extracting) genomic DNA from a sample, fragmenting the genomic DNA, preparing the genomic DNA for oligonucleotide adaptor ligation (e.g., end-repair and polyadenylating the 3' end of the genomic DNA fragments), ligating oligonucleotide adaptors to one or both ends of the genomic DNA fragments, purifying the ligated genomic DNA fragments, amplifying the ligated genomic DNA fragments using one or more primers thereby forming amplicons of the genomic DNA fragments, hybridizing the amplicons to generate captured DNA, separating the captured DNA from other unbound nucleic acids, amplifying the eluted DNA, and storing the eluted DNA for sequencing.

In other embodiments, steps for preparing a sequencing library may include one or more of: enriching the ligated oligonucleotide adaptor genomic DNA fragments, amplifying the enriched ligated oligonucleotide adaptor genomic DNA fragments using one or more primers thereby forming amplicons of the genomic DNA fragments and sequencing the amplicons on a sequencing platform.

In some embodiments, genomic DNA undergoes one or more of: DNA polishing, end-repair, and A tailing. For example, in instances where genomic DNA is prepared by sonication, the fragmented genomic DNA can be converted to blunt-ended genomic DNA fragments having a 5' phosphate and 3' hydroxyl group (e.g., using T4 PNK, Klenow and T4 DNA polymerase). Various commercial kits are available for processing of genomic DNA including, but not limited to, NEB Next Ultra II DNA Library Prep Kit for Illumina (New England BioLabs, Catalog No: E7645S). In some embodiments, the genomic DNA is processed to obtain double-stranded blunt-ended genomic DNA fragments. In a preferred embodiment, the blunt-ended genomic DNA fragments can be used for blunt-ended oligonucleotide adaptor ligation.

In some embodiments, genomic DNA is subjected to DNA polishing, end-repair and appendage of an-A tail such that a double-stranded genomic DNA fragment is obtained. In a preferred embodiment, processing of the genomic DNA results in a blunt-ended double-stranded nucleic acid molecule prior to ligation of one or more adaptor oligonucleotides to the 5' and/or 3' end of the processed genomic DNA fragments.

Adaptor Oligonucleotides

In certain embodiments, genomic DNA fragments (e.g., nucleic acid molecules of interest, optionally having a double-stranded nucleic acid structure) are attached to an adaptor oligonucleotide. In some embodiments, the adaptor oligonucleotide can be designed to include overhangs or blunt ends. In a preferred embodiment, adaptor oligonucleotides are designed to create blunt-ended double-stranded nucleic acid molecules of interest when ligated to genomic DNA fragments. In one embodiment, the adaptor oligonucleotide comprises a universal sequence. As used herein, a "universal sequence" refers to a sequence that can be attached, for example, by ligation or other methods disclosed herein, to genomic DNA fragments, such that the universal sequence is attached to a plurality of genomic DNA fragments. The universal sequence is therefore "common" to the many different genomic DNA fragments to which it is attached. A universal sequence is particularly useful for analyzing multiple samples simultaneously, as disclosed herein. Examples of universal sequences are universal primers and universal priming sites. A universal priming site contains a "common priming site" to which an appropriate primer (e.g., universal primer) can hybridize to, and which can be utilized as a priming site for synthesis of nucleic acid sequences complementary to the genomic DNA fragment attached to the universal primer. Exemplary workflows and kits for performing oligonucleotide adaptor ligation include AVENIO ctDNA Library Prep Kit (Roche Sequencing Solutions, Pleasanton, CA). In some embodiments, the genomic DNA comprising one or more oligonucleotide adaptors is purified or isolated from unligated genomic DNA fragments.

Amplification

In some embodiments, genomic DNA fragments, optionally comprising ligated adaptor oligonucleotides, are amplified prior to sequencing Amplification of genomic DNA fragments is particularly useful when the starting concentration or amount of the nucleic acids of interest are low e.g., ctDNA or liquid biopsy samples. In some embodiments, amplification can be coupled with an "enrichment" or "capture process" discussed below to selectively bind nucleic acid molecules of interest. As such the purpose of enrichment is to enrich for nucleic acids of interest from the sample.

Primers having complementary sequences to the nucleic acid molecules of interest, (e.g., genomic DNA fragments) or optionally primer binding sites (e.g., universal primer binding sites in the adaptor oligonucleotides) are incubated with the genomic DNA fragments as a reaction mixture under conditions that allow for repeated annealing, extension, and denaturation steps. Typically, denaturation occurs at a temperature above 95° C., and annealing temperatures are determined based on various aspects of the genomic DNA fragments, including but not limited to length, GC content, and ionic strength of the amplification reaction.

In some embodiments, the methods described herein include amplifying genomic DNA fragments prior to sequencing (e.g., prior to obtaining sequencing reads). In some embodiments, the amplification comprises contacting the genomic DNA fragment with one or more primers (e.g., universal primers or target-specific primers) and amplifying the genomic DNA fragment to produce amplicons. In some embodiments, the methods include detecting a nucleic acid amplification product (e.g., amplicons) generated by the amplification reaction (e.g., RT-PCR). In some embodiments, the amplification comprises PCR. In some embodiments, the genomic DNA is clonally amplified in solution or in microdroplets, such as emulsions. In some embodiments, genomic DNA is amplified by a primer having a nucleic acid sequence that is complementary or substantially complementary (e.g., >85%) to a nucleic acid sequence present in the genomic DNA fragment. In some embodiments, the genomic DNA fragment is amplified by a primer having a sequence that is complementary to a primer binding site in the genomic DNA fragment (e.g., universal primer site in an adaptor oligonucleotide). In some aspects, the amplification step is an optional step, such that the methods described herein for detecting MSI can be performed in the absence of amplification of genomic DNA fragments. For example, a sample from a subject may be processed to obtain genomic DNA fragments that are end-repaired and possess a 3' A tail to create 5' phosphorylated blunt-ended double-stranded nucleic acid molecules of interest. To which, adaptor oligonucleotides are ligated to one or both ends of the nucleic acid molecules thereby forming double-stranded nucleic acid molecules having universal primer binding sites. Subsequently, the nucleic acid molecules having universal primer binding sites can be enriched from the sample (e.g., using a capture probe) and denatured to form single-stranded nucleic acid molecules ready for sequencing as described below. In this example, no amplification of genomic DNA fragments is necessary.

In some embodiments, a second amplification of the genomic DNA fragments occurs prior to sequencing. In one embodiment, a first amplification of the genomic DNA fragments occurs prior to selective enrichment (e.g., using capture probes that are complementary to the universal primer binding site in the adaptor oligonucleotide, discussed below) and a second amplification occurs on the products of the selective enrichment. In yet another embodiment, amplification of genomic DNA fragments occurs prior to sequencing. In another embodiment, amplification of the genomic DNA fragments occurs prior to both selective enrichment and sequencing.

Nucleic Acid Capture

Some embodiments of the disclosure relate to methods for the selective enrichment of nucleic acid molecules of interest (e.g., genomic DNA fragments, amplicons and PCR products) from a reaction mixture. In some embodiments, selective enrichment of nucleic acid molecules of interest utilizes a pool of oligonucleotide probes (e.g., capture probes). In some embodiments, the pool of oligonucleotide probes are freely available in solution. In another embodiments, the pool of oligonucleotide probes may be attached to one or more solid supports. In one embodiment, the method relates to enriching microsatellite loci in a human genomic DNA sample.

In some embodiments, the method of enriching microsatellite loci in a human genomic DNA sample comprises: (1) hybridizing the human genomic DNA to an array of oligonucleotides probes; (2) removing unhybridized genomic DNA, (3) eluting hybridized genomic DNA from the array of oligonucleotide probes, thereby enriching for microsatellite loci. In one embodiment, the oligonucleotide probes are linked to a solid support or heterologous agent.

In another embodiment, the array comprises a set of oligonucleotide probes complementary over a contiguous sequence of at least 12, 14, 16, 18, or 20 nucleotides to a microsatellite locus selected from the group consisting of microsatellites loci corresponding to loci: 1-170 (see, Table 1). In one embodiment, the set of oligonucleotide probes comprises at least 10, 20, 30, 40, or 50 oligonucleotide probes each being complementary to a different microsatellite locus corresponding to loci: 1-64. In one embodiment, the set of oligonucleotide probes comprises at least 10, 20, 30, 40, or 50 oligonucleotide probes each being complementary to a different microsatellite locus corresponding to the loci of Table 2.

In some embodiments, the oligonucleotide probes are free in solution. In another embodiment, the oligonucleotide probes are linked to a heterologous agent. In one embodiment, the heterologous agent is biotin. In another embodiment, the oligonucleotide probes are linked the same solid support. In yet another embodiment, the oligonucleotide probes are linked to separate solid supports.

In one embodiment, the oligonucleotide probe can comprise a modified nucleotide. In some embodiments, an oligonucleotide probe can include a hybridization region that is complementary to a portion of the nucleic acid molecule of interest (e.g., genomic DNA fragment, amplicon or related PCR products). In certain embodiments, a hybridization region can comprise at least about 5 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, and at least about 100 nucleotides. In another embodiment, the hybridization region is between about 6 and about 50, about 8 and about 40, about 10 to about 30 nucleotides in length. In yet another embodiment, the hybridization region is at least 5, 8, 10 or 12 nucleotides in length that is at least 70% complementary to the nucleic acid of interest. In one embodiment, the genomic DNA is enriched for microsatellite loci by hybridizing the genomic DNA to the oligonucleotide probes that hybridize to microsatellite locus-containing DNA.

In some embodiments, the hybridization region of the oligonucleotide probe can comprise at least about 70%, 80%, 85%, 90%, 95%, 96%, 97%, 98%, 99% complementary to the nucleic acid molecule of interest. In some embodiments, the hybridization region comprises a nucleic acid sequence that is 100% complementary to a portion of the nucleic acid molecule of interest (e.g., a genomic DNA fragment).

A heterologous agent can be used in the methods described herein to detect nucleic acids. A wide variety of heterologous agent can be used, with the choice of heterologous agent depending on the sensitivity required, specificity required, ease of conjugation to the oligonucleotide probe, stability requirements, and available instrumentation and disposal provisions. Suitable heterologous agents include, but are not limited to, radionuclides, fluorescent dyes (e.g., fluorescein, fluorescein isothiocyanate (FITC), Oregon Green™, rhodamine, Texas red, tetrarhodimine isothiocyanate (TRITC), Cy3, Cy3.5, Cy5, Cy5.5, JOE, VIC, TET, HEX, FAM, R6G, R110, TAMRA, SYBR-Green, EtBr, and ROX etc.), fluorescent markers (e.g., green fluorescent protein (GFP), phycoerythrin, etc.), colorimetric labels, chemiluminescent labels, bioluminescent labels, antibodies, antigens, haptens, enzymes (e.g., luciferase, horseradish peroxidase, alkaline phosphatase, etc.), nanoparticles, digoxigenin, metals, and the like.

Specific binding of an oligonucleotide probe to genomic DNA can be detected directly or indirectly. Direct labels include fluorescent or luminescent tags, metals, dyes, radionuclides, and the like, attached to the oligonucleotide probe. An oligonucleotide probe labeled with phosphorus-32 ($^{32}$P) can be used. A chemiluminescence assay using a chemiluminescent oligonucleotide specific for genomic DNA can be used. An oligonucleotide probe labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, MO).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked oligonucleotide probes, a quantitative analysis can be made using a spectrophotometer such as an EMAX Microplate Reader (Molecular Devices; Menlo Park, CA) in accordance with the manufacturer's instructions. If desired, the assays can be automated or performed robotically, and the signal from multiple samples can be detected simultaneously. In some embodiments, the amount of signal can be quantified using an automated high-content imaging system. High-content imaging systems are commercially available (e.g., ImageXpress, Molecular Devices Inc., Sunnyvale, CA).

As discussed above, an oligonucleotide probe can include an affinity tag. Affinity tags can be useful for the separation of nucleic acid molecules hybridized to hybridization regions. As used herein, the term "affinity tag" and grammatical equivalents can refer to a component of a multi-component complex, wherein the components of the multi-component complex specifically interact with or bind to each other. For example, an affinity tag can include biotin that can bind streptavidin. Other examples of multiple-component affinity tag complexes include, ligands and their receptors, for example, avidin-biotin, streptavidin-biotin, and derivatives of biotin, streptavidin, or avidin, including, but not limited to, 2-iminobiotin, desthiobiotin, NeutrAvidin (Molecular Probes, Eugene, Oreg.), CaptAvidin (Molecular Probes), and the like; binding proteins/peptides, including maltose-maltose binding protein (MBP), calcium-calcium binding protein/peptide (CBP); antigen-antibody, including epitope tags, including c-MYC, HA VSV-G, HSV, V5, and FLAG Tag™, and their corresponding anti-epitope antibodies; haptens, for example, dinitrophenyl and digoxigenin, and their corresponding antibodies; aptamers and their corresponding targets; fluorophores and anti-fluorophore antibodies; and the like.

As discussed above, an oligonucleotide probe can comprise a reporter moiety. As used herein, the term "reporter moiety" and grammatical equivalents can refer to any identifiable tag, label, or group. The skilled artisan will appreciate that different species of reporter moieties can be used with the methods described herein, either individually or in combination with one or more different reporter moieties. In certain embodiments, a reporter moiety can emit a signal. Examples of signals fluorescent, a chemiluminescent, a bioluminescent, a phosphorescent, a radioactive, a calorimetric, or an electrochemiluminescent signals. Exemplary reporter moieties include fluorophores, radioisotopes, chromogens, enzymes, antigens including epitope tags, semiconductor nanocrystals such as quantum dots (see U.S. Pat. No. 6,544,732), heavy metals, dyes, phosphorescence groups, chemiluminescent groups, electrochemical detection moieties, binding proteins, phosphors, rare earth chelates, transition metal chelates, near-infrared dyes, electrochemiluminescence labels, and mass spectrometer compatible reporter moieties, such as mass tags, charge tags, and isotopes. Additional reporter moieties that may be used with the methods described herein include spectral labels such as fluorescent dyes (e.g., fluorescein isothiocyanate, Texas red, rhodamine, and the like), radiolabels (e.g., $^3$H, $^{125}$I, $^{35}$S, $^{14}$C, $^{32}$P, etc.), enzymes (e.g., horse-radish peroxidase, alkaline phosphatase, etc.) spectral calorimetric labels such as colloidal gold or colored glass or plastic (e.g. polystyrene, polypropylene, latex, etc.) beads; magnetic, electrical, thermal labels; and mass tags. Reporter moieties can also include enzymes (horseradish peroxidase, etc.) and magnetic particles. These and other exemplary reporter moieties are described in the 6th Edition of the Molecular Probes Handbook by Richard Haugland, incorporated by reference herein.

In some embodiments, an oligonucleotide probe can be associated with a substrate. Examples of substrates include microspheres, planar surfaces, columns, and the like. By "microsphere" or "bead" or "particle" or grammatical equivalents herein is meant a small discrete particle. The composition of the substrate will vary on the application. Suitable compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. The beads need not be spherical; irregular particles may be used. Additionally, the microspheres need not be consistent in size. In a preferred embodiment, one or more oligonucleotide probes are associated (e.g., bound, ligated or conjugated) to beads having less than 10% variation in average particle diameter. In some embodiments, a substrate can comprise a metallic composition, e.g., ferrous, and may also comprise magnetic properties. One exemplary embodiment includes oligonucleotide probes comprising streptavidin-coated magnetic beads (Ito et al., (1992) *PNAS* 89:495-498). In addition, the beads may be porous, thus increasing the surface area of the bead available for association with oligonucleotide probes. Typically, bead sizes range from nanometers, i.e. 1 nm to 999 nm; millimeters, i.e. 1 mm to 9 mm, to microns, i.e., 0.1 μm to about 990 μm.

In certain embodiments, an oligonucleotide probe can comprise a cleavable moiety, for example, a cleavable linker. Cleavable moieties can include functional groups that can be cleaved by methods such as photolytically, chemically, thermally, or enzymatically cleaved. See, e.g., U.S. Pat. No. 5,721,099; U.S. Patent Publication No. 20040166529 and 20100022761; and Greene et al., PROTECTIVE GROUPS IN ORGANIC SYNTHESIS, 2nd ed. Wiley, 1991.

In some embodiments, one or more oligonucleotide probes (e.g., a pool of oligonucleotide probes) can be contacted with nucleic acids of interest (e.g., genomic DNA fragments, amplicons or related PCR products) such that a hybridization complex is formed between the oligonucleotide probe and the nucleic acids of interest, thereby generating captured DNA comprising microsatellite loci. In some embodiments, a hybridization complex can be formed by denaturing the nucleic acids of interest prior to contacting with the pool of oligonucleotide probes. In a preferred embodiment, the hybridized nucleic acids of interest and pool of oligonucleotide probes (e.g., hybridization complexes) are separated from unhybridized, unbound and non-specifically bound nucleic acids.

In some embodiments, nucleic acid enrichment can include associating an oligonucleotide probe with a binding moiety. Binding moieties can be associated with affinity tags, and can include ligands for such affinity tags. Binding moieties may be attached to substrates. In some embodiments, nucleic acid enrichment can include removing unhybridized nucleic acids from the hybridized nucleic acid and oligonucleotide probe. Methods of removing can include, for example, washing. Methods of washing nucleic acids are well known in the art. Such methods can be applied to methods that include hybridizing nucleic acids to oligonucleotide probes. A variety of hybridization and washing conditions may be used including high, moderate and low stringency conditions; see for example Maniatis et al., Molecular Cloning: A Laboratory Manual, 2d Edition, 1989, and Short Protocols in Molecular Biology, ed. Ausubel, et al. Stringent conditions include those that can be sequence-dependent and will be different in different circumstances. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993), the disclosure of which is incorporated herein by reference in its entirety. Generally, stringent conditions can be selected to be about 5-10° C. lower than the thermal melting point ($T_m$) for the specific sequence at a defined ionic strength and pH. The Tm is the temperature (under defined ionic strength, pH and nucleic acid concentration) at which 50% of the oligonucleotide probes hybridize to the nucleic acids of interest. Stringent conditions include those in which the salt concentration is less than about 1.0 M sodium ion, for example, about 0.01 M to 1.0 M sodium ion concentration (or other salts) at pH 7.0 to 8.3 and the temperature is at least about 3° C. lower than the $T_m$ for short probes (e.g. 10 to 50 nucleotides) and at least about 6° C. lower than the $T_m$ for long probes (e.g. greater than 50 nucleotides).

In some embodiments, captured DNA (e.g., hybridized nucleic acid molecules and corresponding hybridized oligonucleotide probe) can be released from the hybridization complex subsequent to the removal of non-specific and unbound nucleic acids. As will be understood, methods to disassociate nucleic acid molecules from hybridized oligonucleotide probes will vary according to the type of association between the nucleic acid molecule and the oligonucleotide probe. In some embodiments, nucleic acid molecules can be disassociated from the oligonucleotide probe by denaturing the nucleic acid molecules, e.g., by increasing temperature of the reaction mixture. In some embodiments, a nucleic acid molecule can be disassociated from at least a portion of the oligonucleotide probe by cleaving a cleavable linker. In some embodiments, a nucleic acid molecule can be disassociated from at least a portion of the oligonucleotide probe by digesting at least a portion of the oligonucleotide probe, e.g., RNA oligonucleotide probes can be digested with RNAse. In some embodiments, a nucleic acid molecule can be disassociated from an oligonucleotide probe by modulation the ionic strength of the reaction mixture.

In some embodiments, enriching nucleic acid molecules of interest associated with one or more oligonucleotide probes can include one or more rounds of enrichment. In one embodiment, enrichment methods may include: (1) denaturing the nucleic acid molecules of interest and hybridizing labeled oligonucleotide probes to the nucleic acid molecules of interest (e.g., biotin labeled probes hybridized to genomic DNA fragments); (2) binding labeled oligonucleotide probes and hybridized nucleic acid molecules of interest to a solid-support, e.g., magnetic streptavidin beads, (3) washing the solid support and removing unassociated nucleic acids, and (4) eluting enriched nucleic acid molecules of interest from the solid support. In a second round of enrichment, the enriched nucleic acid molecules of interest may undergo steps (1)-(4).

In some embodiments, the eluted DNA is stored in an appropriate buffer for further processing, such as sequencing. At this point, the enriched nucleic acid molecules may be referred to as a "sequencing library". In some embodiments, the sequencing library is quantified and/or pooled with other sequencing libraries prior to sequencing.

Sequencing

As indicated above, the prepared nucleic acid molecules of interest (e.g., a sequencing library) are sequenced using a sequencing assay as part of the procedure for determining sequencing reads for a plurality of microsatellite loci. Any of a number of sequencing technologies or sequencing assays can be utilized. The term "Next Generation Sequencing (NGS)" as used herein refers to sequencing methods that allow for massively parallel sequencing of clonally amplified molecules and of single nucleic acid molecules.

Non-limiting examples of sequence assays that are suitable for use with the methods disclosed herein include nanopore sequencing (US Pat. Publ. Nos. 2013/0244340, 2013/0264207, 2014/0134616, 2015/0119259 and 2015/0337366), Sanger sequencing, capillary array sequencing, thermal cycle sequencing (Sears et al., *Biotechniques,* 13:626-633 (1992)), solid-phase sequencing (Zimmerman et al., *Methods Mol. Cell Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), sequencing by hybridization (Drmanac et al., *Nature Biotech.,* 16:54-58 (1998), and NGS methods, including but not limited to sequencing by synthesis (e.g., HiSeg™ MiSeg™, or Genome Analyzer, each available from Illumina), sequencing by ligation (e.g., SOLiD™, Life Technologies), ion semiconductor sequencing (e.g., Ion Torrent™, Life Technologies), SMRT® sequencing (e.g., Pacific Biosciences) and pyrosequencing (e.g., 454™ sequencing, Roche Applied Science). See, e.g., Liu et al., *J. Biomed Biotechnol,* 2012, 2012:251364, incorporated by reference herein.

Commercially available sequencing technologies include: sequencing-by-hybridization platforms from Affymetrix Inc. (Sunnyvale, Calif.), sequencing-by-synthesis platforms from Illumina/Solexa (San Diego, Calif.) and Helicos Biosciences (Cambridge, Mass.), sequencing-by-ligation platform from Applied Biosystems (Foster City, Calif.). Other sequencing technologies include, but are not limited to, the Ion Torrent technology (ThermoFisher Scientific), and nanopore sequencing (Genia Technology from Roche Sequencing Solutions, Santa Clara, Cal.); and Oxford Nanopore Technologies (Oxford, United Kingdom).

In another non-limiting embodiment, the methods described herein comprise obtaining sequence reads for genomic DNA using nanopore sequencing (e.g. as described in Soni G V and Meller A. Clin Chem 53: 1996-2001 (2007)). Nanopore sequencing DNA analysis techniques are available from a number of companies, including, for example, Oxford Nanopore Technologies (Oxford, United Kingdom) and Sequenom (San Diego, CA). Nanopore sequencing is a single-molecule sequencing technology whereby a single molecule of DNA is sequenced directly as it passes through a nanopore. A nanopore is a small hole, typically of the order of 1 nanometer in diameter Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a correlation to nucleotides incorporated into the synthesized DNA sequence. In one embodiment, nanopore sequencing can be performed using the Genia technology from Roche Sequencing Solutions (Santa Clara, CA). Genia technology uses a protein nanopore in a lipid bi-layer for each well on a substrate chip, e.g., hundreds of thousands or millions of wells. A well includes a polymerase and a DNA template, where nucleotides are added to the DNA template through polymerization by the polymerase. Unique tags are attached to the four nucleotides corresponding to adenine (A), thymine (T), cytosine (C) and guanine (G). When a nucleotide is added (via catalysis) to the DNA template, the tag threads into the nanopore, resulting in unique signal (i.e., an electrical current) that corresponds to the particular nucleotide incorporated. Specifically, an alternating current (AC) signal is applied across the nanopore, which causes the tag to thread in and out of the nanopore many times, with data being acquired multiple times during the process (see, e.g., US 2015/0119259, US 2016/0178577 and US 2017/0254797).

Typically, nanopore sequencing (nanopore sequencing-by-synthesis) involves using a DNA polymerase or other strand-extending enzyme to synthesize a DNA strand complementary to a template nucleic acid and concurrently determining the identity of each nucleotide as it is added to the growing strand, thereby determining the template sequence. Each added nucleotide is detected by monitoring current flow through a nanopore located adjacent to the polymerase active site over time as the strand is synthesized. Obtaining an accurate signal requires proper positioning of the polymerase active site near a nanopore, and the use of a tag on each added nucleotide which can enter the nanopore and provide an identifiable change in the current flowing through the nanopore. In order to provide for accurate nanopore sequencing, the tag should enter and reside in the nanopore for a sufficient amount of time (i.e., "dwell time"), and while residing in the nanopore, provide for a sufficiently detectable, and identifiable blockage of current through the nanopore (i.e., "blocking current"), such that the specific nucleotide associated with the tag can be distinguished unambiguously from the other tagged nucleotides.

In another non-limiting, embodiment, the methods described herein comprises obtaining sequence reads for genomic DNA using a chemical-sensitive field effect transistor (chemFET) array (e.g., as described in U.S. Patent Application Publication No. 2009/0026082). In one example of this technique, nucleic acid molecules of interest can be placed into reaction chambers, and the nucleic acid molecules are hybridized to a sequencing primer in the presence of a polymerase. Incorporation of one or more triphosphates at the 3' end of the sequencing primer can be discerned as a change in current by a chemFET.

In another embodiment, Ion Torrent™ sequencing, which combines semiconductor technology and unlabeled sequencing chemistry can be used to directly translate chemically encoded information (A, C, G, T) into digital information (0, 1) on a semiconductor chip. Ion Torrent uses a high-density array of micro-machined wells to perform massively parallel incorporation of nucleotides to the 3' end of a sequencing primer with concomitant release of a hydrogen ion for each nucleotide that is incorporated. Each well holds a single nucleic acid molecule of interest and beneath the wells is an ion-sensitive layer (ISFET) and an ion sensor. When a nucleotide is incorporated into the 3' end of the sequencing primer, a hydrogen ion is released causing a slight change the pH of the solution, which can be detected by the ion sensor. The Ion Torrent sequencer sequentially floods the chip with each nucleotide sequentially followed by a wash step to remove unincorporated nucleotides. If a nucleotide is not incorporated during its application to the chip, there is no voltage change and no nucleotide incorporated noted.

Any detection method may be used which is suitable for the sequencing assay employed. In some embodiments, the sequencing assay can employ a label in the detection method. The term "label" as used herein refers to a composition detectable by spectroscopic, photochemical, biochemical, immunochemical, chemical, or other physical means. For example, useful labels include fluorescent dyes, luminescent agents, radioisotopes (e.g., $^{32}$P, $^3$H), electron-dense reagents, enzymes, biotin, digoxigenin, or haptens and proteins, or other entities which can be made detectable, e.g., by incorporating a radiolabel into an oligonucleotide. Exemplary detection methods include radioactive detection (e.g., $^{32}$P), optical absorbance detection, e.g., UV-visible absorbance detection, optical emission detection, e.g., fluorescence or chemiluminescence. For example, genomic DNA fragments can be detected using a sequencing platform by scanning all or portions of each labeled genomic DNA fragment, amplicon or related PCR product, simultaneously or serially, depending on the sequencing platform and method used. For radioactive signals (e.g., $^{32}$P), a phosphorimager device can be used (Johnston et al., 1990; Drmanac et al., 1992; 1993). In another embodiment, genomic DNA fragments can be label-free and their production detected by release of hydrogen ions during incorporation of each nucleotide during DNA synthesis (i.e., Ion Torrent sequencing and e.g., U.S. Pat. Nos. 9,139,874; 9,309,557 and 9,657,281). In another embodiment, the sequencing assay can include nanopore sequencing such as, but not limited to, sequencing methods disclosed in U.S. Pat. Nos. 8,852,864; 8,968,540; 9,121,059; 9,279,153; and 9,542,527.

In some embodiments, a signal from any of the detection methods utilized can be measured and/or analyzed manually or by appropriate computational methods to provide sequencing data that is preferably converted to sequencing reads. In some embodiments, a computational method can be used to interpret sequencing reads, via a computer system.

In some embodiments of the methods described herein, the sequencing reads obtained from a sequencing assay comprise about 20 nucleotides, about 25 nucleotides, about 30 nucleotides, about 35 nucleotides, about 40 nucleotides, about 45 nucleotides, about 50 nucleotides, about 55 nucleotides, about 60 nucleotides, about 65 nucleotides, about 70 nucleotides, about 75 nucleotides, about 80 nucleotides, about 85 nucleotides, about 90 nucleotides, about 95 nucleotides, about 100 nucleotides, about 120 nucleotides, about 150 nucleotides, about 200 nucleotides, about 250 nucleotides, about 300 nucleotides, about 350 nucleotides, about 400 nucleotides, about 450 nucleotides, or about 500 nucleotides in length. In some embodiments, the sequencing reads obtained from a sequencing assay comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, a sequencing read comprises at least 10 or more nucleotides that are discerned in a single sequencing reaction. As such, it is not necessary that each sequencing reaction be complete or that each sequencing read be unambiguous.

Any suitable method, calculation, or threshold may be used to determine whether the alignment of the sequencing reads aligns with the microsatellite locus (for example, Li et al., *Bioinformatics*, (2009) 25(14):1754-1760. Preferably, at least 8, 10, 20, 30, 40, 50, or more contiguous nucleotides from each sequencing read align with the corresponding microsatellite locus. In one embodiment, each sequencing read comprises 10 or more contiguous nucleotides that correspond to a microsatellite locus of interest. In some embodiments, the sequencing reads may overlap (tile) across a genome, gene, or domain of interest (e.g., regions of a chromosome, whole chromosomes, exons, introns, and the like). In some embodiments, the sequencing reads comprise at least 1%, 5%, 10%, 20%, 25%, 30%, 40%, 50%, 60%, 70%, 75%, 80%, or more of a genome. In another embodiment, the sequencing reads align to one, a plurality, or all of a set of microsatellite loci under evaluation.

In one embodiment, the sequencing reads can be mapped to a reference genome such as the GRCh37/hg19 sequence or the GRCh38/hg38 sequence. Other sources of public sequence information include GenBank, dbEST, dbSTS, EMBL (the European Molecular Biology Laboratory), and the DDBJ (the DNA Databank of Japan).

A number of computer algorithms are available for aligning nucleotide sequences such as the sequencing reads described herein, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA).

As will be apparent from the quantity of genomic DNA fragments typically present in a sample, a plurality of sequence reads are obtained per sequencing assay. In some embodiments, at least about $3 \times 10^6$ sequencing reads, at least about $5 \times 10^6$ sequencing reads, at least about $8 \times 10^6$ sequencing reads, at least about $10 \times 10^6$ sequencing reads, at least about $15 \times 10^6$ sequencing reads, at least about $20 \times 10^6$ sequencing reads, at least about $30 \times 10^6$ sequencing reads, at least about $40 \times 10^6$ sequencing reads, or at least about $50 \times 10^6$ sequencing reads are obtained. In some embodiments, the sequencing reads comprise between about 20 and about 500 nucleotides per sequencing read. In one embodiment, each sequencing read or a portion (e.g., about 10% or more) of the total sequencing reads are mapped to a reference genome. In another embodiment, the sequencing reads mapped to a reference genome are retained and utilized for further processing (e.g., for determining a metric for RLD), while sequencing reads that do not map to, or align, with the reference genome and/or microsatellite loci are discarded.

Analysis

Figure 4:
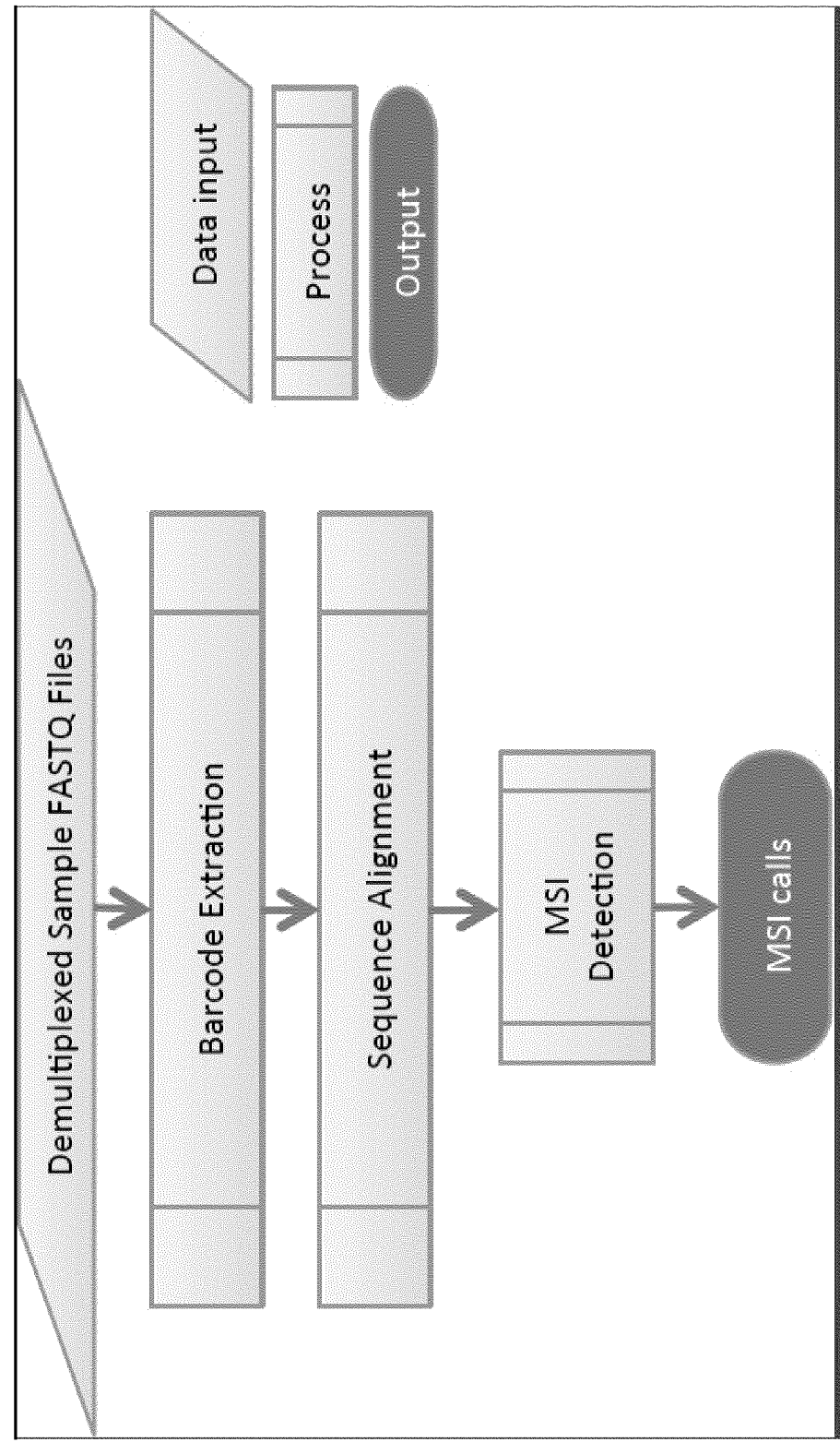
FIG. 4 shows an exemplary bioinformatics workflow for the microsatellite instability tissue caller component of FIG. 3.

In some embodiments, data obtained from a sequencing reaction or assay is in the form of nucleotide sequences representing sequencing reads obtained from the sample. In some embodiments, the sequencing assay produces between 1 million and 100,000 million, between 50 million and 10,000 million, and 100 million and 1,000 million sequencing reads. In some embodiments, the sequencing reads (e.g., raw data) can be refined to remove bad quality or low quality sequencing reads. In some embodiments, the sequencing assay provides greater than 100 sequencing reads and fewer than 1,000,000 sequencing reads per microsatellite locus. In another embodiment, the sequencing reads can be deduplicated to remove duplicate reads from the sequencing data. In another embodiment, the sequencing reads can be refined to remove adaptor oligonucleotides, universal primer binding sites and/or barcode sequences from the sequencing read data. In some embodiments, the sequencing reads can be saved in an appropriate bioinformatics format, such as but not limited to, FASTA and FASTQ format. An exemplary workflow for the processing of sequencing reads obtained by the methods disclosed herein to detect microsatellite instability is provided in FIG. 4.

After sequencing reads are generated and sequencing reads comprising a microsatellite locus are identified (e.g., by alignment of the sequencing reads to a reference genome or set of known microsatellite loci). Typically, the number of repeat units detected in the sequencing reads at the microsatellite locus can be determined (e.g., counted), thereby generating a Repeat Length Distribution (RLD) across the sequencing reads for each microsatellite locus under evaluation.

As sequencing reads are aligned to microsatellite locus, the number of repeat units in the sequencing read can be determined. For example, a microsatellite locus having a dinucleotide repeat of "GT" may be observed in a first sequencing read as $GT_6$, observed in a second sequencing read as $GT_9$, observed in a third sequencing read as $GT_6$, and observed in a fourth sequencing read as $GT_7$. Any method for determining the repeat unit length of a microsatellite locus within a sequencing read may be used. In a preferred method, determining the repeat unit length is performed by computational analysis (e.g., software analysis or algorithm).

Figure 1B:
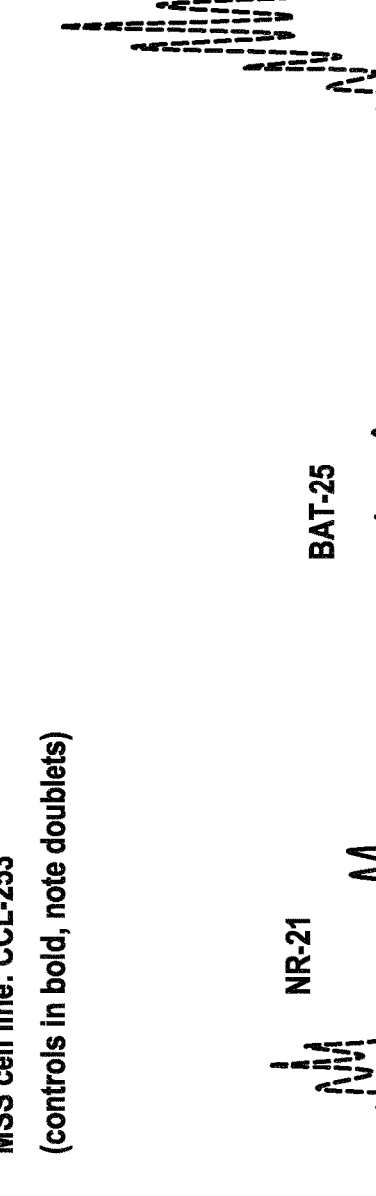
FIG. 1B shows distribution of three MS loci (NR-21, BAT-25, and MONO-27) using a MSI cell line (CCL-253). The distribution of MS loci are shifted to the right in the MSI cell line as compared to the control sample, indicative of smaller MS repeat lengths in the MSI cell line.

Typically, the number of repeat unit lengths among microsatellite loci in MSS or normal (non-cancerous cells) is stable and consistent (e.g., see, FIG. 1A and FIG. 1B). However, the number of repeat unit lengths of an individual microsatellite locus can vary between different cells. Some cells will contain microsatellite loci having identical repeat unit lengths for the same type of cells (e.g., healthy, non-cancerous cells) while other cells (e.g., CRC cells) may contain microsatellite loci having shorter or longer repeat unit lengths. In some embodiments, the repeat unit length determined from a sequencing read, where the sequencing read is a proxy for the cell, will be between about 2 and about 100 repeat units, about 5 and about 80 repeat units, about 10 and about 60 repeat units, and about 15 to about 40 repeat units.

Once the RLD for a microsatellite locus is generated, a metric for RLD can be determined. In some embodiments, the metric for RLD is a t-statistic. In one embodiment, the metric for RLD is a t-statistic such as, but not limited to, Student's t-test or Wilcox-Rank test. In another embodiment, the metric for RLD is determined based on mean read length for a given microsatellite locus. In yet another embodiment, the metric for RLD is determined based on skewness of the RLD among the sequencing reads of a given microsatellite locus. In some embodiments, the metric for RLD is a t-statistic, wherein the t-statistic is determined based on mean read length and variance in the RLD. In another embodiment, the metric for RLD of each microsatellite locus under evaluation is based on a two-sample t-test between a test sample (e.g., ctDNA from a sample suspected of having CRC) and a normal background sample (e.g., a reference sample or a matched healthy sample). In some embodiments, the t-statistic is determined based on the RLD of a test sample and a control RLD. In some embodiments, the metric for RLD is determined in the absence of a matched sample, for example by reference to a known or reference sample where the RLD metric for each microsatellite locus under evaluation is known. In some embodiments, the metric for RLD is determined by comparing the RLD of the microsatellite under evaluation to a pre-computed background RLD for the given microsatellite loci.

Accordingly, one or more statistical values can be determined for a sample RLD and for a pre-computed normal background RLD, and the statistical values can be compared, e.g., as a t-statistic. In other embodiments, the raw values of the two RLDs can be compared, e.g., to determine a distance.

In other embodiments, the metric is a similarity measure between the RLD of a tested sample and a control RLD. Distance metrics include but are not limited to Kullback-Leibler divergence, correlation distance, cosine distance, Euclidean distance, Manhattan distance, and Kolmogorov-Smirnov statistics. The distance metric can be used to evaluate similarities between two RLDs. For example, a difference can be taken between the values (counts) at each length for the two RLDs, e.g., as a numerical vector difference, where each vector is the array of counts of number of reads having a given repeat length.

In some embodiments, inconsistent RLDs across a single microsatellite locus can be filtered using a distance metric to measure the similarity between the two RLDs. A distance metric can be determined using pair-wise distances, e.g., a different or a ratio between corresponding values of each RLD of the pair of RLDs. For instance, a first RLD can have a first probability for a read having a first length (e.g., as determined from a normalized counts of reads having the first length), and a second RLD can have a second probability for a read having the first length.

In some embodiments, a microsatellite locus is considered to have an inconsistent RLD if more than half of the pair-wise distances from the observed RLDs are "long" of any distance metric tested. As used herein, a RLD is "long" if the RLD is greater than median plus two standard deviations distances from all paired samples of all microsatellite loci. In some embodiments, the RLD is measured using a median as opposed to the mean, to reduce the effect of outliers.

In some embodiments, when filtering inconsistent samples of a given microsatellite locus, Euclidean distance may be preferred to measure the similarity between the two RLDs. In one embodiment, a sample is considered inconsistent compared to other samples if its Euclidian distance to a normal background sample is greater than median plus two standard deviation distance from all samples of all microsatellite loci.

In one embodiment, samples having MSI comprise a RLD for one or more microsatellite loci that is distinct from the RLD of the same microsatellite loci observed in MSS samples. In one embodiment, a MSI sample can comprise a RLD that has a mean read length that is longer and/or has greater skewness as compared to a RLD for the same microsatellite loci in MSS samples. For example, FIGS. 1A and 1B demonstrate that microsatellite locus NR-21 is observed to have greater read length and skewness in MSI cell line as compared to the RLD of NR-21 in MSS cell lines.

In some embodiments, the metric is prepared by comparing the RLD for a given microsatellite locus to a pre-computed normal background RLD for the corresponding microsatellite locus. In some instances, the pre-computed normal background is based on a set of normal samples. Then, the metric is compared to a threshold value for the corresponding microsatellite locus. In some instances, the threshold value is chosen to maximize the difference between true positive rate and false positive rate in the training set. In some embodiments, each microsatellite locus has its own independent threshold value to which a calculated RLD metric is compared. In some embodiments, the threshold value comprises the repeat length distribution typically observed in a MSS sample. In some embodiments, the threshold value comprises the repeat length distribution of a normal matched sample. In some embodiments, the threshold value comprises a RLD metric obtained from a MSS cell line. In some embodiments, the threshold value is the value at which a microsatellite locus is identified as MSI. In some embodiments, where the RLD metric exceeds the threshold value for the corresponding microsatellite locus, the microsatellite locus under evaluation is identified as MSI.

In some embodiments, RLD metric's for one or more microsatellite loci obtained from a sample are compared to threshold values for the corresponding microsatellite loci. In one embodiment, microsatellite loci in the sample having a RLD metric that exceeds the threshold value of the corresponding microsatellite loci are identified (e.g., MONO-27, NR-21 and BAT-25). In another embodiment, RLD metric's for microsatellite loci from a sample are compared to threshold values for the corresponding microsatellite loci and the number of microsatellite loci exceeding the corresponding threshold values are quantified (e.g., 58 microsatellite loci with RLD metric's exceeding the corresponding microsatellite loci threshold value from a set of 64 evaluated microsatellite loci (e.g., microsatellite loci corresponding to loci: 1-64).

In some embodiments, the number of microsatellite loci having an RLD metric exceeding the corresponding threshold value (e.g., 58 microsatellite loci out of a total 64 microsatellite loci) is compared to a microsatellite instability proportion threshold (MSI-PT). In one embodiment, if the number of microsatellite loci having an RLD metric greater than the corresponding threshold value (e.g., 58 microsatellite loci) exceeds the MSI-PT, the subject from whom the sample was obtained is classified as microsatellite instable (MSI). In another embodiment, if the number of microsatellite loci having an RLD metric greater than the corresponding threshold value (e.g., 58 microsatellite loci) is equal to or less than the MSI-PT, the subject from whom the sample was obtained is classified as microsatellite stable (MSS).

The microsatellite instability proportion threshold (MSI-PT) represents a fraction or percent of the total number of microsatellite loci evaluated. The MSI-PT threshold can be a pre-defined value or range. In some embodiments, the MSI-PT is greater than at least 35%. The purpose of the MSI-PT is to accurately separate or distinguish samples into MSS or MSI status. In one embodiment, the MSI-PT is at least about 40%, 50%, 60%, 70%, 75%, or more. In the example described above, 58 microsatellite loci from a pool of 64 microsatellite loci are determined to have RLD metric's exceeding the threshold value for the corresponding microsatellite loci. As such, the 58 microsatellite loci are determined to be MSI loci, while the remaining 6 microsatellite loci are determined to be MSS. Additionally, 58 microsatellite loci/64 microsatellite loci equates to 90% of the plurality of microsatellite loci being classified as MSI. Since 90% is greater than the MSI-PT of 35%, the sample is classified as MSI. In some embodiments, if the sample has an MSI-PT of less than 35%, the sample is classified as MSS.

Reference Values

In one embodiment, sequencing reads comprising a microsatellite locus are compared to a threshold value in order to determine whether the microsatellite locus is MSI. The quantity of MSI locus compared to total number of microsatellite loci evaluated are then compared to a MSI-PT. A variety of methods can be used to determine the MSI-PT.

In one embodiment, the MSI-PT corresponds to a reference value for microsatellite loci (e.g., loci: 1-170) and is determined by assessing the level of the microsatellite loci from a population of subjects that are known not to have cancer (e.g., healthy subjects). As a non-limiting example, in one embodiment, the population of subjects (e.g., 10, 20, 50, 100, 200, 500 subjects or more) are known not to have cancer and a sample from each subject is analyzed for the level of microsatellite loci in each sample.

In another embodiment, the MSI-PT corresponds to a reference value for microsatellite loci (e.g., microsatellite loci: 1-170) and is determined by assessing the level of the microsatellite loci in samples from a population of subjects having cancer (e.g., colorectal cancer).

In another non-limiting example, the population of subjects (e.g., 10, 20, 50, 100, 200, 500 subjects or more) have colorectal cancer and a sample from each subject is analyzed for a microsatellite loci (e.g., microsatellite loci: 1-170). In some embodiments, the population of subjects is matched to a subject under investigation according to one or more patient characteristics such as age, gender, ethnicity, or other criteria. In some embodiments, the reference value is established using the same type of sample from the population of subjects (e.g., samples comprising plasma or colorectal tissue samples) as is used to detect MSI in the subject under investigation.

The reference value may be determined using any suitable method (e.g., collecting samples from subjects and determining microsatellite loci levels). It will be understood that standard statistical methods may be employed by the practitioner in making such determinations. See, e.g., Principles of Biostatistics by Marcello Pagano et al. (Brook Cole; 2000); and Fundamentals of Biostatistics by Bernard Rosner (Duxbury Press, 5th Ed, 1999).

In another embodiment, the threshold value for a particular microsatellite locus (e.g., loci: 1) in a sample from a subject under investigation can be compared to a control sample (e.g., a matched healthy sample) in order to determine whether the microsatellite locus is MSI. In some embodiments, a control sample is a sample from a subject who does not exhibit any clinical symptoms of cancer. In some embodiments, a control sample is a sample from a subject who has been clinically diagnosed as having cancer (e.g., colorectal cancer). In some embodiments, the subject from whom the control sample is obtained is the same age or about the same age and/or the same gender as the subject under investigation.

Subjects and Samples

In some embodiments, the sample is from an individual human subject (i.e., a human subject being assessed for cancer). In some embodiments, the subject is an adult human. In some embodiments, the subject is a child. In some embodiments, the subject is a human who has been diagnosed with cancer. In some embodiments, the subject is a human who is suspected of having cancer. In some instances, the subject is a dog, cat, horse, sheep, mouse, rat, rabbit, monkey, or human.

In some embodiments, the sample from the subject comprises whole blood (e.g., blood draw), serum, plasma, saliva, urine, cerebrospinal fluid, or a tissue sample (e.g., colon biopsy). In some embodiments, the sample comprises cells obtained from a tumor. In some embodiments, the sample is a colon tissue sample. In some embodiments, the sample is a cell-free DNA sample. In yet another embodiment, the sample is a circulating tumor DNA (ctDNA) sample. In a preferred embodiment, the sample comprises genomic DNA from the subject. In some embodiments, the genomic DNA originates from an individual subject, preferably a mammal. In some aspects, the sample can include any tissue, cells, or biological fluid from the subject which contains genomic DNA. In some embodiments, the sample is a blood sample. In another embodiment, the sample is a tissue sample obtain from a tumor.

In some embodiments, the sample is a tissue sample fixed in formalin and embedded in paraffin (FFPE). Tissue samples from biopsies are commonly stored in FFPE for long-term preservation. Formalin creates cross-linkages within the tissue sample which can be difficult to break, sometimes resulting in low DNA yields. Another problem associated with formalin-fixed paraffin-embedded samples is amplification of longer nucleic acid fragments is often problematic. When DNA from FFPE samples is used in multiplex amplification reactions, often a significant decrease in peak heights is seen with increasing fragment size. The microsatellite instability method of the present invention is preferably designed to amplify and analyze genomic DNA from FFPE tissue samples. In one embodiment, the methods disclosed herein to detect MSI comprise at least one genomic DNA fragment from a tumor in the subject. In another embodiment, the methods disclosed herein do not require a matched sample from a healthy tissue to detect MSI.

IV. Computer Systems

In one aspect, the disclosure relates to a system for detecting microsatellite instability. In one embodiment, the system comprises a processor and a non-transitory computer readable medium coupled to the processor, the non-transitory computer readable medium comprising code executable by the processor for performing a method, wherein the method comprises (1) receiving sequencing reads from human genomic DNA for a plurality of microsatellite loci; (2) determining a repeat length distribution (RLD) for each microsatellite locus; (3) generating a metric for the RLD for each microsatellite locus; (4) comparing the metric for each microsatellite locus to a threshold value for the microsatellite locus, wherein each microsatellite has an independent threshold value; (5) quantifying the number of detected microsatellite loci having an RLD metric exceeding the threshold value; and (6) comparing (i) the number of microsatellite loci that have an RLD metric exceeding the threshold value to (ii) a locus set proportion threshold, wherein if the number exceeds the locus set proportion threshold, the system classifies the sample from the human as MSI. In some embodiments, if the number of microsatellite loci exceeding the threshold value is lower than the locus-set proportion threshold, the system classifies the sample from the human as MSS. In some embodiments, the system can determine the MSI status of one or more samples concurrently. In a preferred embodiment, the system can determine the MSI status of two or more samples from two or more subjects concurrently.

In one embodiment, the system further comprises at least one device configured to assay a plurality of MSI loci in a sample to determine RLD for the plurality of MSI loci. In some embodiments, a metric for the RLD for each microsatellite locus can comprise a t-statistic such as Student's t-test or Wilcox-Rank test. In some embodiments, the t-statistic for a locus is determined based on mean read length and variance in the RLD for that locus. In some embodiments, the t-statistic is determined based on the RLD of a test sample and a control RLD.

In some embodiments, the computer readable medium, which may include a collection of various storages devices, comprises a database including a listing of available therapeutic agents depending on MSI status; instructions to input the number of microsatellite loci that have an RLD metric exceeding the threshold value and functionality to compare the number of microsatellite loci that have an RLD metric exceeding the threshold value with the locus set proportion threshold. In some embodiments, the computer readable medium further comprises a computer-readable program code having instructions to generate a report that comprises a listing of therapeutic agents for which the comparison to the locus set proportion threshold indicates a likely benefit of the at least one therapeutic agent in the database. In some embodiments, a likely benefit of the at least one therapeutic agent comprises one or more known or documented curative, positive, or ameliorative responses in a human subject diagnosed with MSI. In some embodiments, the at least one therapeutic agent is an antibody, small molecule, chemotherapeutic agent, or a combination thereof. In one embodiment, the at least one therapeutic agent is Pembrolizumab.

In some embodiments, the system further comprises instructions for identifying sequencing reads comprising a microsatellite locus by alignment of the sequencing reads to a set of microsatellite loci DNA sequences and instructions for counting the number of repeat lengths for each sequencing read determined to comprise a microsatellite locus, thereby generating an RLD for each microsatellite locus.

Conventional data networking, application development and other functional aspects of the computer system (and components of the individual operating components of the computer system) are not described in detail herein but are considered part of this disclosure. Furthermore, the connecting lines shown in the various figures contained herein are intended to represent exemplary functional relationships and/or physical couplings between various elements. It should be noted that many alternative or additional functional relationships or physical connections may be present in the computer system.

The various computer system components discussed herein may include one or more of the following: a host server or other computing systems including a processor for processing digital data; a memory coupled to the processor for storing digital data: an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases.

Various databases used herein may include: patient data such as family history, demography and environmental data, biological sample data, prior treatment and protocol data, patient clinical data, molecular profiling data of biological samples, data on therapeutic drug agents and/or investigative drugs, a gene library, a disease library, a drug library, patient tracking data, file management data, financial management data, billing data and/or like data useful in the operation of the system.

As those skilled in the art will appreciate, a computer system may include an operating system (e.g., Windows NT, 95/98/2000, OS2, UNIX, Linux, Solaris, MacOS, etc.) as well as various conventional support software and drivers typically associated with computers. The computer system may include any suitable personal computer, network computer, workstation, minicomputer, mainframe or the like. The computer system can be in a home, medical, or business environment with access to a network. In an exemplary embodiment, access is through a network or the Internet through a commercially-available web-browser software package.

As used herein, the term "network" shall include any electronic communications means which incorporates both hardware and software components of such. Communication among the user and another party may be accomplished through any suitable communication channels, such as, for example, a telephone network, an extranet, an intranet, Internet, point of interaction device, personal digital assistant, cellular phone, kiosk, online communications, satellite communications, off-line communications, wireless communications, transponder communications, local area network (LAN), wide area network (WAN), networked or linked devices, keyboard, mouse and/or any suitable communication or data input modality. Specific information related to the protocols, standards, and application software utilized in connection with the Internet is generally known to those skilled in the art and, as such, need not be detailed herein. See, for example, Dilip Naik, Internet Standards and Protocols (1998); Java 2 complete, various authors, (Sybex 1999); and Deborah Ray and Eric Ray, Mastering html 4.0 (1997).

The various computer system components may be independently, separately or collectively suitably coupled to the network via data links. Moreover, the system contemplates the use, sale or distribution of any goods, services, or information (e.g., sequencing reads or sequencing data) over any network having similar functionality described herein.

As used herein, "transmit" may include sending electronic data from one system component to another over a network connection. Additionally, as used herein, "data" may include encompassing information such as commands, queries, files, data for storage, and the like in digital or any other form.

Any of the computer systems mentioned herein may utilize any suitable number of subsystems. Examples of such subsystems are shown in FIG. 8. In some embodiments, a computer system 10 includes a single computer apparatus, where the subsystems can be the components of the computer apparatus. In other embodiments, a computer system can include multiple computer apparatuses, each being a subsystem, with internal components.

The subsystems shown in FIG. 8 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art, such as serial port 77. For example, serial port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk), as well as the exchange of information between subsystems. The system memory 72 and/or the storage device(s) 79 may embody a computer readable medium. Any of the values mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2.sup.nd ed., 2001). See U.S. Pat. No. 6,420,108.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

As will be appreciated by one of ordinary skill in the art, the computer system may be embodied as a customization of an existing system, an add-on product, upgraded software, a stand-alone system, a distributed system, a method, a data processing system, a device for data processing, and/or a computer program product. Accordingly, the computer system may take the form of an entirely software embodiment, an entirely hardware embodiment, or an embodiment combining aspects of both software and hardware.

Figure 9:
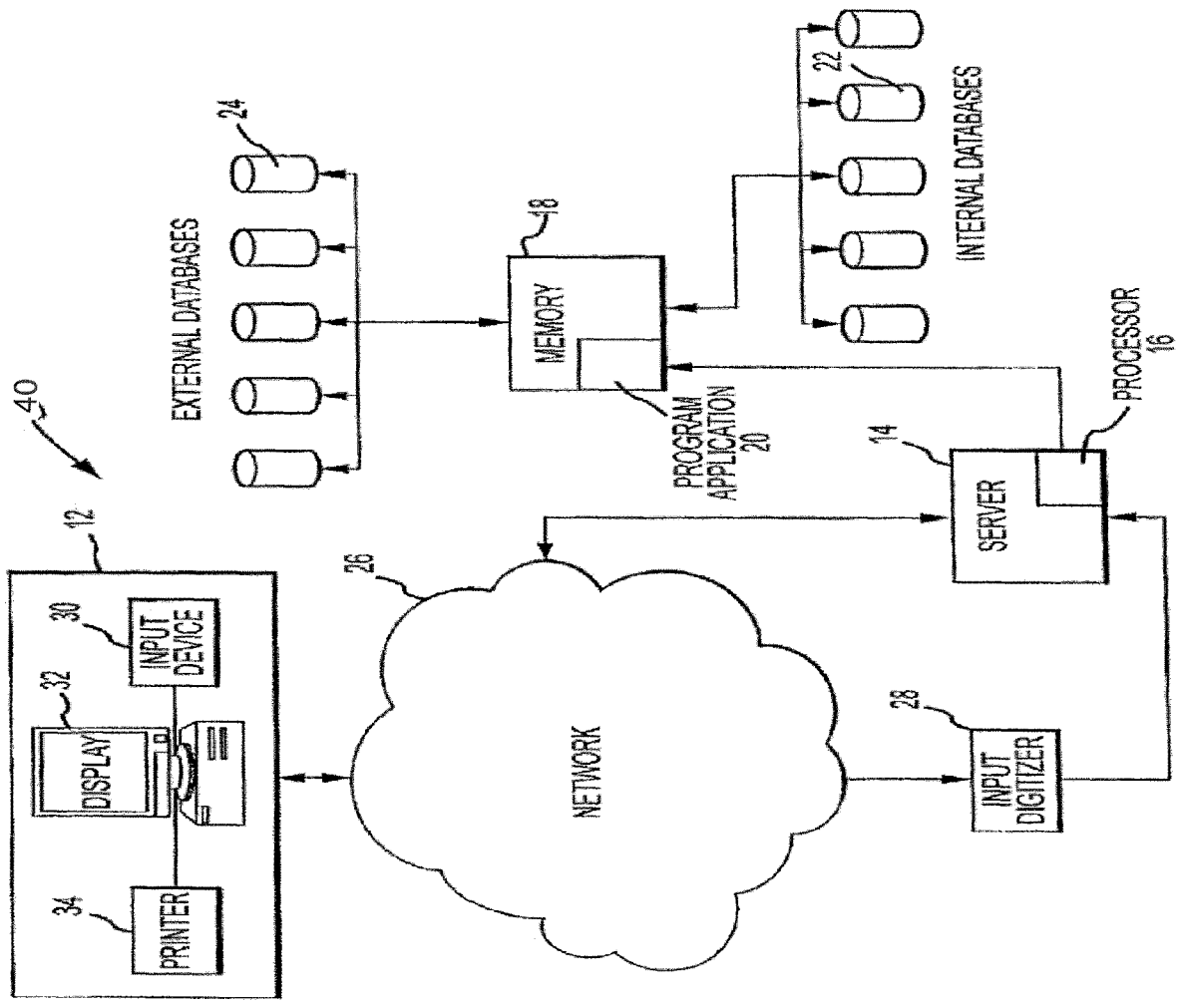
FIG. 9 shows another exemplary system according to one embodiment of the disclosure.

FIG. 9 illustrates a block diagram of an exemplary embodiment of a system 40 for detecting MSI in a sample from a subject that utilizes a metric for the RLD of each microsatellite locus and a loci-set or MSI-PT. System 40 includes a user interface 12, a host server 14 including a processor 16 for processing data, a memory 18 coupled to the processor, an application program 20 stored in the memory 18 and accessible by the processor 16 for directing processing of the data by the processor 16, a plurality of internal databases 22 and external databases 24, and an interface with a wired or wireless communications network 26 (such as the Internet). System 10 may also include an input digitizer 28 coupled to the processor 16 for inputting digital data from data that is received from user interface 12. User interface 12 includes an input device 30 and a display 32 for inputting data into system 10 and for displaying information derived from the data processed by processor 16. User interface 12 may also include a printer 34 for printing the information derived from the data processed by the processor 16 such as reports that may include test results for MSI and proposed therapeutic agents based on the test results. Internal databases 22 may include, but are not limited to, patient sample/specimen information and tracking, clinical data, patient data, file management, study protocols, and patient test results. External databases 24 may include, but are not limited to, drug libraries, disease libraries, and public and private databases such as NCBI, PubMed, UniGene, OMIM, GO, TIGR, GenBank, KEGG and Biocarta.

Additionally, the present disclosure relates to embodiments that include methods for providing genetic information, such as MSI, over networks such as the Internet as shown in U.S. Publication Number 20020183936. For example, one or more methods disclosed herein can be performed in one location, e.g., a city, state, country or continent, and the results can be transmitted to a different city, state, country or continent. Treatment selection can then be made in whole, or in part, in the second location. The methods of the invention comprise transmittal of MSI information between different locations.

V. Therapeutic Methods

In another aspect, methods of treating a subject who has been diagnosed as having MSI (e.g., colorectal cancer) are provided. In some embodiments, the methods described relate to cancer. In some embodiments, the methods comprise treating a subject by delaying or reversing the progression of cancer.

In some embodiments, the method comprises determining whether the subject has MSI. In some embodiments, the method comprises: determining a metric for RLD for a plurality of microsatellite loci in a sample from the subject; comparing the RLD metric to a threshold value for the plurality of microsatellite loci; quantifying the number of microsatellite loci having an RLD metric exceeding the threshold value; comparing the number of microsatellite loci having an RLD metric exceeding the threshold value to a MSI proportion threshold, wherein if the number exceeds the MSI proportion threshold, the subject has MSI; and administering one or more agents to the subject. In some embodiments, the metric for RLD is prepared by determining a sample RLD for each microsatellite locus and compared to a pre-computed background RLD for each microsatellite locus to generate metrics for RLD for each microsatellite locus under evaluation.

An agent as described herein, can be administered, for example, intravenously, intrathecally, intraspinally, intraperitoneally, intramuscularly, intranasally, subcutaneously, orally, topically, and/or by inhalation.

The agent is administered in a manner compatible with the dosage formulation, and in such amount as will be therapeutically effective. The term "therapeutically effective amount" refers to the amount of the agent (e.g., a compound or pharmaceutical composition as described herein) being administered that will treat to some extent a disease, disorder, or condition, e.g., relieve one or more of the symptoms of the disease or a symptom that the subject is at risk of developing. In some embodiments, a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the therapeutic agent being employed. The size of the dose will also be determined by the existence, nature, and extent of any adverse side-effects that accompany the administration of a particular compound in a particular patient. Determination of the proper dosage for a particular situation is within the skill of the practitioner. Frequently, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

In some embodiments, the methods disclosed herein comprise treating a subject with an agent if the subject is diagnosed with MSI. In one embodiment, the agent is Pembrolizumab.

In some embodiments, the subject has or is suspected of having cancer. In some embodiments, the subject with MSI has or is suspected of having colorectal cancer (CRC).

Accordingly, in some embodiments, the methods disclosed herein comprise treating the subject with a known CRC agent, surgery, chemotherapy and/or radiotherapy. In one embodiment, treatment for a subject with CRC is selected from the group consisting of surgery, radiotherapy, agents, and combinations thereof.

In some embodiments, methods of treating colon and/or rectal cancer include one or more agents approved by the Food and Drug Administration (FDA) for colon and/or rectal cancer. In some embodiments, the one or more agents are selected from the lists below. In one embodiment, treatment of CRC includes administering to the human in need thereof of a therapeutic amount of MDG007 (MacroGenics).

In some embodiments, agents approved for the treatment of colon cancer include, but are not limited to:

Avastin (Bevacizumab)
Bevacizumab
Camptosar (Irinotecan Hydrochloride)
Capecitabine
Cetuximab
Cyramza (Ramucirumab)
Eloxatin (Oxaliplatin)
Erbitux (Cetuximab)
5-FU (Fluorouracil Injection)
Fluorouracil Injection
Irinotecan Hydrochloride
Leucovorin Calcium
Lonsurf (Trifluridine and Tipiracil Hydrochloride)
Nivolumab
Opdivo (Nivolumab)
Oxaliplatin
Panitumumab
Ramucirumab
Regorafenib
Stivarga (Regorafenib)
Trifluridine and Tipiracil Hydrochloride
Vectibix (Panitumumab)
Wellcovorin (Leucovorin Calcium)
Xeloda (Capecitabine)
Zaltrap (Ziv-Aflibercept)
Ziv-Aflibercept In another embodiment, combinations of agents approved for the treatment of colon cancer include, but are not limited to:

Capox;
Folfiri;
Folfiri-Bevacizumab;
Folfiri-Cetuximab;
Folfox;
Fu-Lv;
Xeliri;
Xelox;

In some embodiments, agents approved for the treatment of rectal cancer include, but are not limited to:

Avastin (Bevacizumab);
Bevacizumab;
Camptosar (Irinotecan Hydrochloride);
Capecitabine;
Cetuximab;
Cyramza (Ramucirumab);
Eloxatin (Oxaliplatin);
Erbitux (Cetuximab);
5-FU (Fluorouracil Injection);
Irinotecan Hydrochloride;
Leucovorin Calcium;
Lonsurf (Trifluridine and Tipiracil Hydrochloride);
Nivolumab;

Opdivo (Nivolumab);
Oxaliplatin;
Panitumumab;
Ramucirumab;
Regorafenib;
Stivarga (Regorafenib);
Trifluridine and Tipiracil Hydrochloride;
Vectibix (Panitumumab);
Wellcovorin (Leucovorin Calcium);
Xeloda (Capecitabine);
Zaltrap (Ziv-Aflibercept); and
Ziv-Aflibercept.

In some embodiments, agent combinations approved for the treatment of rectal cancer include, but are not limited to:

Capox;
Folfiri;
Folfiri-Bevacizumab;
Folfiri-Cetuximab;
Folfox;
Fu-Lv;
Xeliri; and
Xelox.

In some embodiments, the subject is treated with one or more agents that are specific or responsive for the type of cancer with which the subject has or is suspected of having.

VI. Kits

The disclosure also provides kits that include primers, adaptor oligonucleotides, oligonucleotide probes described herein for performing the methods of the invention. In some embodiments, oligonucleotide probes are provided in solution, whereas in others, they provided attached to a solid support. Preferably, the primers and adaptor oligonucleotides are provided in solution at known concentrations. The kits also include instructions for amplifying the genomic DNA fragments, ligating adaptor oligonucleotides to genomic DNA fragments, hybridizing oligonucleotide probes to genomic DNA fragments and detecting dissociation of oligonucleotide probes from genomic DNA fragments and amplicons.

In certain embodiments, kits also include instructions for one or more of: obtaining genomic DNA fragments, amplifying genomic DNA, binding oligonucleotides probes to genomic DNA, and varying at least one condition (e.g., a temperature condition as part of a melting curve analysis). In addition, the kits optionally include one or more components selected from, e.g., nucleotides, nucleotide analogs, enzymes, salts, buffers, cofactors, and the like. In some embodiments, kits also include nucleic acid molecules that act as positive and/or negative controls for the amplification process, sequencing process, and/or reagents thereof. Typically, the kits also include at least one container for packaging the primers, adaptor oligonucleotide and oligonucleotide probes, the instructions, and/or one or more other components.

EXAMPLES

Example 1—Determination of Repeat Length Distribution

An microsatellite locus consists of a left flank sequence, a number of repeat units, and a right flank sequence. An example of a microsatellite locus is shown below:

(Left flank nucleotide sequence)-$(GT)_{24}$-(Right flank nucleotide sequence).

Given that a sample generally contains various repeat unit lengths. The repeat length distribution can be defined as: $R_{S,L}$, where S is sample, L is locus, and R is repeat length distribution.

Accordingly, $R_{S,L}$ can be presented as:

$$R_{S,L} = <n_1, n_2, \ldots n_k>,$$

where $n_1$ is the number of reads that support the presence of i repeat units. For particular locus L, $R_{S,L}$ is quasi-monomorphic for healthy individuals in a population. When instability is present, the average for $R_{S,L}$ shifts significantly from normal background samples. This shift is observed to be at a magnitude larger than shifts caused due to PCR stutter, and is therefore detectable.

FIGS. 1A and 1B are electropherograms showing fragment distribution of microsatellite loci in MSS (FIG. 1A) or MSI (FIG. 1B) cell lines. The bold lines in the electropherograms refer to internal controls, while the lighter colored lines represent the test sample. As can be seen in FIG. 1A (MSS cell line), the MSS test sample and internal control appear to migrate at similar fragment size distributions.

In contrast, the MSI cell line sample at all three microsatellite loci was observed to migrate at a smaller fragment size (i.e., shifting the migration pattern of the MSI test sample to the left) as compared to the internal control. As such, a MSI sample can be distinguished from a MSS samples on the basis of repeat length distribution.

Example 2—Distribution of Average Number of Repeat Units in 64 Microsatellite Loci In this example, a set of 64 microsatellite loci were evaluated from colorectal and endometrial cancer. Cell-free DNA samples from 7 healthy normal subjects, 4 MSS cell lines and 4 MSI cell lines were evaluated. $R_{S,L}$ was computed for each of the fifteen samples.

Box and whisker plots were generated for the average number of repeat units per locus across the 15 samples and separated by sample type (e.g., cfDNA, unstable cell line or stable cell line). The mean of repeat length distribution is provided for each loci and cell type.

Figure 6A:
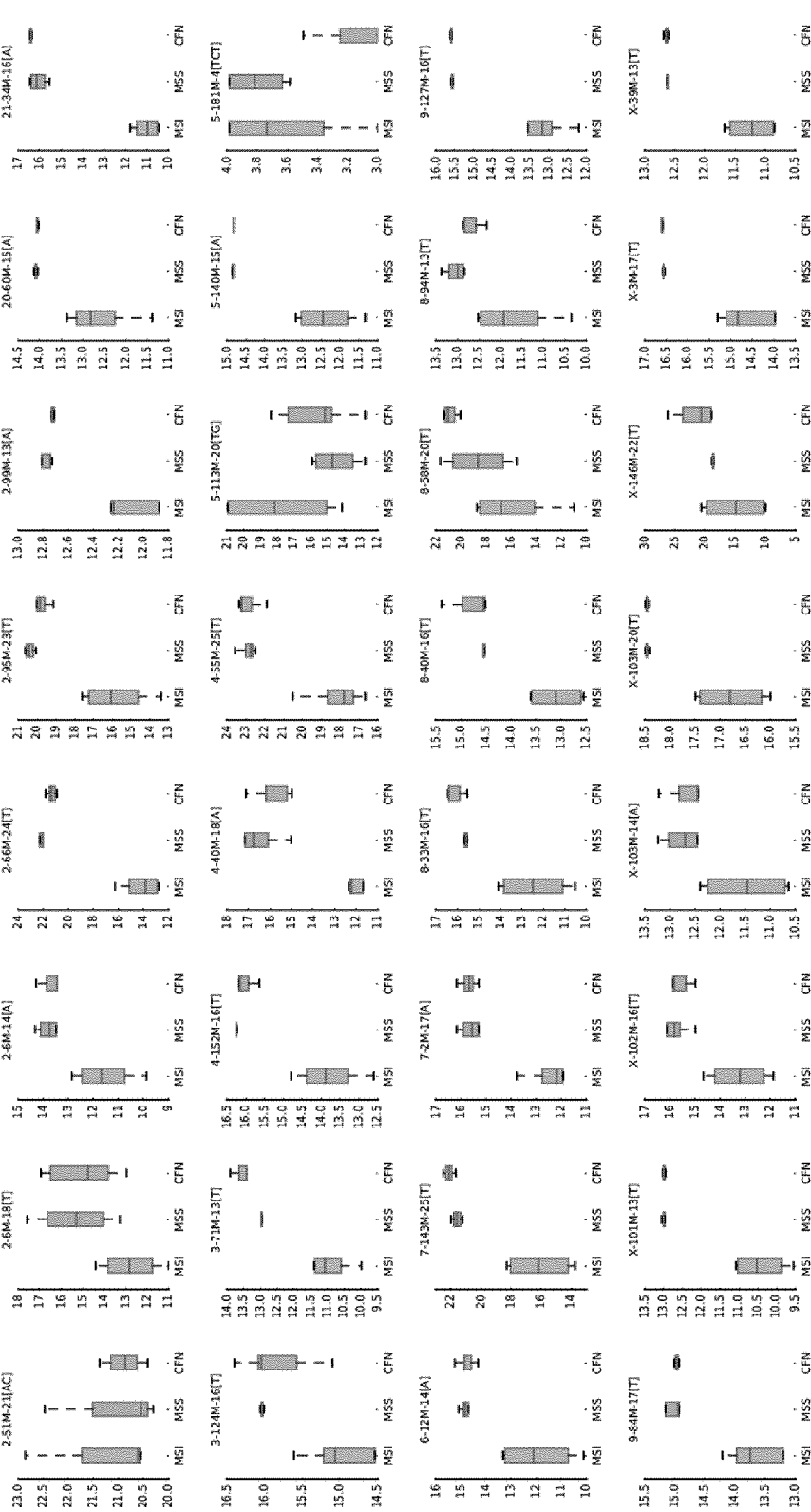
FIGS. 6A and 6B shows box plots of 63 microsatellite loci from cfDNA, MSS samples, and MSI samples, and the distribution of the average number of repeat units in the 63 microsatellite loci.
Figure 6B:
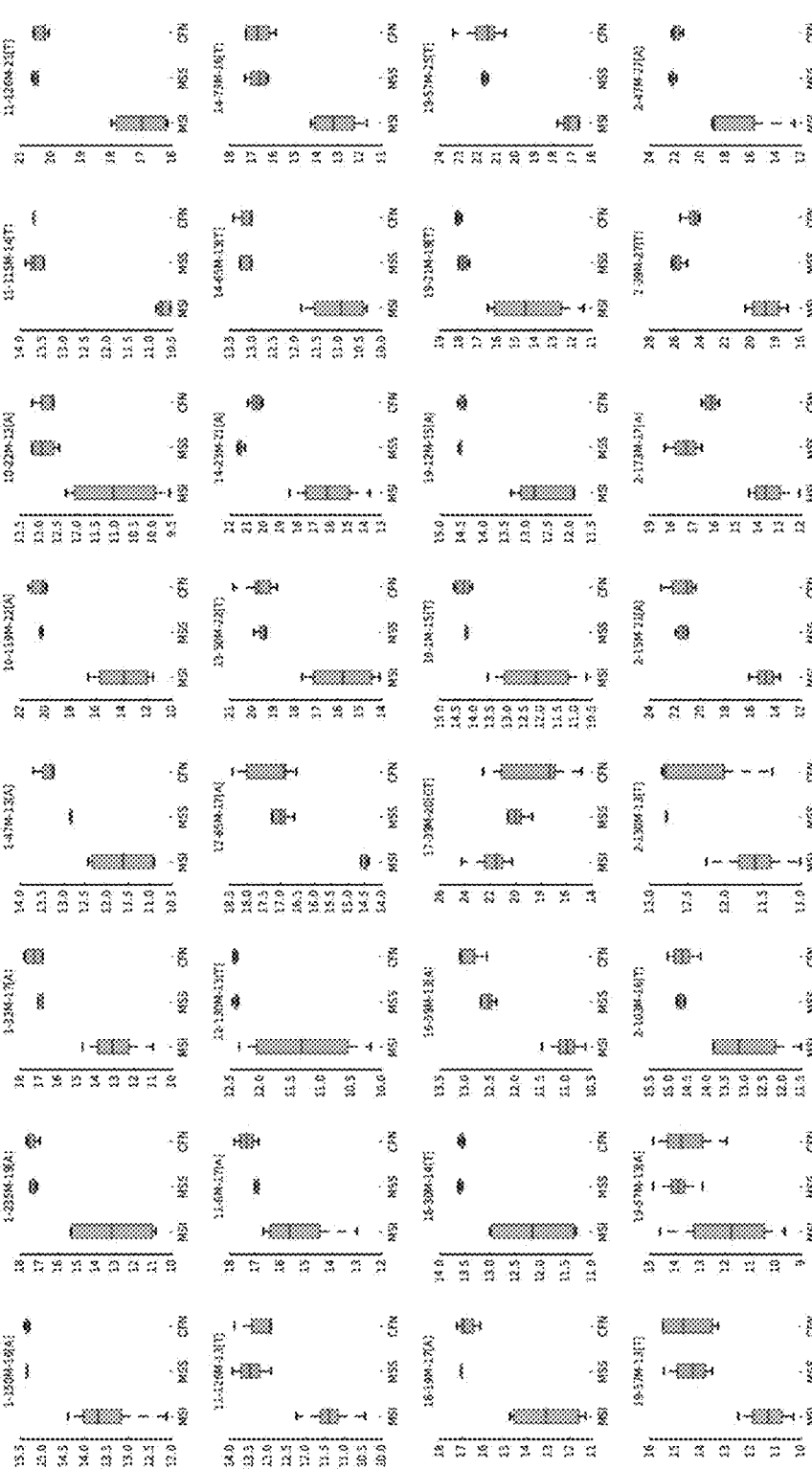

FIGS. 6A and 6B shows a series of 63 plots, each plot corresponds to a unique microsatellite loci. In the cfDNA samples, the number of repeat units per locus is stable and conserved for 58/63 loci. Furthermore, the distribution of the mean number of repeat units for these 58 loci either overlaps fully or is extremely close to the distribution of the mean number of repeat units for samples from the MSS cell lines. As such, this data demonstrates it is possible to calculate a background signal representing MSS samples that can be used as a reference against a test sample. Additionally, the distribution of the mean number of repeat units in the MSI cell lines was observed to be non-overlapping and significantly different from the cfDNA/MSS samples.

Example 3—Skewness as a Component of Repeat Length Distribution

Similar to Example 2, the same 64 loci were evaluated for skewness of the average number of repeat units. Cell-free DNA samples from 7 healthy normal subjects, 4 MSS cell lines and 4 MSI cell lines were evaluated. Skewness was computed for each of the fifteen samples.

Box and whisker plots were generated for the skewness of the average number of repeat units per locus across the 15 samples and separated by sample type (e.g., cfDNA, unstable cell line or stable cell line).

Figure 7A:
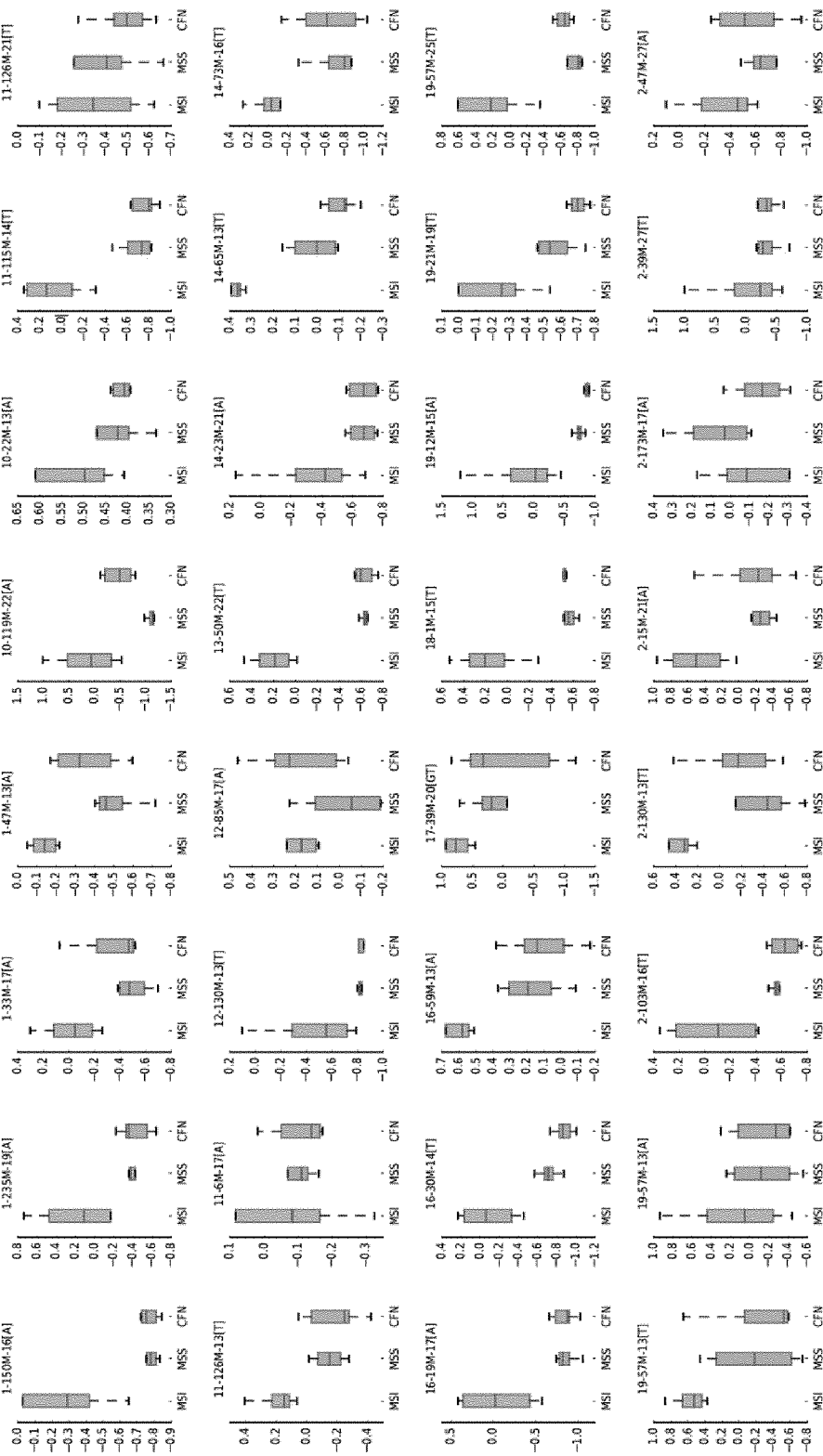
FIGS. 7A and 7B shows box plots of 63 microsatellite loci from cfDNA, MSS samples, and MSI samples, and the distribution of skewness of the average number of repeat units in the 63 microsatellite loci.
Figure 7B:
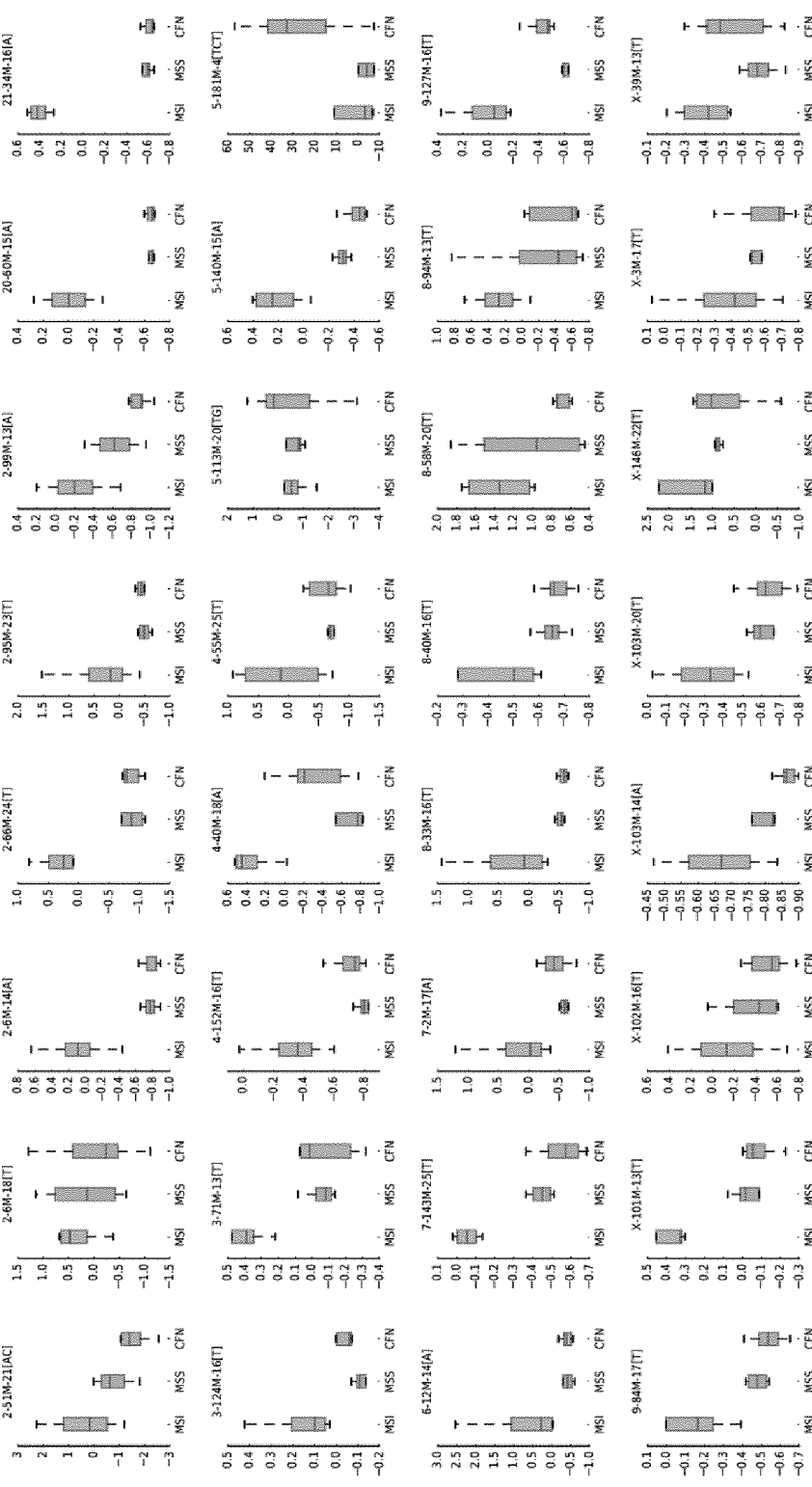

FIGS. 7A and 7B shows a series of 64 plots, each plot corresponds to a unique microsatellite loci. In the cfDNA samples, the skewness of the average number of repeat units per locus is stable and conserved for approximately 37 microsatellite loci. As such, this data demonstrates it is possible to calculate a background signal representing MSS samples that can be used as a reference against a test sample, Additionally, the distribution of the skewness of the average number of repeat units in the MSI cell lines was observed to be non-overlapping and significantly different from the cfDNA/MSS samples.

Example 4—Computation Process for MSI Detection

Detection of microsatellite instability in a sample is based on the MSI-proportion threshold obtained for a set of microsatellite loci. Here, samples are sequenced or sequencing reads are obtained for a sample (e.g., from a sequencing data file or database) that comprise one or more microsatellite loci. A RLD for each DNA fragment comprising a microsatellite locus is determined. Then, a RLD metric is determined for each microsatellite locus. The RLD metric is compared to a threshold value (e.g., a normal background sample for the same microsatellite loci or a pre-computed normal background RLD) and the number of microsatellite loci exceeding the corresponding microsatellite loci threshold values are determined.

Figure 3:
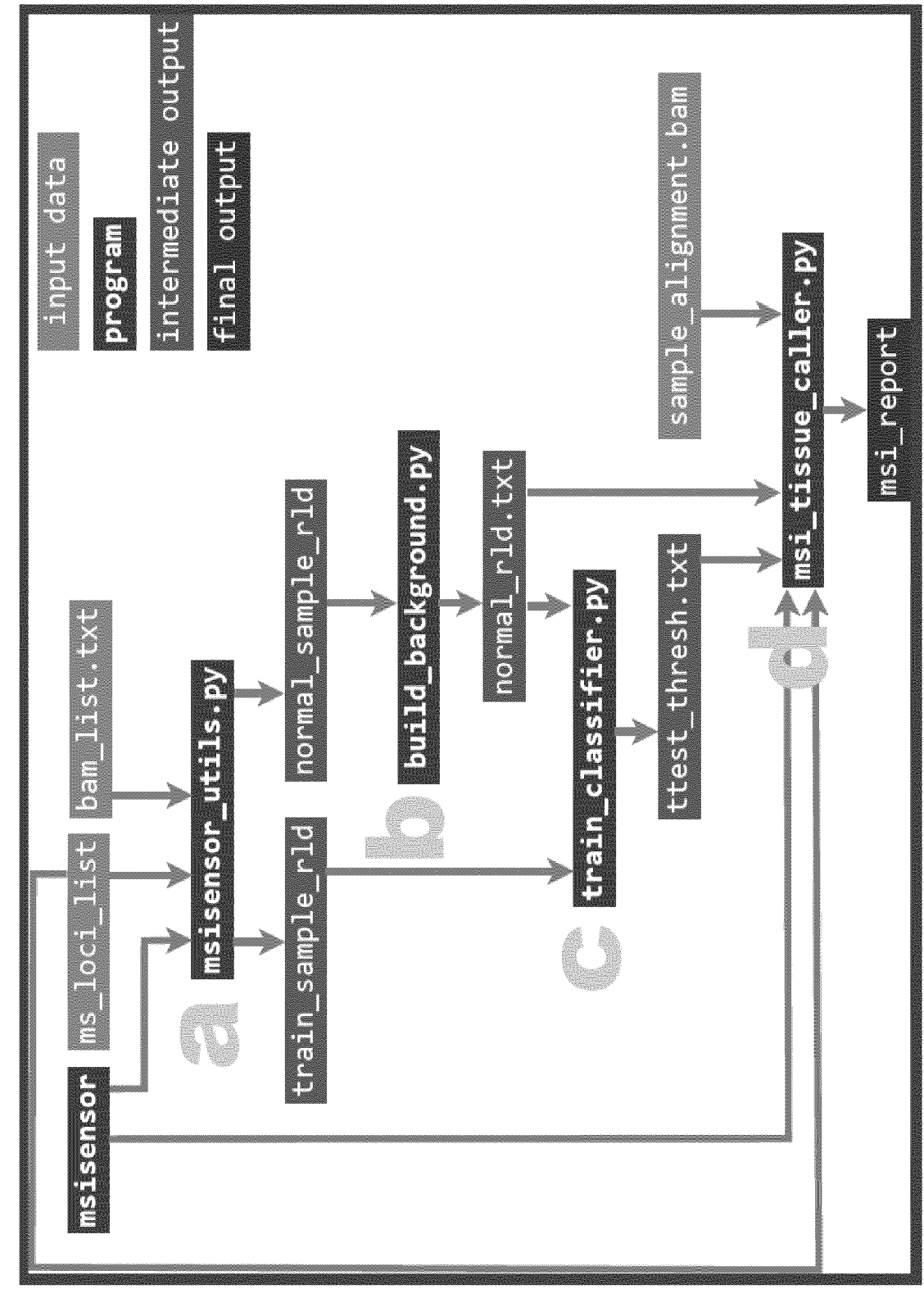
FIG. 3 shows a flowchart containing exemplary steps of the microsatellite instability computational pipeline, including training and prediction steps.

Next, the quantity of microsatellite loci having a RLD metric exceeding the threshold value are compared to an MSI proportion threshold (e.g., 35%). If the quantity of microsatellite loci having a RLD metric exceeding the threshold value is greater than the MSI-PT, the sample is classified as MSI. The above steps can be performed using a computer system to determine the status of MSI or MSS in a sample. An exemplary workflow of such a computer process is set forth in FIG. 3 and is referred to herein as "MSI caller pipeline". The MSI caller pipeline works in four main stages.

First, it uses msisensor (Niu et al. 2013) to summarize RLDs obtained from sequencing read alignments (pathway a)

Second, it selects a set of microsatellite loci that demonstrate conserved RLDs within a set of normal, cell-free DNA samples from healthy donors (pathway b)

Third, for each microsatellite locus, it learns a binarized classifier to identify MSI status from a set of training samples with known microsatellite stability status (pathway c)

Fourth, once a test sample is applied, the computer process determines whether the sample is MSI or MSS (pathway d)

Microsatellite Loci Panel

An exemplary MSI detection panel included 64 microsatellite loci in the referred to herein as microsatellite loci: 1-64 (see, Table 1). These microsatellite loci are known to be informative of microsatellite stability status for colorectal cancer, endometrial and prostate cancers. The initial microsatellite panel was subsequently expanded to a size of 170 loci (see, Table 1, microsatellite loci: 1-170).

Summarizing RLD from Msisensor

The computational pipeline described above uses "msisensor" to calculate RLD with a read alignment file in BAM format. This step typically includes a compiled executable code for msisensor, a microsatellite panel file that defines the locations of the included microsatellite markers, and a BAM file of sequencing read alignments. Msisensor outputs a RLD file which summarizes RLDs of the included microsatellite loci based on the sequencing read alignments.

Background Construction From Normal Samples

Figures 5A, 5B, 5C:
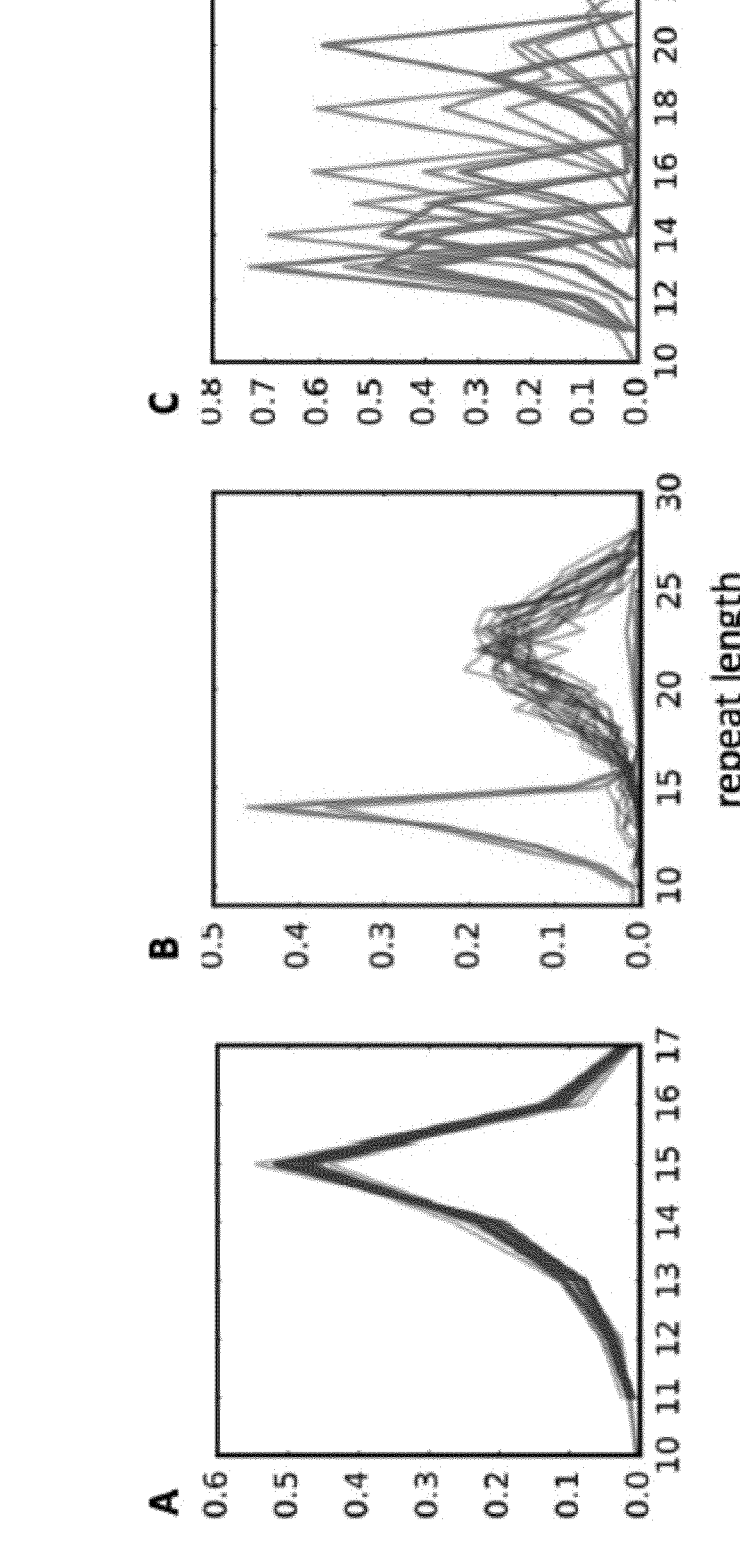
FIGS. 5A-5C are graphs showing variability of RLDs across microsatellite loci.

The MSI caller pipeline can include a pre-computed "normal" RLD value. This works particularly well if the microsatellite locus contains consistent RLDs across microsatellite stable (MSS) samples (e.g. FIG. 5A). We have determined that variability in repeat lengths is largely a side effect of PCR stutter during sequencing, and can be extracted from a set of normal samples. Therefore, we computed the average RLD from a set of normal samples (CFDNA of FIGS. 6A and 6B and FIGS. 7A and 7B) to represent the pre-computed normal background RLD of a given microsatellite locus.

However, variable repeat lengths at heterozygous and homozygous levels (e.g. FIG. 5C) can be caused by real germline variants instead of PCR stutter and thus should be excluded from down-stream analyses. Additionally, for microsatellite loci that are significantly different from the norm (e.g. FIG. 5B) might represent germline variants from a minority group, and thus should be excluded from background.

Inconsistent RLDs across a microsatellite locus can be filtered using distance metrics to measure the similarity between two RLDs. A microsatellite locus is considered to have an inconsistent RLD if more than half of the pair-wise distances from RLDs are "long" of any distance metric tested. As used herein, a RLD is long if it is greater than median plus two standard deviations distances from all paired samples of all microsatellite loci. In some instances, the median is used in preference to the mean to reduce the effect of outliers.

Various distance metrics can be used to evaluate similarities between two RLDs. For example, distance metrics such as: Kullback-Leibler divergence, correlation distance, cosine distance, Euclidean distance, Manhattan distance, and Kolmogorov-Smirnov statistic can be used to evaluate similarities between two RLDs.

When filtering inconsistent samples of a given microsatellite locus, Euclidean distance is may be preferred to measure the similarity between the two RLDs. A sample is considered inconsistent compared to other samples if its Euclidian distance to the normal background sample is great than median plus two standard deviation distances from all samples of all sites.

MSI Caller

The prediction of MSI by the MSI caller pipeline is determined by the percentage or fraction of MSI loci under evaluation that are greater than a defined threshold (i.e., the MSI-PT). The training step of the classifier learns these threshold values from a set of training samples and the MSI caller uses these thresholds to classify the sample as MSI or MSS. The t-statistic is computed as:

$$t = \frac{\overline{\mu_b} - \overline{\mu_f}}{\sqrt{\dfrac{S_f^2 + S_b^2}{n_f}}}.$$

Here, $\mu_f$ and $S_f^2$ are the mean and variance of the sample RLD; while $\mu_b$ and $S_b^2$ are the mean and variance of the background RLD. $n_f$ is the total number of reads in a sample covering a specific microsatellite locus. In one aspect, a max Youden Index is chosen to maximize the difference between true positive and false positive rates.

The normal RLD background samples are prepared from cfDNA from healthy non-cancerous samples. The samples can be filtered using distance metrics described above to reduce variation in RLD between samples (data not shown).

CONCLUSIONS

The inventors have created a computational pipeline that enables detection of MSI status for tissue samples. We expand the existing microsatellite instability detection panel from 5 to 170 and used NGS to massively monitor the MSI status from all markers simultaneously. We eliminated the requirement of a matched normal sample by extracting a common background of the repeat length distribution from healthy samples. The absence of a matched normal sample represents an important advancement in MSI detection, as it removes another form of invasive surgery and associated risks that occur when harvesting the matched normal tissue sample. We also tested our sequencing-based assay and bioinformatics workflow on plasma samples obtained from blood draws, and found our method could classify a sample as MSI or MSS using the plasma sample. These findings represent another significant advancement in that blood draws can be used to detect MSI and/or monitor MSI status prior to, during, and after, a treatment regime. When applied to a large clinical cohort, the MSI score threshold of 35% may be used as guidance for determining MSS/MSI labels for samples.

The sequencing-based assay and bioinformatics workflow presented herein provides a robust analytical performance for MSI detection in FFPE tissue samples and in plasma, even with samples having low circulating tumor DNA (ctDNA) content.

The invention claimed is:

1. A method for treatment, comprising:
   (i) detecting sequencing reads for a plurality of microsatellite loci from a genomic DNA sample derived from a human diagnosed as having colorectal cancer, wherein the genomic DNA sample is cell-free DNA (cfDNA) or circulating tumor DNA (ctDNA), and wherein the sequencing reads are detected using a sequencing device configured to assay for the plurality of the microsatellite loci;
   (ii) determining a metric for repeat length distribution (RLD) for each microsatellite locus;
   (iii) for each microsatellite locus, comparing the RLD metric to a threshold value for the microsatellite locus, wherein each microsatellite has an independent threshold value, wherein the threshold value has been determined by (i) the repeat length distribution of the microsatellite locus in a MSS sample; (ii) the repeat length distribution of the microsatellite locus in a matched normal sample; (iii) the repeat length distribution of the microsatellite locus in a pre-computed normal background; (iv) the repeat length distribution of the microsatellite locus obtained from a MSS cell line; or (v) a RLD metric at which the microsatellite locus is identified as MSI; and
   administering a therapeutically effective amount of at least one antibody and/or at least one small molecule therapeutic agent to an identified human diagnosed as having colorectal cancer and as having microsatellite instability, wherein the identifying of the human diagnosed as having colorectal cancer and as having microsatellite instability comprises: (i) quantifying a number of microsatellite loci having the RLD metric exceeding the threshold value; (ii) comparing the quantified number to a microsatellite instability proportion threshold; and (iii) determining if the quantified number exceeds the microsatellite instability proportion threshold, wherein if the quantified number exceeds the microsatellite instability proportion threshold, the human diagnosed as having colorectal cancer has microsatellite instability;

(iv) wherein the at least one antibody and/or the at least one small molecule is selected from the group consisting of Avastin (Bevacizumab); Bevacizumab; Camptosar (Irinotecan Hydrochloride); Capecitabine; Cetuximab; Cyramza (Ramucirumab); Eloxatin (Oxaliplatin); Erbitux (Cetuximab); 5-FU (Fluorouracil Injection); Irinotecan Hydrochloride; Leucovorin Calcium; Lonsurf (Trifluridine and Tipiracil Hydrochloride); Nivolumab; Opdivo (Nivolumab); Oxaliplatin; Panitumumab; Ramucirumab; Regorafenib; Stivarga (Regorafenib); Trifluridine and Tipiracil Hydrochloride; Vectibix (Panitumumab); Wellcovorin (Leucovorin Calcium); Xeloda (Capecitabine); Zaltrap (Ziv-Aflibercept); and Ziv-Aflibercept; and wherein the plurality of microsatellite loci are at least 10, 20, 30, 40, 50, 60, 70, 80, 90, 100, 110, 120, 130, 140, 150, or 160 microsatellite loci selected from the group consisting of microsatellite loci 1-170:

| microsatellite locus | chromosome location | start coordinate | end coordinate |
| --- | --- | --- | --- |
| 1 | chr1 | 32936733 | 32936750 |
| 2 | chr1 | 46859627 | 46859640 |
| 3 | chr1 | 149929093 | 149929109 |
| 4 | chr1 | 235344151 | 235344170 |
| 5 | chr2 | 5699709 | 5699727 |
| 6 | chr2 | 5700420 | 5700434 |
| 7 | chr2 | 14638213 | 14638234 |
| 8 | chr2 | 39309548 | 39309575 |
| 9 | chr2 | 47414420 | 47414447 |
| 10 | chr2 | 51061373 | 51061415 |
| 11 | chr2 | 66435743 | 66435767 |
| 12 | chr2 | 95183613 | 95183636 |
| 13 | chr2 | 98998132 | 98998145 |
| 14 | chr2 | 102762122 | 102762138 |
| 15 | chr2 | 129982139 | 129982152 |
| 16 | chr2 | 173266783 | 173266800 |
| 17 | chr3 | 70959190 | 70959203 |
| 18 | chr3 | 123614028 | 123614044 |
| 19 | chr4 | 39500102 | 39500120 |
| 20 | chr4 | 54732045 | 54732070 |
| 21 | chr4 | 151662755 | 151662771 |
| 22 | chr5 | 112877981 | 112878021 |
| 23 | chr5 | 140115261 | 140115276 |
| 24 | chr5 | 181260427 | 181260439 |
| 25 | chr6 | 11714406 | 11714420 |
| 26 | chr7 | 1747883 | 1747900 |
| 27 | chr7 | 143306249 | 143306274 |
| 28 | chr8 | 33498673 | 33498689 |
| 29 | chr8 | 40154248 | 40154264 |
| 30 | chr8 | 58148166 | 58148186 |
| 31 | chr8 | 93925321 | 93925334 |
| 32 | chr9 | 84003046 | 84003063 |
| 33 | chr9 | 126837838 | 126837854 |
| 34 | chr10 | 21518540 | 21518553 |
| 35 | chr10 | 119137173 | 119137195 |
| 36 | chr11 | 5666090 | 5666107 |
| 37 | chr11 | 115176312 | 115176326 |
| 38 | chr11 | 125620870 | 125620891 |
| 39 | chr11 | 125893715 | 125893728 |
| 40 | chr12 | 84892141 | 84892158 |
| 41 | chr12 | 130399009 | 130399022 |
| 42 | chr13 | 50013518 | 50013540 |
| 43 | chr14 | 23183137 | 23183158 |
| 44 | chr14 | 64523982 | 64523995 |
| 45 | chr14 | 73492999 | 73493015 |

-continued

| microsatellite locus | chromosome location | start coordinate | end coordinate |
| --- | --- | --- | --- |
| 46 | chr16 | 19118464 | 19118481 |
| 47 | chr16 | 29669203 | 29669217 |
| 48 | chr16 | 58543411 | 58543424 |
| 49 | chr17 | 38995870 | 38995910 |
| 50 | chr18 | 649879 | 649894 |
| 51 | chr19 | 11808381 | 11808396 |
| 52 | chr19 | 21378606 | 21378625 |
| 53 | chr19 | 57257698 | 57257723 |
| 54 | chr19 | 57258437 | 57258450 |
| 55 | chr19 | 57262350 | 57262363 |
| 56 | chr20 | 59922426 | 59922441 |
| 57 | chr21 | 34103315 | 34103331 |
| 58 | chrX | 2904903 | 2904920 |
| 59 | chrX | 38805564 | 38805577 |
| 60 | chrX | 101413944 | 101413957 |
| 61 | chrX | 102154282 | 102154298 |
| 62 | chrX | 102658669 | 102658683 |
| 63 | chrX | 102751949 | 102751969 |
| 64 | chrX | 145825169 | 145825191 |
| 65 | chr1 | 103663067 | 103663077 |
| 66 | chr1 | 103757205 | 103757215 |
| 67 | chr1 | 116112562 | 116112575 |
| 68 | chr1 | 13782253 | 13782262 |
| 69 | chr1 | 150714123 | 150714133 |
| 70 | chr1 | 151224226 | 151224235 |
| 71 | chr1 | 159062696 | 159062706 |
| 72 | chr1 | 200624913 | 200624921 |
| 73 | chr1 | 221702319 | 221702330 |
| 74 | chr1 | 236897645 | 236897660 |
| 75 | chr1 | 28459218 | 28459228 |
| 76 | chr1 | 52784862 | 52784872 |
| 77 | chr1 | 88983825 | 88983836 |
| 78 | chr10 | 72893710 | 72893720 |
| 79 | chr11 | 105007313 | 105007323 |
| 80 | chr11 | 105008959 | 105008969 |
| 81 | chr11 | 120479927 | 120479935 |
| 82 | chr11 | 63382198 | 63382209 |
| 83 | chr11 | 65501008 | 65501020 |
| 84 | chr12 | 118150956 | 118150974 |
| 85 | chr12 | 119728455 | 119728465 |
| 86 | chr12 | 13211492 | 13211502 |
| 87 | chr12 | 31282674 | 31282685 |
| 88 | chr12 | 54011395 | 54011406 |
| 89 | chr12 | 96286155 | 96286166 |
| 90 | chr13 | 46771334 | 46771348 |
| 91 | chr13 | 49350729 | 49350739 |
| 92 | chr13 | 57725300 | 57725311 |
| 93 | chr14 | 19668967 | 19668978 |
| 94 | chr14 | 53046721 | 53046733 |
| 95 | chr15 | 30113885 | 30113899 |
| 96 | chr15 | 37099551 | 37099563 |
| 97 | chr15 | 41852769 | 41852780 |
| 98 | chr15 | 72572067 | 72572077 |
| 99 | chr16 | 14889234 | 14889243 |
| 100 | chr17 | 1423460 | 1423474 |
| 101 | chr17 | 4539344 | 4539362 |
| 102 | chr17 | 45539269 | 45539279 |
| 103 | chr17 | 46306192 | 46306202 |
| 104 | chr17 | 46523767 | 46523777 |
| 105 | chr17 | 56938993 | 56939007 |
| 106 | chr17 | 58357799 | 58357806 |
| 107 | chr18 | 23529756 | 23529766 |
| 108 | chr18 | 319944 | 319955 |
| 109 | chr18 | 33333178 | 33333188 |
| 110 | chr18 | 9954236 | 9954249 |
| 111 | chr19 | 12463926 | 12463947 |
| 112 | chr19 | 13993876 | 13993890 |
| 113 | chr19 | 44158121 | 44158134 |
| 114 | chr19 | 9251064 | 9251075 |
| 115 | chr2 | 106426090 | 106426102 |
| 116 | chr2 | 108729222 | 108729232 |
| 117 | chr2 | 118096518 | 118096531 |
| 118 | chr2 | 147926116 | 147926124 |
| 119 | chr2 | 151379531 | 151379545 |
| 120 | chr2 | 182942165 | 182942175 |
| 121 | chr2 | 196666794 | 196666805 |

-continued

| microsatellite locus | chromosome location | start coordinate | end coordinate |
|---|---|---|---|
| 122 | chr2 | 202300378 | 202300388 |
| 123 | chr2 | 210315041 | 210315052 |
| 124 | chr2 | 55234233 | 55234243 |
| 125 | chr2 | 63842143 | 63842158 |
| 126 | chr2 | 87757451 | 87757462 |
| 127 | chr2 | 8858645 | 8858657 |
| 128 | chr20 | 53875234 | 53875245 |
| 129 | chr20 | 60012728 | 60012738 |
| 130 | chr21 | 28966883 | 28966894 |
| 131 | chr21 | 32601784 | 32601798 |
| 132 | chr22 | 38683915 | 38683930 |
| 133 | chr3 | 101459057 | 101459067 |
| 134 | chr3 | 113658634 | 113658645 |
| 135 | chr3 | 131014202 | 131014213 |
| 136 | chr3 | 165187860 | 165187871 |
| 137 | chr3 | 170997894 | 170997904 |
| 138 | chr3 | 25719646 | 25719656 |
| 139 | chr3 | 30650379 | 30650389 |
| 140 | chr3 | 51380172 | 51380179 |
| 141 | chr5 | 159099526 | 159099541 |
| 142 | chr5 | 162067984 | 162067996 |
| 143 | chr5 | 177302735 | 177302747 |
| 144 | chr5 | 58974630 | 58974642 |
| 145 | chr5 | 68288684 | 68288696 |
| 146 | chr5 | 78450039 | 78450050 |
| 147 | chr5 | 80675095 | 80675103 |
| 148 | chr5 | 83641432 | 83641442 |
| 149 | chr5 | 88722571 | 88722584 |
| 150 | chr6 | 167040031 | 167040043 |
| 151 | chr6 | 43054238 | 43054250 |
| 152 | chr6 | 49492281 | 49492291 |
| 153 | chr6 | 55874913 | 55874927 |
| 154 | chr6 | 70861991 | 70862003 |
| 155 | chr6 | 88143811 | 88143822 |
| 156 | chr7 | 135619945 | 135619955 |
| 157 | chr7 | 30633896 | 30633911 |
| 158 | chr7 | 54752300 | 54752311 |
| 159 | chr7 | 75193019 | 75193032 |
| 160 | chr7 | 95359943 | 95359960 |
| 161 | chr8 | 23854553 | 23854565 |
| 162 | chr8 | 33499307 | 33499320 |
| 163 | chr8 | 39103749 | 39103760 |
| 164 | chr8 | 7489344 | 7489353 |
| 165 | chr8 | 7822205 | 7822214 |
| 166 | chr8 | 78717503 | 78717517 |
| 167 | chr9 | 107331689 | 107331701 |
| 168 | chr9 | 83969307 | 83969318 |
| 169 | chrX | 101883466 | 101883477 |
| 170 | chrX | 18164977 | 18164992 |

2. The method of claim 1, wherein the plurality of microsatellite loci are at least 58 microsatellite loci selected from the group consisting of microsatellite loci: 1-64.

3. The method of claim 1, wherein the plurality of microsatellite loci corresponds to the microsatellite loci:

| Chr. | Coordinate | Coordinate |
|---|---|---|
| chr1 | 149929093 | 149929109 |
| chr1 | 235344151 | 235344170 |
| chr1 | 32936733 | 32936750 |
| chr1 | 46859627 | 46859640 |
| chr10 | 119137173 | 119137195 |
| chr10 | 21518540 | 21518553 |
| chr11 | 115176312 | 115176326 |
| chr11 | 125620870 | 125620891 |
| chr11 | 125893715 | 125893728 |
| chr11 | 5666090 | 5666107 |
| chr12 | 130399009 | 130399022 |
| chr12 | 84892141 | 84892158 |
| chr13 | 50013518 | 50013540 |
| chr14 | 23183137 | 23183158 |
| chr14 | 64523982 | 64523995 |

-continued

| Chr. | Coordinate | Coordinate |
|---|---|---|
| chr14 | 73492999 | 73493015 |
| chr16 | 19118464 | 19118481 |
| chr16 | 29669203 | 29669217 |
| chr16 | 58543411 | 58543424 |
| chr18 | 649879 | 649894 |
| chr19 | 11808381 | 11808396 |
| chr19 | 21378606 | 21378625 |
| chr19 | 57257698 | 57257723 |
| chr19 | 57258437 | 57258450 |
| chr19 | 57262350 | 57262363 |
| chr2 | 102762122 | 102762138 |
| chr2 | 129982139 | 129982152 |
| chr2 | 14638213 | 14638234 |
| chr2 | 173266783 | 173266800 |
| chr2 | 39309548 | 39309575 |
| chr2 | 47414420 | 47414447 |
| chr2 | 5700420 | 5700434 |
| chr2 | 66435743 | 66435767 |
| chr2 | 95183613 | 95183636 |
| chr2 | 98998132 | 98998145 |
| chr20 | 59922426 | 59922441 |
| chr21 | 34103315 | 34103331 |
| chr3 | 123614028 | 123614044 |
| chr3 | 70959190 | 70959203 |
| chr4 | 151662755 | 151662771 |
| chr4 | 39500102 | 39500120 |
| chr4 | 54732045 | 54732070 |
| chr5 | 140115261 | 140115276 |
| chr6 | 11714406 | 11714420 |
| chr7 | 143306249 | 143306274 |
| chr7 | 1747883 | 1747900 |
| chr8 | 33498673 | 33498689 |
| chr8 | 40154248 | 40154264 |
| chr8 | 93925321 | 93925334 |
| chr9 | 126837838 | 126837854 |
| chr9 | 84003046 | 84003063 |
| chrX | 101413944 | 101413957 |
| chrX | 102154282 | 102154298 |
| chrX | 102658669 | 102658683 |
| chrX | 102751949 | 102751969 |
| chrX | 145825169 | 145825191 |
| chrX | 2904903 | 2904920 |
| chrX | 38805564 | 38805577. |

4. The method of claim 1, wherein the metric for RLD is determined in the absence of a matched normal sample.

5. The method of claim 1, wherein the metric of a microsatellite locus is a t-statistic determined using one or more statistical values of the RLD of the human for the microsatellite locus and one or more statistical values of a reference RLD.

6. The method of claim 5, wherein the t-statistic is determined based on mean read length and variance in the RLD.

7. The method of claim 1, wherein the detecting comprises generating nucleotide sequencing reads from the genomic DNA sample and identifying sequencing reads comprising a microsatellite locus by alignment of the sequencing reads to a set of microsatellite loci DNA sequences; and counting the number of repeat lengths for each sequencing read determined to comprise a microsatellite locus, thereby generating an RLD for each microsatellite locus.

8. The method of claim 7, wherein prior to generating nucleotide sequencing reads, the human genomic DNA is enriched for microsatellite loci by hybridizing the human genomic DNA to oligonucleotide probes that hybridize to microsatellite locus-containing DNA.

9. The method of claim 1, further comprising:
(i) providing a sample comprising the human genomic DNA fragments; contacting a pool of oligonucleotide probes to the sample;

(ii) capturing DNA fragments comprising microsatellite loci in hybridization complexes with the pool oligonucleotide probes, thereby generating captured DNA;

(iii) separating the hybridization complexes from unbound nucleic acids; eluting the captured DNA from the hybridization complexes;

(iv) sequencing the captured DNA that was eluted from the hybridization complexes;

(v) identifying sequencing reads comprising a microsatellite locus by alignment of the sequencing reads to a set of microsatellite loci DNA sequences; and (vi) counting the number of repeat lengths for each sequencing read determined to comprise a microsatellite locus, thereby generating an RID for each microsatellite locus.

10. The method of claim 1, further comprising:

(i) providing a sample comprising the human genomic DNA fragments;

(ii) amplifying DNA fragments comprising microsatellite loci with oligonucleotide primers specific for a microsatellite locus to produce amplicons;

(iii) sequencing the amplicons;

(iv) identifying sequencing reads comprising a microsatellite locus by alignment of the sequencing reads to a set of microsatellite loci DNA sequences; and (v) counting the number of repeat lengths for each sequencing read determined to comprise a microsatellite locus, thereby generating an RLD for each microsatellite locus.

11. The method of claim 1, wherein the human is treated with at least two antibodies and/or at least two small molecule therapeutic agents.

12. A method of treatment, comprising:

(i) generating sequencing reads for a plurality of microsatellite loci from a genomic DNA sample derived from a human diagnosed as having colorectal cancer, wherein the genomic DNA sample is cell-free DNA (cfDNA) or circulating tumor DNA (ctDNA), and wherein the sequencing reads are generated using a sequencing device configured to assay for the plurality of the microsatellite loci;

(ii) determining a repeat length distribution (RLD) for each microsatellite locus;

(iii) generating a metric for the RLD for each microsatellite locus;

(iv) for each microsatellite locus, comparing the RLD metric for each microsatellite locus to a threshold value for the microsatellite locus, wherein each microsatellite has an independent threshold value, wherein the threshold value has been determined by (i) the repeat length distribution of the microsatellite locus in a MSS sample; or (ii) the repeat length distribution of the microsatellite locus in a matched normal sample; or (iii) the repeat length distribution of the microsatellite locus in a pre-computed normal background; or (iv) the repeat length distribution of the microsatellite locus obtained from a MSS cell line; or (v) a RLD metric at which the microsatellite locus is identified as MSI; and (v) administering a therapeutically effective amount of at least one antibody and/or at least one small molecule therapeutic agent to an identified human diagnosed as having colorectal cancer and as having microsatellite instability, wherein the identifying of the human diagnosed as having colorectal cancer and as having microsatellite instability comprises: (i) quantifying a number of detected loci having an RLD metric exceeding the threshold value, (ii) by comparing the quantified number to a locus set proportion threshold; and (iii) determining if the quantified number exceeds the locus set proportion threshold, wherein if the quantified number exceeds the locus set proportion threshold, the human diagnosed as having colorectal cancer has microsatellite instability;

wherein the at least one antibody and/or the at least one small molecule is selected from the group consisting of Avastin (Bevacizumab); Bevacizumab; Camptosar (Irinotecan Hydrochloride); Capecitabine; Cetuximab; Cyramza (Ramucirumab); Eloxatin (Oxaliplatin); Erbitux (Cetuximab); 5-FU (Fluorouracil Injection); Irinotecan Hydrochloride; Leucovorin Calcium; Lonsurf (Trifluridine and Tipiracil Hydrochloride); Nivolumab; Opdivo (Nivolumab); Oxaliplatin; Panitumumab; Ramucirumab; Regorafenib; Stivarga (Regorafenib); Trifluridine and Tipiracil Hydrochloride; Vectibix (Panitumumab); Wellcovorin (Leucovorin Calcium); Xeloda (Capecitabine); Zaltrap (Ziv-Aflibercept); and Ziv-Aflibercept; and wherein the plurality of microsatellite loci are at least 10, 20, 30, 40, 50, 60, 70, 80, 90, 100, 110, 120, 130, 140, 150, or 160 microsatellite loci selected from the group consisting of microsatellite loci 1-170:

| microsatellite locus | chromosome location | start coordinate | end coordinate |
|---|---|---|---|
| 1 | chr1 | 32936733 | 32936750 |
| 2 | chr1 | 46859627 | 46859640 |
| 3 | chr1 | 149929093 | 149929109 |
| 4 | chr1 | 235344151 | 235344170 |
| 5 | chr2 | 5699709 | 5699727 |
| 6 | chr2 | 5700420 | 5700434 |
| 7 | chr2 | 14638213 | 14638234 |
| 8 | chr2 | 39309548 | 39309575 |
| 9 | chr2 | 47414420 | 47414447 |
| 10 | chr2 | 51061373 | 51061415 |
| 11 | chr2 | 66435743 | 66435767 |
| 12 | chr2 | 95183613 | 95183636 |
| 13 | chr2 | 98998132 | 98998145 |
| 14 | chr2 | 102762122 | 102762138 |
| 15 | chr2 | 129982139 | 129982152 |
| 16 | chr2 | 173266783 | 173266800 |
| 17 | chr3 | 70959190 | 70959203 |
| 18 | chr3 | 123614028 | 123614044 |
| 19 | chr4 | 39500102 | 39500120 |
| 20 | chr4 | 54732045 | 54732070 |
| 21 | chr4 | 151662755 | 151662771 |
| 22 | chr5 | 112877981 | 112878021 |
| 23 | chr5 | 140115261 | 140115276 |
| 24 | chr5 | 181260427 | 181260439 |
| 25 | chr6 | 11714406 | 11714420 |
| 26 | chr7 | 1747883 | 1747900 |
| 27 | chr7 | 143306249 | 143306274 |
| 28 | chr8 | 33498673 | 33498689 |
| 29 | chr8 | 40154248 | 40154264 |
| 30 | chr8 | 58148166 | 58148186 |
| 31 | chr8 | 93925321 | 93925334 |
| 32 | chr9 | 84003046 | 84003063 |
| 33 | chr9 | 126837838 | 126837854 |
| 34 | chr10 | 21518540 | 21518553 |
| 35 | chr10 | 119137173 | 119137195 |
| 36 | chr11 | 5666090 | 5666107 |
| 37 | chr11 | 115176312 | 115176326 |
| 38 | chr11 | 125620870 | 125620891 |
| 39 | chr11 | 125893715 | 125893728 |
| 40 | chr12 | 84892141 | 84892158 |
| 41 | chr12 | 130399009 | 130399022 |
| 42 | chr13 | 50013518 | 50013540 |
| 43 | chr14 | 23183137 | 23183158 |
| 44 | chr14 | 64523982 | 64523995 |
| 45 | chr14 | 73492999 | 73493015 |
| 46 | chr16 | 19118464 | 19118481 |
| 47 | chr16 | 29669203 | 29669217 |
| 48 | chr16 | 58543411 | 58543424 |

-continued

| microsatellite locus | chromosome location | start coordinate | end coordinate |
|---|---|---|---|
| 49 | chr17 | 38995870 | 38995910 |
| 50 | chr18 | 649879 | 649894 |
| 51 | chr19 | 11808381 | 11808396 |
| 52 | chr19 | 21378606 | 21378625 |
| 53 | chr19 | 57257698 | 57257723 |
| 54 | chr19 | 57258437 | 57258450 |
| 55 | chr19 | 57262350 | 57262363 |
| 56 | chr20 | 59922426 | 59922441 |
| 57 | chr21 | 34103315 | 34103331 |
| 58 | chrX | 2904903 | 2904920 |
| 59 | chrX | 38805564 | 38805577 |
| 60 | chrX | 101413944 | 101413957 |
| 61 | chrX | 102154282 | 102154298 |
| 62 | chrX | 102658669 | 102658683 |
| 63 | chrX | 102751949 | 102751969 |
| 64 | chrX | 145825169 | 145825191 |
| 65 | chr1 | 103663067 | 103663077 |
| 66 | chr1 | 103757205 | 103757215 |
| 67 | chr1 | 116112562 | 116112575 |
| 68 | chr1 | 13782253 | 13782262 |
| 69 | chr1 | 150714123 | 150714133 |
| 70 | chr1 | 151224226 | 151224235 |
| 71 | chr1 | 159062696 | 159062706 |
| 72 | chr1 | 200624913 | 200624921 |
| 73 | chr1 | 221702319 | 221702330 |
| 74 | chr1 | 236897645 | 236897660 |
| 75 | chr1 | 28459218 | 28459228 |
| 76 | chr1 | 52784862 | 52784872 |
| 77 | chr1 | 88983825 | 88983836 |
| 78 | chr10 | 72893710 | 72893720 |
| 79 | chr11 | 105007313 | 105007323 |
| 80 | chr11 | 105008959 | 105008969 |
| 81 | chr11 | 120479927 | 120479935 |
| 82 | chr11 | 63382198 | 63382209 |
| 83 | chr11 | 65501008 | 65501020 |
| 84 | chr12 | 118150956 | 118150974 |
| 85 | chr12 | 119728455 | 119728465 |
| 86 | chr12 | 13211492 | 13211502 |
| 87 | chr12 | 31282674 | 31282685 |
| 88 | chr12 | 54011395 | 54011406 |
| 89 | chr12 | 96286155 | 96286166 |
| 90 | chr13 | 46771334 | 46771348 |
| 91 | chr13 | 49350729 | 49350739 |
| 92 | chr13 | 57725300 | 57725311 |
| 93 | chr14 | 19668967 | 19668978 |
| 94 | chr14 | 53046721 | 53046733 |
| 95 | chr15 | 30113885 | 30113899 |
| 96 | chr15 | 37099551 | 37099563 |
| 97 | chr15 | 41852769 | 41852780 |
| 98 | chr15 | 72572067 | 72572077 |
| 99 | chr16 | 14889234 | 14889243 |
| 100 | chr17 | 1423460 | 1423474 |
| 101 | chr17 | 4539344 | 4539362 |
| 102 | chr17 | 45539269 | 45539279 |
| 103 | chr17 | 46306192 | 46306202 |
| 104 | chr17 | 46523767 | 46523777 |
| 105 | chr17 | 56938993 | 56939007 |
| 106 | chr17 | 58357799 | 58357806 |
| 107 | chr18 | 23529756 | 23529766 |
| 108 | chr18 | 319944 | 319955 |
| 109 | chr18 | 33333178 | 33333188 |
| 110 | chr18 | 9954236 | 9954249 |
| 111 | chr19 | 12463926 | 12463947 |
| 112 | chr19 | 13993876 | 13993890 |
| 113 | chr19 | 44158121 | 44158134 |
| 114 | chr19 | 9251064 | 9251075 |
| 115 | chr2 | 106426090 | 106426102 |
| 116 | chr2 | 108729222 | 108729232 |
| 117 | chr2 | 118096518 | 118096531 |
| 118 | chr2 | 147926116 | 147926124 |
| 119 | chr2 | 151379531 | 151379545 |
| 120 | chr2 | 182942165 | 182942175 |
| 121 | chr2 | 196666794 | 196666805 |
| 122 | chr2 | 202300378 | 202300388 |
| 123 | chr2 | 210315041 | 210315052 |
| 124 | chr2 | 55234233 | 55234243 |

-continued

| microsatellite locus | chromosome location | start coordinate | end coordinate |
|---|---|---|---|
| 125 | chr2 | 63842143 | 63842158 |
| 126 | chr2 | 87757451 | 87757462 |
| 127 | chr2 | 8858645 | 8858657 |
| 128 | chr20 | 53875234 | 53875245 |
| 129 | chr20 | 60012728 | 60012738 |
| 130 | chr21 | 28966883 | 28966894 |
| 131 | chr21 | 32601784 | 32601798 |
| 132 | chr22 | 38683915 | 38683930 |
| 133 | chr3 | 101459057 | 101459067 |
| 134 | chr3 | 113658634 | 113658645 |
| 135 | chr3 | 131014202 | 131014213 |
| 136 | chr3 | 165187860 | 165187871 |
| 137 | chr3 | 170997894 | 170997904 |
| 138 | chr3 | 25719646 | 25719656 |
| 139 | chr3 | 30650379 | 30650389 |
| 140 | chr3 | 51380172 | 51380179 |
| 141 | chr5 | 159099526 | 159099541 |
| 142 | chr5 | 162067984 | 162067996 |
| 143 | chr5 | 177302735 | 177302747 |
| 144 | chr5 | 58974630 | 58974642 |
| 145 | chr5 | 68288684 | 68288696 |
| 146 | chr5 | 78450039 | 78450050 |
| 147 | chr5 | 80675095 | 80675103 |
| 148 | chr5 | 83641432 | 83641442 |
| 149 | chr5 | 88722571 | 88722584 |
| 150 | chr6 | 167040031 | 167040043 |
| 151 | chr6 | 43054238 | 43054250 |
| 152 | chr6 | 49492281 | 49492291 |
| 153 | chr6 | 55874913 | 55874927 |
| 154 | chr6 | 70861991 | 70862003 |
| 155 | chr6 | 88143811 | 88143822 |
| 156 | chr7 | 135619945 | 135619955 |
| 157 | chr7 | 30633896 | 30633911 |
| 158 | chr7 | 54752300 | 54752311 |
| 159 | chr7 | 75193019 | 75193032 |
| 160 | chr7 | 95359943 | 95359960 |
| 161 | chr8 | 23854553 | 23854565 |
| 162 | chr8 | 33499307 | 33499320 |
| 163 | chr8 | 39103749 | 39103760 |
| 164 | chr8 | 7489344 | 7489353 |
| 165 | chr8 | 7822205 | 7822214 |
| 166 | chr8 | 78717503 | 78717517 |
| 167 | chr9 | 107331689 | 107331701 |
| 168 | chr9 | 83969307 | 83969318 |
| 169 | chrX | 101883466 | 101883477 |
| 170 | chrX | 18164977 | 18164992 |

13. The method of claim 1, wherein the sequencing device is a nanopore sequencing device.

14. The method of claim 12, wherein the plurality of microsatellite loci are at least 58 microsatellite loci selected from the group consisting of microsatellite loci: 1-64.

15. The method of claim 12, wherein the plurality of microsatellite loci corresponds to the microsatellite loci:

| Chr. | Coordinate | Coordinate |
|---|---|---|
| chr1 | 149929093 | 149929109 |
| chr1 | 235344151 | 235344170 |
| chr1 | 32936733 | 32936750 |
| chr1 | 46859627 | 46859640 |
| chr10 | 119137173 | 119137195 |
| chr10 | 21518540 | 21518553 |
| chr11 | 115176312 | 115176326 |
| chr11 | 125620870 | 125620891 |
| chr11 | 125893715 | 125893728 |
| chr11 | 5666090 | 5666107 |
| chr12 | 130399009 | 130399022 |
| chr12 | 84892141 | 84892158 |
| chr13 | 50013518 | 50013540 |
| chr14 | 23183137 | 23183158 |
| chr14 | 64523982 | 64523995 |
| chr14 | 73492999 | 73493015 |

57

-continued

| Chr. | Coordinate | Coordinate |
|---|---|---|
| chr16 | 19118464 | 19118481 |
| chr16 | 29669203 | 29669217 |
| chr16 | 58543411 | 58543424 |
| chr18 | 649879 | 649894 |
| chr19 | 11808381 | 11808396 |
| chr19 | 21378606 | 21378625 |
| chr19 | 57257698 | 57257723 |
| chr19 | 57258437 | 57258450 |
| chr19 | 57262350 | 57262363 |
| chr2 | 102762122 | 102762138 |
| chr2 | 129982139 | 129982152 |
| chr2 | 14638213 | 14638234 |
| chr2 | 173266783 | 173266800 |
| chr2 | 39309548 | 39309575 |
| chr2 | 47414420 | 47414447 |
| chr2 | 5700420 | 5700434 |
| chr2 | 66435743 | 66435767 |
| chr2 | 95183613 | 95183636 |
| chr2 | 98998132 | 98998145 |
| chr20 | 59922426 | 59922441 |
| chr21 | 34103315 | 34103331 |
| chr3 | 123614028 | 123614044 |
| chr3 | 70959190 | 70959203 |
| chr4 | 151662755 | 151662771 |
| chr4 | 39500102 | 39500120 |
| chr4 | 54732045 | 54732070 |
| chr5 | 140115261 | 140115276 |
| chr6 | 11714406 | 11714420 |
| chr7 | 143306249 | 143306274 |
| chr7 | 1747883 | 1747900 |
| chr8 | 33498673 | 33498689 |
| chr8 | 40154248 | 40154264 |
| chr8 | 93925321 | 93925334 |
| chr9 | 126837838 | 126837854 |
| chr9 | 84003046 | 84003063 |
| chrX | 101413944 | 101413957 |
| chrX | 102154282 | 102154298 |
| chrX | 102658669 | 102658683 |
| chrX | 102751949 | 102751969 |
| chrX | 145825169 | 145825191 |
| chrX | 2904903 | 2904920 |
| chrX | 38805564 | 38805577. |

16. A method of treatment, comprising:

(i) preparing a nucleic acid library for sequencing, wherein the nucleic acid library for sequencing is enriched for a plurality of microsatellite loci, wherein the nucleic acid library enriched for the plurality of microsatellite loci is prepared by capturing DNA fragments from a sample derived from a human diagnosed as having colorectal cancer with a plurality of oligonucleotide probes that specifically hybridize to microsatellite loci, wherein the genomic DNA sample is cell-free DNA (cfDNA) or circulating tumor DNA (ctDNA);

(ii) sequencing the prepared nucleic acid library with a sequencing device to provide a sequence data set;

(iii) detecting sequencing reads within the sequence data set for the plurality of microsatellite loci;

(iv) determining a metric for repeat length distribution (RLD) for each microsatellite locus of the plurality of microsatellite loci;

(v) for each microsatellite locus, comparing the RLD metric to a threshold value for the microsatellite locus, wherein each microsatellite has an independent threshold value, wherein the threshold value has been determined by (i) the repeat length distribution of the microsatellite locus in a MSS sample; or (ii) the repeat length distribution of the microsatellite locus in a matched normal sample; or (iii) the repeat length distribution of the microsatellite locus in a pre-computed normal background; or (iv) the repeat length distribution of the microsatellite locus obtained from a MSS cell line; or (v) a RLD metric at which the microsatellite locus is identified as MSI; and (vi) administering a therapeutically effective amount of at least one antibody and/or at least one small molecule therapeutic agent to an identified human diagnosed as having colorectal cancer and as having microsatellite instability, wherein the identifying of the human diagnosed as having colorectal cancer and as having microsatellite instability comprises: (i) quantifying a number of microsatellite loci having an RLD metric exceeding the threshold value; (ii) comparing the quantified number to a microsatellite instability proportion threshold; and (iii) determining if the quantified number exceeds the microsatellite instability proportion threshold, wherein if the quantified number exceeds the microsatellite instability proportion threshold, the human diagnosed as having colorectal cancer has microsatellite instability;

wherein the at least one antibody and/or the at least one small molecule is selected from the group consisting of Avastin (Bevacizumab); Bevacizumab; Camptosar (Irinotecan Hydrochloride); Capecitabine; Cetuximab; Cyramza (Ramucirumab); Eloxatin (Oxaliplatin); Erbitux (Cetuximab); 5-FU (Fluorouracil Injection); Irinotecan Hydrochloride; Leucovorin Calcium; Lonsurf (Trifluridine and Tipiracil Hydrochloride); Nivolumab; Opdivo (Nivolumab); Oxaliplatin; Panitumumab; Ramucirumab; Regorafenib; Stivarga (Regorafenib); Trifluridine and Tipiracil Hydrochloride; Vectibix (Panitumumab); Wellcovorin (Leucovorin Calcium); Xeloda (Capecitabine); Zaltrap (Ziv-Aflibercept); and Ziv-Aflibercept; and wherein the plurality of microsatellite loci are at least 10, 20, 30, 40, 50, 60, 70, 80, 90, 100, 110, 120, 130, 140, 150, or 160 microsatellite loci selected from the group consisting of microsatellite loci 1-170:

| microsatellite locus | chromosome location | start coordinate | end coordinate |
|---|---|---|---|
| 1 | chr1 | 32936733 | 32936750 |
| 2 | chr1 | 46859627 | 46859640 |
| 3 | chr1 | 149929093 | 149929109 |
| 4 | chr1 | 235344151 | 235344170 |
| 5 | chr2 | 5699709 | 5699727 |
| 6 | chr2 | 5700420 | 5700434 |
| 7 | chr2 | 14638213 | 14638234 |
| 8 | chr2 | 39309548 | 39309575 |
| 9 | chr2 | 47414420 | 47414447 |
| 10 | chr2 | 51061373 | 51061415 |
| 11 | chr2 | 66435743 | 66435767 |
| 12 | chr2 | 95183613 | 95183636 |
| 13 | chr2 | 98998132 | 98998145 |
| 14 | chr2 | 102762122 | 102762138 |
| 15 | chr2 | 129982139 | 129982152 |
| 16 | chr2 | 173266783 | 173266800 |
| 17 | chr3 | 70959190 | 70959203 |
| 18 | chr3 | 123614028 | 123614044 |
| 19 | chr4 | 39500102 | 39500120 |
| 20 | chr4 | 54732045 | 54732070 |
| 21 | chr4 | 151662755 | 151662771 |
| 22 | chr5 | 112877981 | 112878021 |
| 23 | chr5 | 140115261 | 140115276 |
| 24 | chr5 | 181260427 | 181260439 |
| 25 | chr6 | 11714406 | 11714420 |
| 26 | chr7 | 1747883 | 1747900 |
| 27 | chr7 | 143306249 | 143306274 |
| 28 | chr8 | 33498673 | 33498689 |
| 29 | chr8 | 40154248 | 40154264 |
| 30 | chr8 | 58148166 | 58148186 |

-continued

| microsatellite locus | chromosome location | start coordinate | end coordinate |
|---|---|---|---|
| 31 | chr8 | 93925321 | 93925334 |
| 32 | chr9 | 84003046 | 84003063 |
| 33 | chr9 | 126837838 | 126837854 |
| 34 | chr10 | 21518540 | 21518553 |
| 35 | chr10 | 119137173 | 119137195 |
| 36 | chr11 | 5666090 | 5666107 |
| 37 | chr11 | 115176312 | 115176326 |
| 38 | chr11 | 125620870 | 125620891 |
| 39 | chr11 | 125893715 | 125893728 |
| 40 | chr12 | 84892141 | 84892158 |
| 41 | chr12 | 130399009 | 130399022 |
| 42 | chr13 | 50013518 | 50013540 |
| 43 | chr14 | 23183137 | 23183158 |
| 44 | chr14 | 64523982 | 64523995 |
| 45 | chr14 | 73492999 | 73493015 |
| 46 | chr16 | 19118464 | 19118481 |
| 47 | chr16 | 29669203 | 29669217 |
| 48 | chr16 | 58543411 | 58543424 |
| 49 | chr17 | 38995870 | 38995910 |
| 50 | chr18 | 649879 | 649894 |
| 51 | chr19 | 11808381 | 11808396 |
| 52 | chr19 | 21378606 | 21378625 |
| 53 | chr19 | 57257698 | 57257723 |
| 54 | chr19 | 57258437 | 57258450 |
| 55 | chr19 | 57262350 | 57262363 |
| 56 | chr20 | 59922426 | 59922441 |
| 57 | chr21 | 34103315 | 34103331 |
| 58 | chrX | 2904903 | 2904920 |
| 59 | chrX | 38805564 | 38805577 |
| 60 | chrX | 101413944 | 101413957 |
| 61 | chrX | 102154282 | 102154298 |
| 62 | chrX | 102658669 | 102658683 |
| 63 | chrX | 102751949 | 102751969 |
| 64 | chrX | 145825169 | 145825191 |
| 65 | chr1 | 103663067 | 103663077 |
| 66 | chr1 | 103757205 | 103757215 |
| 67 | chr1 | 116112562 | 116112575 |
| 68 | chr1 | 13782253 | 13782262 |
| 69 | chr1 | 150714123 | 150714133 |
| 70 | chr1 | 151224226 | 151224235 |
| 71 | chr1 | 159062696 | 159062706 |
| 72 | chr1 | 200624913 | 200624921 |
| 73 | chr1 | 221702319 | 221702330 |
| 74 | chr1 | 236897645 | 236897660 |
| 75 | chr1 | 28459218 | 28459228 |
| 76 | chr1 | 52784862 | 52784872 |
| 77 | chr1 | 88983825 | 88983836 |
| 78 | chr10 | 72893710 | 72893720 |
| 79 | chr11 | 105007313 | 105007323 |
| 80 | chr11 | 105008959 | 105008969 |
| 81 | chr11 | 120479927 | 120479935 |
| 82 | chr11 | 63382198 | 63382209 |
| 83 | chr11 | 65501008 | 65501020 |
| 84 | chr12 | 118150956 | 118150974 |
| 85 | chr12 | 119728455 | 119728465 |
| 86 | chr12 | 13211492 | 13211502 |
| 87 | chr12 | 31282674 | 31282685 |
| 88 | chr12 | 54011395 | 54011406 |
| 89 | chr12 | 96286155 | 96286166 |
| 90 | chr13 | 46771334 | 46771348 |
| 91 | chr13 | 49350729 | 49350739 |
| 92 | chr13 | 57725300 | 57725311 |
| 93 | chr14 | 19668967 | 19668978 |
| 94 | chr14 | 53046721 | 53046733 |
| 95 | chr15 | 30113885 | 30113899 |
| 96 | chr15 | 37099551 | 37099563 |
| 97 | chr15 | 41852769 | 41852780 |
| 98 | chr15 | 72572067 | 72572077 |
| 99 | chr16 | 14889234 | 14889243 |
| 100 | chr17 | 1423460 | 1423474 |
| 101 | chr17 | 4539344 | 4539362 |
| 102 | chr17 | 45539269 | 45539279 |
| 103 | chr17 | 46306192 | 46306202 |
| 104 | chr17 | 46523767 | 46523777 |
| 105 | chr17 | 56938993 | 56939007 |
| 106 | chr17 | 58357799 | 58357806 |

-continued

| microsatellite locus | chromosome location | start coordinate | end coordinate |
|---|---|---|---|
| 107 | chr18 | 23529756 | 23529766 |
| 108 | chr18 | 319944 | 319955 |
| 109 | chr18 | 33333178 | 33333188 |
| 110 | chr18 | 9954236 | 9954249 |
| 111 | chr19 | 12463926 | 12463947 |
| 112 | chr19 | 13993876 | 13993890 |
| 113 | chr19 | 44158121 | 44158134 |
| 114 | chr19 | 9251064 | 9251075 |
| 115 | chr2 | 106426090 | 106426102 |
| 116 | chr2 | 108729222 | 108729232 |
| 117 | chr2 | 118096518 | 118096531 |
| 118 | chr2 | 147926116 | 147926124 |
| 119 | chr2 | 151379531 | 151379545 |
| 120 | chr2 | 182942165 | 182942175 |
| 121 | chr2 | 196666794 | 196666805 |
| 122 | chr2 | 202300378 | 202300388 |
| 123 | chr2 | 210315041 | 210315052 |
| 124 | chr2 | 55234233 | 55234243 |
| 125 | chr2 | 63842143 | 63842158 |
| 126 | chr2 | 87757451 | 87757462 |
| 127 | chr2 | 8858645 | 8858657 |
| 128 | chr20 | 53875234 | 53875245 |
| 129 | chr20 | 60012728 | 60012738 |
| 130 | chr21 | 28966883 | 28966894 |
| 131 | chr21 | 32601784 | 32601798 |
| 132 | chr22 | 38683915 | 38683930 |
| 133 | chr3 | 101459057 | 101459067 |
| 134 | chr3 | 113658634 | 113658645 |
| 135 | chr3 | 131014202 | 131014213 |
| 136 | chr3 | 165187860 | 165187871 |
| 137 | chr3 | 170997894 | 170997904 |
| 138 | chr3 | 25719646 | 25719656 |
| 139 | chr3 | 30650379 | 30650389 |
| 140 | chr3 | 51380172 | 51380179 |
| 141 | chr5 | 159099526 | 159099541 |
| 142 | chr5 | 162067984 | 162067996 |
| 143 | chr5 | 177302735 | 177302747 |
| 144 | chr5 | 58974630 | 58974642 |
| 145 | chr5 | 68288684 | 68288696 |
| 146 | chr5 | 78450039 | 78450050 |
| 147 | chr5 | 80675095 | 80675103 |
| 148 | chr5 | 83641432 | 83641442 |
| 149 | chr5 | 88722571 | 88722584 |
| 150 | chr6 | 167040031 | 167040043 |
| 151 | chr6 | 43054238 | 43054250 |
| 152 | chr6 | 49492281 | 49492291 |
| 153 | chr6 | 55874913 | 55874927 |
| 154 | chr6 | 70861991 | 70862003 |
| 155 | chr6 | 88143811 | 88143822 |
| 156 | chr7 | 135619945 | 135619955 |
| 157 | chr7 | 30633896 | 30633911 |
| 158 | chr7 | 54752300 | 54752311 |
| 159 | chr7 | 75193019 | 75193032 |
| 160 | chr7 | 95359943 | 95359960 |
| 161 | chr8 | 23854553 | 23854565 |
| 162 | chr8 | 33499307 | 33499320 |
| 163 | chr8 | 39103749 | 39103760 |
| 164 | chr8 | 7489344 | 7489353 |
| 165 | chr8 | 7822205 | 7822214 |
| 166 | chr8 | 78717503 | 78717517 |
| 167 | chr9 | 107331689 | 107331701 |
| 168 | chr9 | 83969307 | 83969318 |
| 169 | chrX | 101883466 | 101883477 |
| 170 | chrX | 18164977 | 18164992 |

17. The method of claim 16, wherein the plurality of microsatellite loci are at least 58 microsatellite loci selected from the group consisting of microsatellite loci: 1-64.

18. The method of claim 16, wherein the plurality of microsatellite loci corresponds to the microsatellite loci:

| Chr. | Coordinate | Coordinate |
| --- | --- | --- |
| chr1 | 149929093 | 149929109 |
| chr1 | 235344151 | 235344170 |
| chr1 | 32936733 | 32936750 |
| chr1 | 46859627 | 46859640 |
| chr10 | 119137173 | 119137195 |
| chr10 | 21518540 | 21518553 |
| chr11 | 115176312 | 115176326 |
| chr11 | 125620870 | 125620891 |
| chr11 | 125893715 | 125893728 |
| chr11 | 5666090 | 5666107 |
| chr12 | 130399009 | 130399022 |
| chr12 | 84892141 | 84892158 |
| chr13 | 50013518 | 50013540 |
| chr14 | 23183137 | 23183158 |
| chr14 | 64523982 | 64523995 |
| chr14 | 73492999 | 73493015 |
| chr16 | 19118464 | 19118481 |
| chr16 | 29669203 | 29669217 |
| chr16 | 58543411 | 58543424 |
| chr18 | 649879 | 649894 |
| chr19 | 11808381 | 11808396 |
| chr19 | 21378606 | 21378625 |
| chr19 | 57257698 | 57257723 |
| chr19 | 57258437 | 57258450 |
| chr19 | 57262350 | 57262363 |
| chr2 | 102762122 | 102762138 |
| chr2 | 129982139 | 129982152 |
| chr2 | 14638213 | 14638234 |
| chr2 | 173266783 | 173266800 |
| chr2 | 39309548 | 39309575 |
| chr2 | 47414420 | 47414447 |

-continued

| Chr. | Coordinate | Coordinate |
| --- | --- | --- |
| chr2 | 5700420 | 5700434 |
| chr2 | 66435743 | 66435767 |
| chr2 | 95183613 | 95183636 |
| chr2 | 98998132 | 98998145 |
| chr20 | 59922426 | 59922441 |
| chr21 | 34103315 | 34103331 |
| chr3 | 123614028 | 123614044 |
| chr3 | 70959190 | 70959203 |
| chr4 | 151662755 | 151662771 |
| chr4 | 39500102 | 39500120 |
| chr4 | 54732045 | 54732070 |
| chr5 | 140115261 | 140115276 |
| chr6 | 11714406 | 11714420 |
| chr7 | 143306249 | 143306274 |
| chr7 | 1747883 | 1747900 |
| chr8 | 33498673 | 33498689 |
| chr8 | 40154248 | 40154264 |
| chr8 | 93925321 | 93925334 |
| chr9 | 126837838 | 126837854 |
| chr9 | 84003046 | 84003063 |
| chrX | 101413944 | 101413957 |
| chrX | 102154282 | 102154298 |
| chrX | 102658669 | 102658683 |
| chrX | 102751949 | 102751969 |
| chrX | 145825169 | 145825191 |
| chrX | 2904903 | 2904920 |
| chrX | 38805564 | 38805577. |

\* \* \* \* \*